(12) United States Patent
Devasthale et al.

(10) Patent No.: US 8,754,211 B2
(45) Date of Patent: Jun. 17, 2014

(54) AZOLOTRIAZINONE MELANIN CONCENTRATING HORMONE RECEPTOR-1 ANTAGONISTS

(71) Applicant: Bristol-Myers Squibb Company, Princeton, NJ (US)

(72) Inventors: Pratik Devasthale, Plainsboro, NJ (US); William N. Washburn, Titusville, NJ (US); Kishore V. Renduchintala, Hyderabad (IN); Radhakrishnan Sridhar, Trichy (IN)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 14/041,665

(22) Filed: Sep. 30, 2013

(65) Prior Publication Data
US 2014/0031337 A1    Jan. 30, 2014

Related U.S. Application Data

(62) Division of application No. 13/122,617, filed as application No. PCT/US2009/059941 on Oct. 8, 2009, now Pat. No. 8,580,959.

(60) Provisional application No. 61/103,677, filed on Oct. 8, 2008.

(51) Int. Cl.
| C07D 487/04 | (2006.01) |
| C07D 401/04 | (2006.01) |
| C07D 401/14 | (2006.01) |
| C07D 403/04 | (2006.01) |
| C07D 403/14 | (2006.01) |
| A61K 31/4162 | (2006.01) |
| A61K 31/4188 | (2006.01) |
| A61K 31/53 | (2006.01) |
| A61P 3/04 | (2006.01) |
| A61P 3/10 | (2006.01) |

(52) U.S. Cl.
USPC ........... 544/184; 544/111; 544/183; 514/243; 514/231.5

(58) Field of Classification Search
USPC ................ 544/183, 184, 111; 514/243, 231.5
See application file for complete search history.

(56) References Cited

U.S. PATENT DOCUMENTS 8,580,959 B2 * 11/2013 Devasthale et al. ........... 544/183
2007/0093509 A1    4/2007 Washburn et al.

FOREIGN PATENT DOCUMENTS

| WO | WO2005/103039 A1 | 11/2005 |
| WO | WO2007/050723 A1 | 5/2007 |
| WO | WO2007/092416 A2 | 8/2007 |

OTHER PUBLICATIONS

Borowsky, B. et al., "Antidepressant, anxiolytic and anorectic effects of a melanin-concentrating hormone-1 receptor antagonist", Nature Medicine, vol. 8(8), pp. 825-830 (2002).
Gehlert, D. et al., "Preclinical Evaluation of Melanin-Concentrating Hormone Receptor 1 Antagonism for the Treatment of Obesity and Depression", The J. of Pharmacology and Experimental Therapeutics, vol. 329(2), pp. 429-438 (2009).
Kokkotou, E. et al., "Melanin-concentrating hormone as a mediator of intestinal inflammation", PNAS, vol. 105(30), pp. 10613-10618 (2008).
Kowalski, T. et al., "Melanin-concentrating hormone-1 receptor antagonism decreases feeding by reducing meal size", European Journal of Pharmacology, vol. 497, pp. 41-47 (2004).
Kowalski, T. at al., "Therapeutic potential of melanin-concentrating hormone-1 receptor antagonists for the treatment of obesity", Expert Opinion Investig. Drugs, vol. 13(9), pp. 1113-1122 (2004.
Takekawa, S. et al., "T-226296: a novel, orally active and selective melanin-concentrating hormone receptor antagonist", European Journal of Pharmacology, vol. 438, pp. 129-135 (2002).
Ulven, T. et al., "6-Acylamino-2aminoquinolines as Potent Melanin-Concentrating Hormone 1 Receptor Antagonists. Identification, Structure-Activity Relationship, and Investigation of Binding Mode", J. Medical Chemistry, vol. 48, pp. 5684-5697 (2005).
The Mayo Clinic, Type 1 diabetes, Treatment and drugs, http://www.mayoclinic.com/health/type-1-diabetes/DSOO329/DSECTION=treatments-and-drugs, accessed Oct. 10, 2012.
Banker, G.S. at al., "Modern Pharmaceutices, 3ed." Marcel Dekker, NY, 1996 pp. 451 and 596.
Jeon, J.Y. at al., "Diabetes", vol. 55, pp. 428-434 2006.
Luthin, D.R., "Life Sciences" vol. 81, pp. 423-440.
Wolff, Manfred E., Burger's Medicinal Chemistry, 5ed, Part 1, John Wiley & Sons, pp. 975-977 1995.

* cited by examiner

*Primary Examiner* — Venkataraman Balasubramanian
(74) *Attorney, Agent, or Firm* — Jing G. Sun; Burton Rodney

(57) ABSTRACT

The present application provides compounds that are useful as MCHR1 antagonists, especially for the treatment of obesity, including all stereoisomers, solvates, prodrugs and pharmaceutically acceptable forms thereof according to Formula I

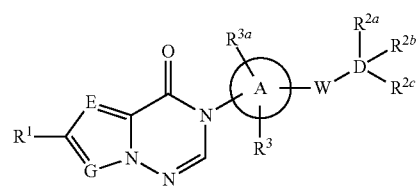

wherein the variables are defined herein.

13 Claims, No Drawings

AZOLOTRIAZINONE MELANIN CONCENTRATING HORMONE RECEPTOR-1 ANTAGONISTS

CROSS-REFERENCE TO RELATED APPLICATIONS

The present application is a Divisional of 371 application with Serial No. 13/122,617 (PCT/US2009/059941, filed Oct. 8, 2009), now allowed, which claims priority benefit of U.S. provisional application Ser. No. 61/103,677, filed Oct. 8, 2008; the entire contents of these applications are incorporated by reference herein.

FIELD OF THE INVENTION

The present invention relates to azolotriazinone melanin concentrating hormone receptor-1 (MCHR1) antagonists, pharmaceutical compositions containing azolotriazinone MCHR1 antagonists and methods of treating diabetes, obesity and related diseases employing such MCHR1 antagonists.

BACKGROUND

Several lines of pharmacological and genetic evidence support the role of Melanin Concentrating Hormone Receptor-1 (hereafter "MCHR1") as a modulator of food intake and body weight. Central administration of MCH increases food intake and body weight in both rats and mice. Chronic ICV infusion of MCH causes increased food intake and ultimately obesity in mice, while infusion of an MCH peptide antagonist blocks MCH-induced food intake and results in weight loss and decreased feeding in diet-induced obese mice.

The expression of both the MCH peptide and receptor are modulated by nutritional status. MCH mRNA is upregulated both in hyperphagic obese mice (ob/ob), and fasted animals. Targeted disruption of the gene for MCH peptide results in hypophagia and leanness. Disruption of the MCHR1 gene causes leanness, altered metabolism, and hyperlocomotion accompanied by mild hyperphagia. Conversely, over-expression of MCH peptide results in hyperphagia, obesity and diabetes. Small molecule MCHR1 antagonists have been shown to cause weight loss in rodent weight and feeding models after both oral and intraperitoneal administration; *Eur. J. Pharmacol.*, 438:129-135 (2002); *Nat. Med.*, 8:825-830 (2002); *Eur. J. Pharmacol.*, 497:41-47 (2004).

MCHR1 has also been reported to play a key role in the pathogenesis of acute experimental colitis and possibly human IBD (inflammatory bowel disease). It has been shown that immunoneutralization is an effective treatment for TNBS-induced colitis. Kokkotou, E. et al., "Melanin-concentrating hormone as a mediator of intestinal inflammation", *PNAS*, 105(30):10613-10618 (Jul. 29, 2008).

In addition, MCH and MCHR1 has also been reported to play a role in the endocrine and behavioral responses to stress. Treatment of rats and mice with MCHR antagonists produce a robust anti-depressant and anti-anxiolytic effect. (JPET DOI:10.1124/jpet.108.143362)

Numerous non-peptide MCHR1 antagonists have been disclosed. The scope of the genus for each reflects a common perception regarding the criteria required for ligand recognition as MCHR1 agonists. A recent review of MCHR1 patent disclosures emphasized the commonality of these structures by the following description; "Ubiquitous throughout the MCH patent literature are molecules consisting of a central scaffold to which linkers to an aryl or heteroaryl group and a basic amino functionality are attached" (Kowalski, T. J. et al., *Exp. Opin. Invest. Drugs,* 13:1113-1122 (2004)). Pharmacophore models of these geni consistently envision a presumed prerequisite electrostatic interaction between a basic amine center of the antagonist ligand and aspartic acid 123 of the receptor which presumably is envisaged to emulate the mandatory interaction between arginine 14 of MCH peptide agonists with aspartic acid 123 of the MCHR1 receptor. (Ulven, T. et al., *J. Med. Chem.,* 48:5684-5697 (2005)). However, incorporation of this basic amine in a MCHR1 antagonist increases substantially the probability of binding to off-target ion-channels and biogenic amine receptors.

U.S. Patent Publication No. 2007/0093509 A1 published Apr. 26, 2007 discloses a series of novel high affinity selective MCHR1 antagonists of formula A:

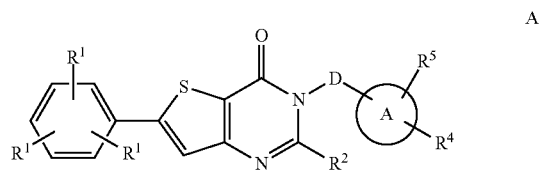

wherein,
A is phenyl or a monocyclic heteroaryl;
D is $CH_2$ or a direct bond;
$R^1$ is independently selected from hydrogen, halogen, lower alkyl, lower cycloalkyl, $CF_3$, $OR^6$ or $SR^6$;
$R^2$ is hydrogen or lower alkyl;
$R^4$ is hydroxyl or $G-D^2-Z_n$;
n is an integer from 1 to 3;
$R^5$ is hydrogen, halogen, lower alkyl, lower cycloalkyl, $CF_3$, $SR^6$, lower alkoxy, lower cycloalkoxy, CN, $CONR^7R^7$, $SOR^6$, $SO_2R^6$, $NR^7COR^7$, $NR^7CO_2R^7$, $CO_2R^6$, heteroaryl, $NR^7SO_2R^6$ or $COR^6$;
G is O, S or $CR^7R^7$;
$D^2$ is a direct bond, lower alkyl, lower cycloalkyl or a 4 to 6-membered non-basic heterocycle;
Z is hydrogen, hydroxyl, lower alkoxy, lower cycloalkoxy, $OCONR^7R^7$, CN, $CONR^7R^7$, $SOR^6$, $SO_2R^6$, $NR^7COR^7$, $NR^7CO_2R^7$, $CO_2R^6$, heteroaryl, $NR^6SO_2R^6$ or $COR^6$;
$R^6$ is independently selected from lower alkyl or lower cycloalkyl; and
$R^7$ is independently selected from hydrogen, lower alkyl or lower cycloalkyl, wherein two $R^7$ and the atom to which they are attached may optionally form a ring of 4 to 7 atoms.

There is currently a need in the art for additional small molecule antagonists of MCHR1.

SUMMARY OF THE INVENTION

The present invention is directed to compounds that are useful as MCHR1 antagonists having the following formula I:

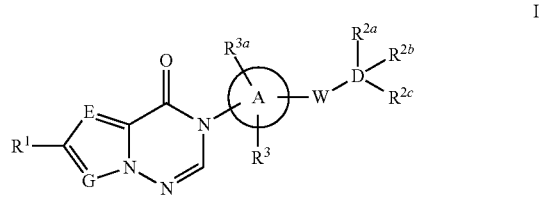

wherein

is selected from the group consisting of monocyclic aryl or monocyclic heteroaryl; and is preferably phenyl, pyridinyl, or pyrimidinyl;

W is selected from the group consisting of a direct bond, —O—, and —N($R^6$)— provided that if W is a direct bond, D is a cyclic amine that is attached to A via the nitrogen atom of the cyclic amine;

D is selected from the group consisting of a direct bond, substituted or unsubstituted $C_1$ to $C_4$ alkyl, substituted or unsubstituted $C_3$ to $C_7$ cycloalkyl, cycloalkylalkyl, and 4- to 6-membered cyclic amines;

E and G are independently N or CH provided that both are not N;

$R^1$ is substituted or unsubstituted phenyl or substituted or unsubstituted monocyclic heteroaryl, and is preferably phenyl, pyridinyl, or pyrimidinyl;

$R^{2a}$, $R^{2b}$, and $R^{2c}$ are independently selected from the group consisting of hydrogen, halo, cyano, hydroxyl, —$NR^5R^{5a}$, —$SO_2R^{34}$, —$CO_2R^{35}$, —$NR^5CO_2R^{21}$, —$NR^5COR^{21}$, substituted or unsubstituted $C_1$ to $C_4$ alkyl, substituted or unsubstituted $C_3$ to $C_7$ cycloalkyl, substituted or unsubstituted 4- to 6-membered cyclic amines wherein said cyclic amine is optionally substituted with —OH, carbonylamino, alkoxycarbonylamino, or at least one of $R^{2a}$, $R^{2b}$, and $R^{2c}$ is a prodrug moiety selected from amino acid esters or phosphoric acid esters wherein said amino acid ester has the formula —$OC(O)CH(NH_2)R^{31}$, wherein $R^{31}$ is H or $C_1$ to $C_4$ alkyl; or any two of $R^{2a}$, $R^b$, or $R^{2c}$, may be taken together to form a ring; provided that if D is a direct bond, $R^{2a}$, $R^{2b}$, and $R^{2c}$ must be selected from H, alkyl, or cycloalkyl;

$R^3$ and $R^{3a}$ are each independently selected from the group consisting of hydrogen, hydroxyl, lower alkoxy, halo, CN, substituted or unsubstituted $C_1$ to $C_4$ alkyl, perfluoroalkyl, substituted or unsubstituted $C_3$ to $C_7$ cycloalkyl, cycloalkoxy, amino, alkylamino, dialkylamino, and aminoalkyl, wherein $R^3$ or $R^{3a}$ and D may optionally be taken together with the atoms to which they are attached to form a 5- to 7-membered ring;

$R^5$ and $R^{5a}$ are the same or different and are independently selected from the group consisting of hydrogen, substituted or unsubstituted lower alkyl, hydroxyalkyl, hydroxyalkylcycloalkyl, substituted or unsubstituted heterocycloalkyl, acyl, alkoxycarbonyl, carboxyalkyl, substituted or unsubstituted cycloalkyl, and substituted or unsubstituted cycloalkylalkyl, wherein the $R^5$ and $R^{5a}$ groups and the N atom to which they are attached may form a ring;

$R^{34}$ is alkyl;
$R^{21}$ is H or alkyl;
$R^{35}$ is H or alkyl; and
$R^6$ is selected from the group consisting of H, $C_1$ to $C_4$ alkyl and $C_3$ to $C_7$ cycloalkyl.

According to one preferred embodiment, D is a cyclic amine selected from the group consisting of pyrrolidinyl, morpholinyl, azetidinyl, piperidinyl, morphilinyl, and $R^{2a}$, $R^{2b}$, and $R^{2c}$ are each independently, H, —OH, —N($R^5$, $R^{5a}$), —$NR^5CO_2R^{21}$, —$NR^5COR^{21}$, -azetidinyl, oxo, the amino acid ester residue, —$OC(O)C(NH_2)R^{31}$, or $R^{2a}$ and $R^{2b}$ are taken together to form a cycloalkyl ring, such as cyclobutyl, substituted with a hydroxyalkyl such as —$CH_2OH$.

According to one embodiment of the present invention, D is a direct bond, or alkyl group such as methyl, ethyl, or propyl and at least one of $R^{2a}$, $R^{2b}$, and $R^{2c}$ is independently H, —OH, —$OC(O)C(NH_2)R^{31}$, hydroxyalkyl, cyclopropyl, pyrrolidinyl, —$SO_2R^{34}$, —$CO_2H$, or $R^{2a}$ and $R^{2b}$ are joined together to form a cycloalkyl substituted with halo or hydroxyl.

According to one embodiment of the present invention, compounds may have the following formula (Including pharmaceutically acceptable salts thereof):

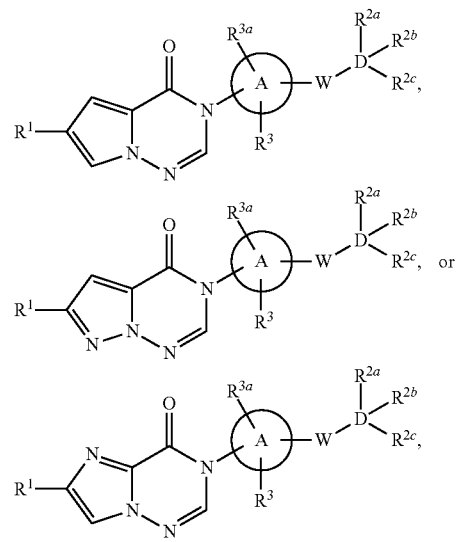

wherein

is phenyl, pyrimidinyl, or pyridinyl;

$R^1$ is phenyl, pyrimidinyl, or pyridinyl optionally substituted with halo;

$R^{3a}$ and $R^3$ are independently H or methoxy;

W is a direct bond or O, provided that if W is a direct bond, D is a cyclic amine that is attached to A via the nitrogen atom of the cyclic amine;

D is a direct bond, methyl, ethyl, propyl, or a cyclic amine selected from pyrrolidinyl, morpholinyl, azetidinyl, piperidinyl, morphilinyl; and $R^{2a}$, $R^{2b}$, and $R^{2c}$ are independently selected from the group consisting of hydrogen, halo, cyano, hydroxyl, —$NR^5R^{5a}$, —$SO_2R^{34}$, substituted or unsubstituted $C_1$ to $C_4$ alkyl, substituted or unsubstituted $C_3$ to $C_7$ cycloalkyl, substituted or unsubstituted 4- to 6-membered cyclic amines wherein said cyclic amine is optionally substituted with —OH, carbonylamino, alkoxycarbonylamino, or at least one of $R^{2a}$, $R^{2b}$, and $R^{2c}$ is a prodrug moiety selected from amino acid esters or phosphoric acid esters wherein said amino acid ester has the formula —$OC(O)CH(NH_2)R^{31}$, wherein $R^{31}$ is H or $C_1$ to $C_4$ alkyl; or any two of $R^{2a}$, $R^b$, or $R^{2c}$, may be taken together to form a ring, provided that if D is a direct bond, $R^{2a}$, $R^b$, and $R^{2c}$ are each independently H, alkyl, or cycloalkyl.

DETAILED DESCRIPTION OF THE INVENTION

The present application provides compounds, including all stereoisomers, solvates, prodrugs and pharmaceutically acceptable forms thereof according to Formula I. Additionally, the present application provides pharmaceutical compositions containing at least one compound according to Formula I together with a pharmaceutically acceptable excipient and/or carrier and optionally at least one additional therapeutic agent, such as an antidiabetic, antiobesity, anti-inflammatory, antidepressant, or anti-anxiety agent. Finally, the present application provides methods for treating a patient suffering from an MCHR-1 modulated disease or disorder such as, for example, obesity, diabetes, depression, anxiety or inflammatory bowel disease by administration of a therapeutically effective dose of a compound according to Formula I.

Thus, according to the present invention, compounds are provided having the following Formula I:

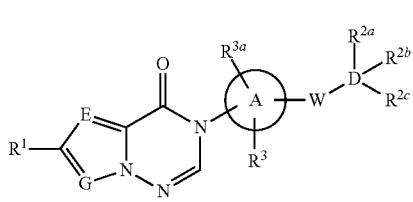

wherein

is selected from the group consisting of monocyclic aryl, preferably phenyl, or monocyclic heteroaryl groups, preferably pyridinyl or pyrimidinyl;

W is selected from the group consisting of a direct bond, —O—, and —N($R^6$)— provided that if W is a direct bond, D is a cyclic amine that is attached to A via the nitrogen D is selected from the group consisting of a direct bond, substituted or unsubstituted $C_1$ to $C_4$ alkyl, substituted or unsubstituted $C_3$ to $C_7$ cycloalkyl, cycloalkylalkyl, and 4- to 6-membered cyclic amines, E and G are independently N or CH provided that both are not N;

$R^1$ is substituted or unsubstituted phenyl or substituted or unsubstituted monocyclic heteroaryl, and is preferably phenyl, pyridinyl, or pyrimidinyl;

$R^{2a}$, $R^{2b}$, and $R^{2c}$ are independently selected from the group consisting of hydrogen, halo, cyano, hydroxyl, —$NR^5R^{5a}$, —$SO_2R^{34}$, —$CO_2R^{35}$ substituted or unsubstituted $C_1$ to $C_4$ alkyl, substituted or unsubstituted $C_3$ to $C_7$ cycloalkyl, substituted or unsubstituted 4- to 6-membered cyclic amines wherein said cyclic amine is optionally substituted with —OH, carbonylamino, alkoxycarbonylamino, or at least one of $R^{2a}$, $R^{2b}$, and $R^{2c}$ is a prodrug moiety selected from amino acid esters or phosphoric acid esters wherein said amino acid ester has the formula —OC(O)CH($NH_2$)$R^{31}$, wherein $R^{31}$ is H or $C_1$ to $C_4$ alkyl; or any two of $R^{2a}$, $R^b$, or $R^{2c}$, may be taken together to form a ring; provided that if D is a direct bond, $R^{2a}$, $R^{2b}$, and $R^{2c}$ are independently H, alkyl, or cycloalkyl;

$R^3$ and $R^{3a}$ are each independently selected from the group consisting of hydrogen, hydroxyl, lower alkoxy, halo, CN, substituted or unsubstituted $C_1$ to $C_4$ alkyl, perfluoroalkyl, substituted or unsubstituted $C_3$ to $C_7$ cycloalkyl, and cycloalkoxy or one of $R^3$ or $R^{3a}$ may be taken together with D and the atoms to which they are attached to form a 5- to 7-membered ring;

$R^5$ and $R^{5a}$ are the same or different and are independently selected from the group consisting of hydrogen, substituted or unsubstituted $C_1$ to $C_4$ alkyl, hydroxyalkyl, hydroxyalkylcycloalkyl, substituted or unsubstituted heterocycloalkyl, acyl, alkoxycarbonyl, carboxyalkyl, substituted or unsubstituted cycloalkyl, and substituted or unsubstituted cycloalkylalkyl, wherein the $R^5$ and $R^{5a}$ groups and the nitrogen atom to which they are attached may form a ring;

$R^{34}$ is alkyl;

$R^{35}$ is H or alkyl; and $R^6$ is selected from the group consisting of H, $C_1$ to $C_4$ alkyl and $C_3$ to $C_7$ cycloalkyl.

According to one preferred embodiment, D is a cyclic amine selected from the group consisting of pyrrolidinyl, morpholinyl, azetidinyl, piperidinyl, morphilinyl, and $R^{2a}$, $R^{2b}$, and $R^{2c}$ are each independently, H, —OH, —N($R^5R^{5a}$), —$NR^5CO_2R^{21}$, —$NR^5COR^{21}$, -azetidinyl, oxo, the amino acid ester residue, —OC(O)C($NH_2$)$R^{31}$, or $R^{2a}$ and $R^{2b}$ are taken together to form a cycloalkyl ring, such as cyclobutyl, substituted with a hydroxyalkyl such as —$CH_2OH$.

According to one embodiment of the present invention, D is an alkyl group such as methyl, ethyl, or propyl and $R^{2a}$, $R^{2b}$, and $R^{2c}$ are each independently H, —OH, —OC(O)C($NH_2$)$R^{31}$, hydroxyalkyl, cyclopropyl, pyrrolidinyl, —$SO_2R^{34}$, —$CO_2H$, or $R^{2a}$ and $R^{2b}$ are joined together to form a cycloalkyl substituted with halo or hydroxyl; or D is a direct bond and $R^{2a}$, $R^{2b}$, and $R^{2c}$ are each independently H, alkyl, or cycloalkyl.

According to one embodiment of the present invention, compounds may have the following formula (Including pharmaceutically acceptable salts thereof):

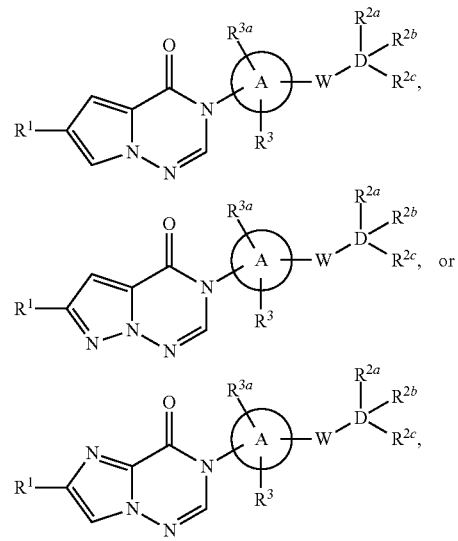

wherein

is phenyl, pyrimidinyl, or pyridinyl;

R[1] is phenyl, pyrimidinyl, or pyridinyl optionally substituted with halo;

R[3a] and R[3] are independently H or methoxy;

W is a direct bond or O, provided that if W is a direct bond, D is a cyclic amine that is attached to A via the nitrogen atom of the cyclic amine;

D is a direct bond, methyl, ethyl, propyl, or a cyclic amine selected from pyrrolidinyl, morpholinyl, azetidinyl, piperidinyl, morphilinyl; and $R^{2a}$, $R^{2b}$, and $R^{2c}$ are independently selected from the group consisting of hydrogen, halo, cyano, hydroxyl, —NR[5]R[5a], —SO$_2$R[34], substituted or unsubstituted $C_1$ to $C_4$ alkyl, substituted or unsubstituted $C_3$ to $C_7$ cycloalkyl, substituted or unsubstituted 4- to 6-membered cyclic amines wherein said cyclic amine is optionally substituted with —OH, carbonylamino, alkoxycarbonylamino, or at least one of $R^{2a}$, $R^{2b}$, and $R^{2c}$ is a prodrug moiety selected from amino acid esters or phosphoric acid esters wherein said amino acid ester has the formula —OC(O)CH(NH$_2$)R[31], wherein R[31] is H or $C_1$ to $C_4$ alkyl; or any two of $R^{2a}$, $R^{b}$, or $R^{2c}$, may be taken together to form a ring.

The R[1] group is preferably phenyl or heteroaryl preferably 2-pyridinyl, 3-pyridinyl or 2-pyrimidinyl, wherein the aryl or heteroaryl is preferably substituted with one to three R[4] substituents at the para-position, and/or meta-positions, and wherein each of the R[4] substituents are the same or different and are independently selected from H, lower alkyl, lower alkoxy, halo, cycloalkyl, and polyfluoroalkyl, such as 4-Cl, 4-CF$_3$, 3-F and 5-cyclopropyl.

The bicyclic core ring

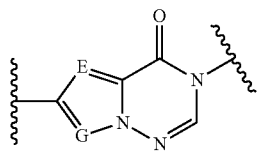

in the formula I compounds of the invention and formula ID compounds (set out below) of the invention will preferably include

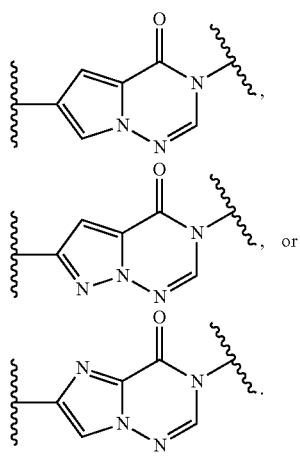

It will be appreciated that where D and/or W is a direct bond or other moiety as defined for D and/or W, the $R^{2a}$, $R^{2b}$ and/or $R^{2c}$ groups will be present, where possible, according to the number of available valences.

Thus, the compounds of formula I of the invention include the following subgenuses:

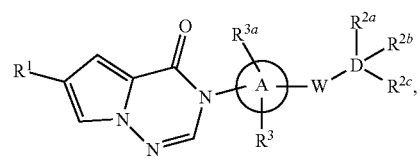
IA

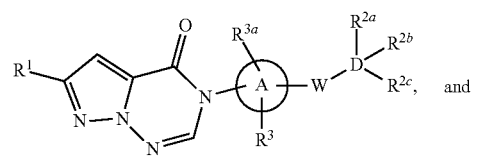
IB
and

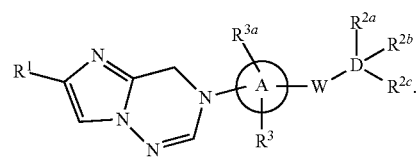
IC

In one embodiment of the compounds of formula I of the invention, compounds are provided having the structure IA

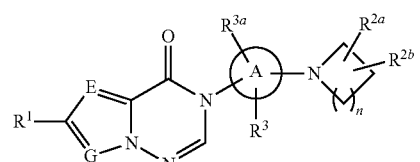
ID wherein

R[1], E, G,

,

R[3] and R[3a] are as defined above with respect to formula I;

n is 1, 2 or 3;

$R^{2a}$ and $R^{2b}$ are the same or different and can be attached to separate carbons on the azo ring in which case $R^{2a}$ and $R^{2b}$ are the same or different and may be independently and are preferably selected from H, NR[5]R[5a], OH, oxo(═O), halo, cyano, acylamino, alkoxycarbonylamino, or hydroxyalkyloxycarbonylamino, and wherein $R^{2a}$ and $R^{2b}$ and the carbons to which they are linked may optionally form a bicyclic heterocycle which can be optionally substituted with one to three substituents which can be the same or different and are independently and preferably selected from OH, CN, or oxo(═O), and wherein $R^{2a}$ and $R^{2b}$ are the same or different and can be attached to a single carbon atom, in which case $R^{2a}$ and $R^{2b}$ may optionally be connected via a ring to form a spirocycle which can optionally be substituted with one to three substituents which may be the same or different and are independently and preferably selected from OH, CN, or oxo(═O).

Examples of preferred
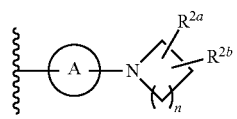
groups include
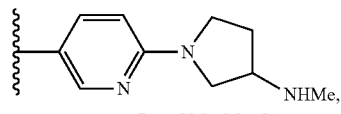
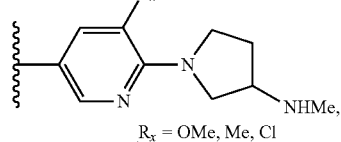
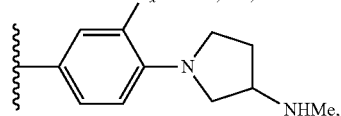
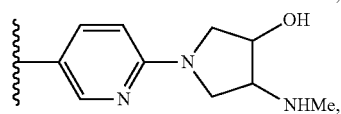
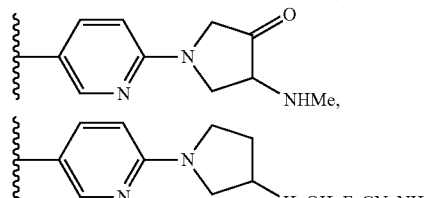
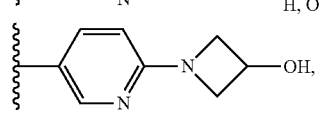
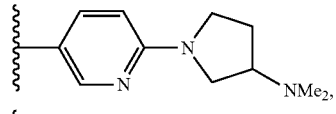
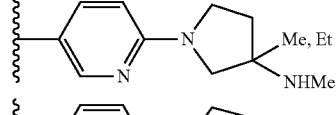
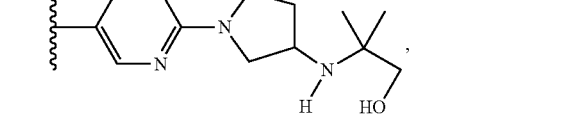
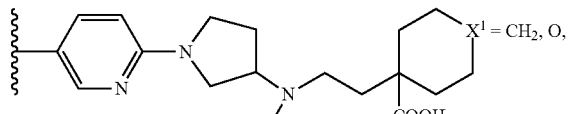
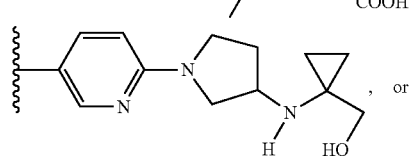
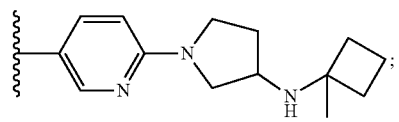
spirocyclics such as
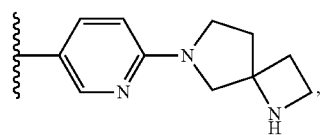
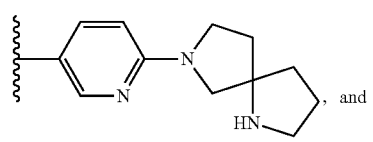, and
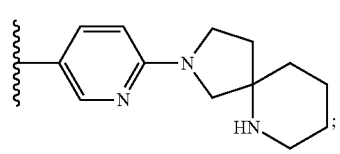;
or
heterocyclic azocycles such as
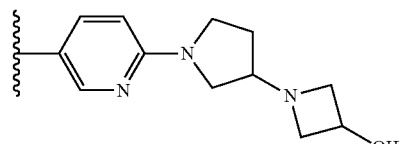;
or
bicyclics such as
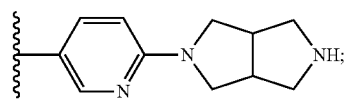 [SMILES: *c1ccc(N2CC3CNCC3C2)nc1];
or
carbamates such as
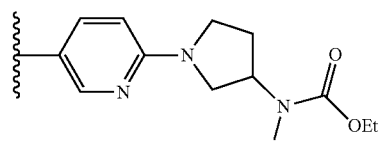
or

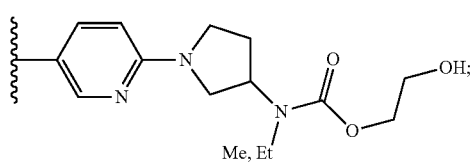

or amides such as

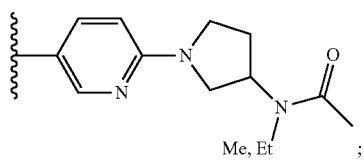

or lactams such as

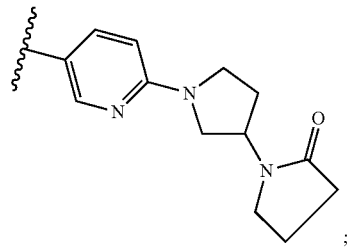 [SMILES: *c1ccc(N2CCC(N3CCCC3=O)C2)nc1]

or oxazolidinones such as

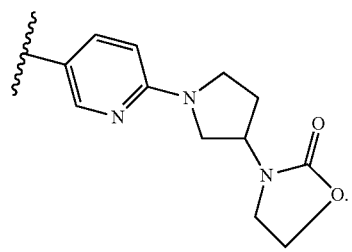 [SMILES: *c1ccc(N2CCC(N3CCOC3=O)C2)nc1]

In some embodiments of the compounds of formula I of the invention, $R^1$ is aryl, preferably phenyl, which may or may not be substituted, and is preferably substituted at the para-position with halogen such as Cl or polyfluoroalkyl such as $CF_3$, including

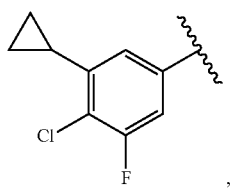

or heteroaryl such as

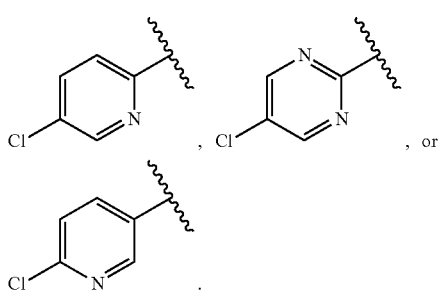

In some embodiments of the compounds of formula I of the invention, E is CH and G is CH or N.

In some embodiments of the compounds of formula I of the invention,

is phenylene or pyridinyl, preferably

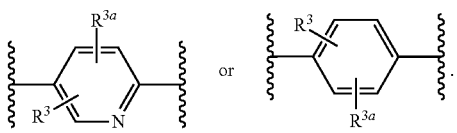

In some embodiments of the compounds of formula I of the invention, $R^3$ is lower alkoxy, preferably —$OCH_3$, or H, halo, or alkyl, and $R^{3a}$ is H.

In some embodiments of the compounds of formula I of the invention, W is O or a direct bond.

In some embodiments of the compounds of formula I of the invention, D is a bond or alkylene.

In some embodiments of the compounds of formula I of the invention, $R^{2a}$ is lower alkyl, such as $CH_3$, hydroxyalkyl such as

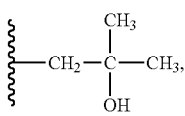

cycloalkyl such as

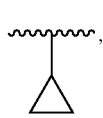

cycloalkylalkyl such as

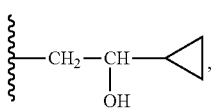

or heterocycloalkyl such as

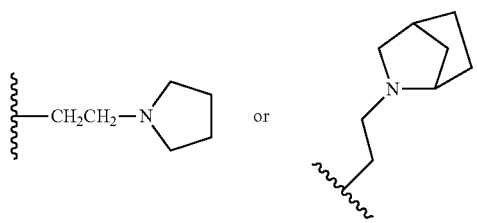

OH, heterocyclyl such as

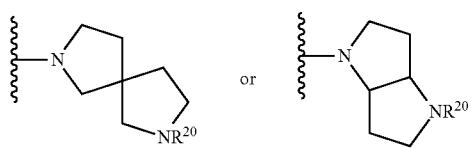

(where $R^{20}$ is lower alkyl),

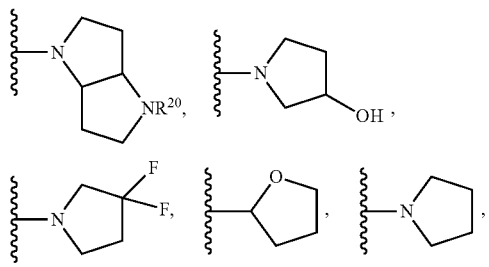

mono- or -dialkylaminoheterocyclyl such as

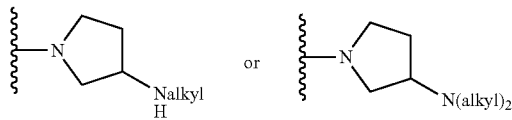

(where alkyl is preferably $CH_3$), $NR^5R^{5a}$ such as

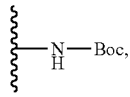

$NH_2$, $NHCH_3$ or $N(CH_3)_2$ or heteroaryl such as

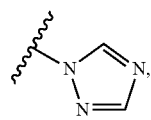

$OSO_2CH_3$ or

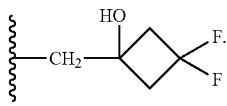 [SMILES: *CC1(O)CC(F)(F)C1]

In some embodiments of the compounds of formula I of the invention, $R^{2b}$ and $R^{2c}$ are independently H, cycloalkyl such as

or lower alkyl such as $CH_3$, or are absent.

In some embodiments of the compounds of formula I of the invention,

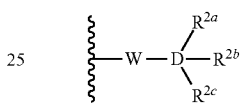

is $-OCH_3$,

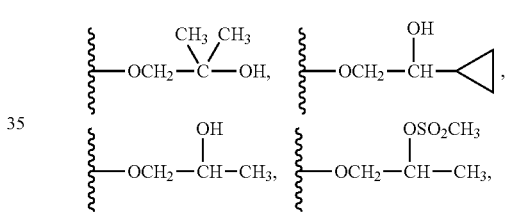

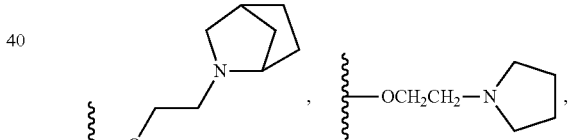

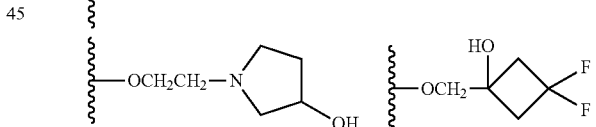

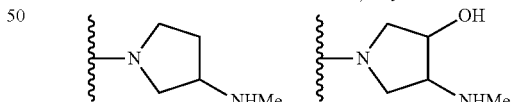

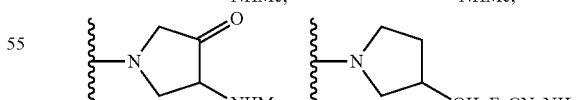

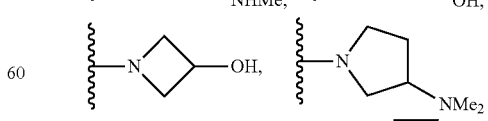

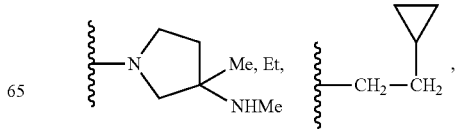

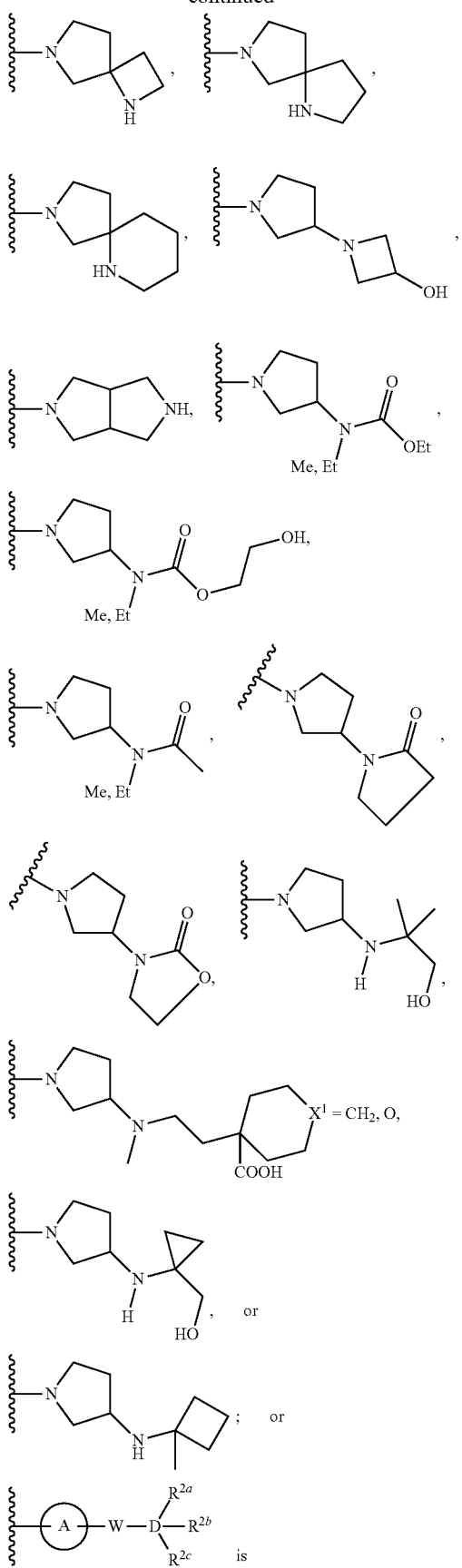
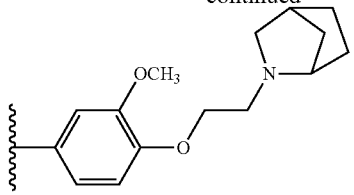
In some embodiments of the compounds of formula I of the invention,
$R^1$ is aryl such as
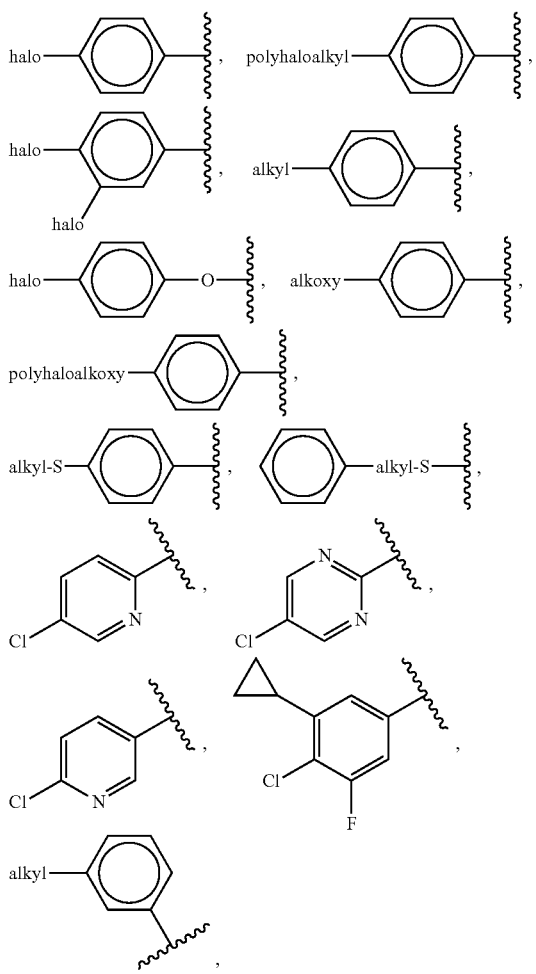
or H, preferably
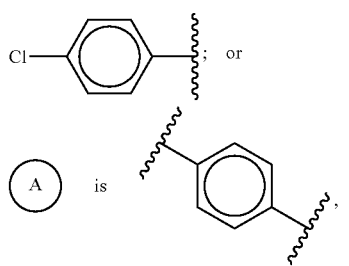

-continued

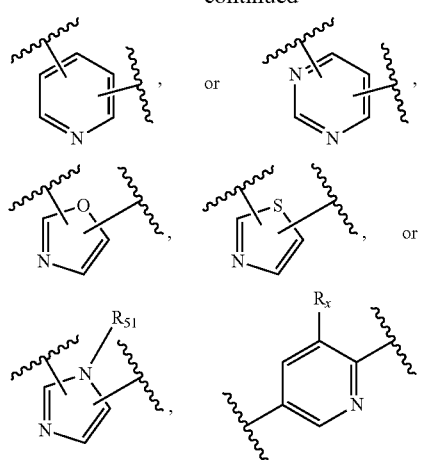

($R_x$=lower alkoxy such as $OCH_3$, lower alkyl such as $CH_3$ or halo such as Cl and where $R^{51}$ is lower alkyl), preferably

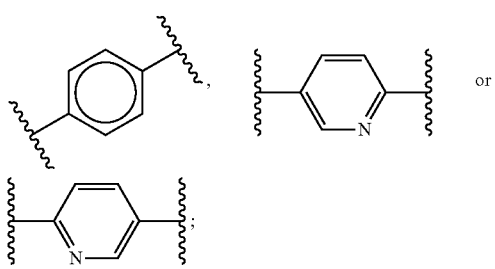

or
R³ is H, alkyl, or alkoxy, preferably $OCH_3$; or
$R^{3a}$ is H; or
D is $CH_2$, $CH_2CH_2$, $CH_2CH_2CH_2$,

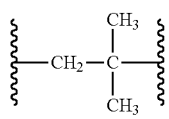

or a bond, preferably $CH_2$ or a bond; or
$R^{2a}$ is heterocyclyl such as

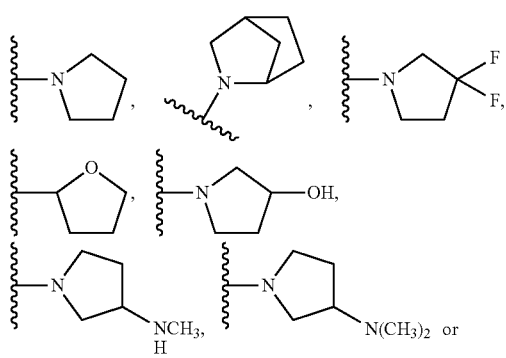

-continued

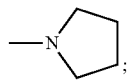

heteroaryl such as

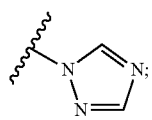 [SMILES: *n1cncn1]

cycloalkyl such as

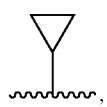 [SMILES: *C1CC1]

$NH_2$, $NHCH_3$,

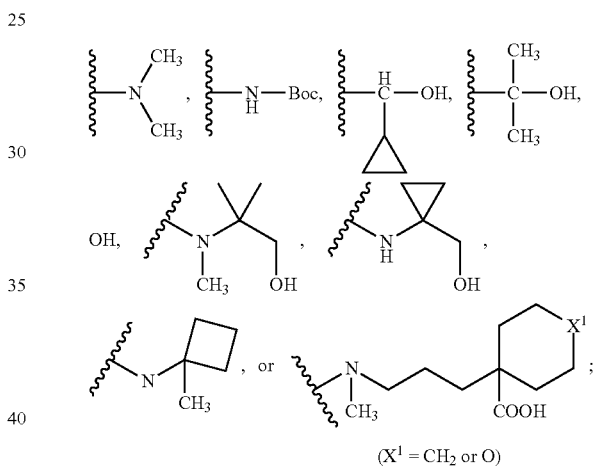

($X^1 = CH_2$ or O)

or
$R^{2b}$ and $R^{2c}$ are each H; or
W is O; or
E is CH; or
G is CH.

In some embodiments of the present invention, pharmaceutical compositions are provided which include at least one compound having the Formula I, as described above, and at least one pharmaceutically acceptable diluent or carrier.

In some embodiments of the present invention, methods are provided for treating a patient suffering from an MCHR1 modulated disease or disorder such as, for example, obesity, diabetes, depression, anxiety or intestinal inflammation, such as inflammatory bowel disease, colitis or Crohn's disease by administration of a therapeutically effective dose of a compound according to Formula I, optionally in combination with other therapeutic agents, such as those described below.

DETAILED DESCRIPTION OF THE INVENTION

Definitions

Unless otherwise indicated, the term "lower alkyl" as employed herein alone or as part of another group includes both straight and branched chain hydrocarbons containing 1 to 8 carbons, and the terms "alkyl" and "alk" as employed herein alone or as part of another group includes both straight and branched chain hydrocarbons containing 1 to 20 carbons, preferably 1 to 10 carbons, more preferably 1 to 8 carbons, in the normal chain, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including 1 to 4 substituents such as halo, for example F, Br, Cl or I or $CF_3$, alkyl, alkoxy, aryl, aryloxy, aryl(aryl) or diaryl, arylalkyl, arylalkyloxy, alkenyl, alkynyl, cycloalkyl, cycloalkenyl, cycloalkylalkyl, cycloalkylalkyloxy, hydroxy, hydroxyalkyl, acyl, alkanoyl, heteroaryl, heteroaryloxy, cycloheteroalkyl, arylheteroaryl, arylalkoxycarbonyl, heteroarylalkyl, heteroarylalkoxy, aryloxyalkyl, aryloxyaryl, alkylamido, alkanoylamino, arylcarbonylamino, nitro, cyano, thiol, haloalkyl, trihaloalkyl and/or alkylthio.

Unless otherwise indicated, the term "cycloalkyl" or "lower cycloalkyl" as employed herein alone or as part of another group includes saturated or partially unsaturated (containing 1 or 2 double bonds) cyclic hydrocarbon groups containing 1 to 3 rings, any one of which may optionally be a spiro substituted cycloalkyl, including monocyclicalkyl, bicyclicalkyl and tricyclicalkyl, containing a total of 3 to 20 carbons forming the rings, preferably 3 to 10 carbons, forming the ring and which may be fused to 1 or 2 aromatic rings as described for aryl, which include cyclopropyl, cyclobutyl, cyclopentyl, cyclohexyl, cycloheptyl, cyclooctyl, cyclodecyl and cyclododecyl, cyclohexenyl,

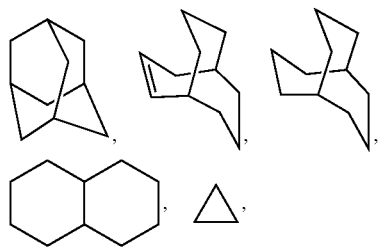

any of which groups may be optionally substituted with 1 to 4 substituents such as halogen, alkyl, alkoxy, hydroxy, aryl, aryloxy, arylalkyl, cycloalkyl, alkylamido, alkanoylamino, oxo, acyl, arylcarbonylamino, nitro, cyano, thiol and/or alkylthio and/or any of the alkyl substituents.

Unless otherwise indicated, the term "cycloalkoxy" or "lower cycloalkoxy" as employed herein alone or as part of another group, represents a 4-, 5- or 6-membered saturated ring containing an oxygen in the ring and includes

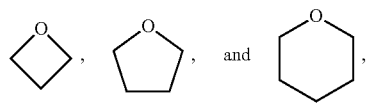

and which may be optionally substituted with 1 or 2 of any of the substituents as set out for cycloalkyl.

The term "heterocyclo", "heterocyclyl" and "heterocyclic" as used herein, alone or as part of another group, represents an unsubstituted or substituted stable 4- to 7-membered monocyclic ring system which may be saturated or unsaturated, and which consists of carbon atoms, with one to four heteroatoms selected from nitrogen, oxygen or sulfur, and wherein the nitrogen and sulfur heteroatoms may optionally be oxidized, and the nitrogen heteroatom may optionally be quaternized. The heterocyclic ring may be attached at any heteroatom or carbon atom which results in the creation of a stable structure. Examples of such heterocyclic groups include, but is not limited to, piperidinyl, piperazinyl, oxopiperazinyl, oxopiperidinyl, oxopyrrolidinyl, oxoazepinyl, azepinyl, pyrrolyl, pyrrolidinyl, furanyl, thienyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isooxazolyl, isoxazolidinyl, morpholinyl, thiazolyl, thiazolidinyl, isothiazolyl, thiadiazolyl, tetrahydropyranyl, thiamorpholinyl, thiamorpholinyl sulfoxide, thiamorpholinyl sulfone, oxadiazolyl and other heterocycles described in Katritzky, A. R. et al., eds., *Comprehensive Heterocyclic Chemistry The Structure, Reactions, Synthesis and Uses of Heterocyclic Compounds*, Pergamon Press, New York, N.Y. (1984); and Katritzky, A. R. et al., eds., *Comprehensive Heterocyclic Chemistry II: A Review of the Literature* 1982-1995, Elsevier Science, Inc., Tarrytown, N.Y. (1996); and references therein. The heterocyclo may optionally be substituted with at least one of F, Br, Cl or I or $CF_3$, alkyl, alkoxy, aryl, aryloxy, aryl(aryl) or diaryl, arylalkyl, arylalkyloxy, alkenyl, alkynyl, cycloalkyl, cycloalkenyl, cycloalkylalkyl, cycloalkylalkyloxy, hydroxy, hydroxyalkyl, acyl, alkanoyl, heteroaryl, heteroaryloxy, cycloheteroalkyl, arylheteroaryl, arylalkoxycarbonyl, heteroarylalkyl, heteroarylalkoxy, aryloxyalkyl, aryloxyaryl, alkylamido, alkanoylamino, arylcarbonylamino, nitro, cyano, thiol, haloalkyl, trihaloalkyl and/or alkylthio.

The term "alkanoyl" as used herein alone or as part of another group refers to alkyl linked to a carbonyl group.

The term "halogen" or "halo" as used herein alone or as part of another group refers to chlorine, bromine, fluorine, and iodine, with chlorine or fluorine being preferred.

The term "metal ion" refers to alkali metal ions such as sodium, potassium or lithium and alkaline earth metal ions such as magnesium and calcium, as well as zinc and aluminum.

The term "aryl" herein alone or as part of another group refers to monocyclic or bicyclic aromatic rings, e.g., phenyl, substituted phenyl and the like, as well as groups which are fused, e.g., naphthyl, phenanthrenyl and the like. An aryl group thus contains at least one ring having at least 6 atoms, with up to five such rings being present, containing up to 22 atoms therein, with alternating (resonating) double bonds between adjacent carbon atoms or suitable heteroatoms. Aryl groups may optionally be substituted with one or more groups including, but not limited to halogen, alkyl, alkenyl, cycloalkyl, heterocycloalkyl, alkoxy, haloalkoxy, haloalkyl, hydroxy, carboxy, carbamoyl, alkyloxycarbonyl, nitro, alkenyloxy, trifluoromethyl, amino, cycloalkyl, aryl, heteroaryl, cyano, alkyl $S(O)_m$ (m=0, 1, 2), or thiol and/or any of the alkyl substituents set out herein.

Unless otherwise indicated, the term "heteroaryl" as used herein alone or as part of another group refers to a 5- or 6-membered aromatic ring which includes 1, 2, 3 or 4 hetero atoms such as nitrogen, oxygen or sulfur. Such rings may be fused to an aryl, cycloalkyl, heteroaryl or heterocyclyl and include possible N-oxides as described in Katritzky, A. R. et al., eds. *Comprehensive Heterocyclic Chemistry: The Structure, Reactions, Synthesis and Uses of Heterocyclic Compounds*, Pergamon Press, New York, N.Y. (1984); and Katritzky, A. R. et al., eds., *Comprehensive Heterocyclic Chemistry II: A Review of the Literature* 1982-1995, Elsevier Science, Inc., Tarrytown, N.Y. (1996); and references therein.

Further, "heteroaryl", as defined herein, may optionally be substituted with one or more substituents such as the substituents included above in the definition of "substituted alkyl" and "substituted aryl". Examples of heteroaryl groups include the following:

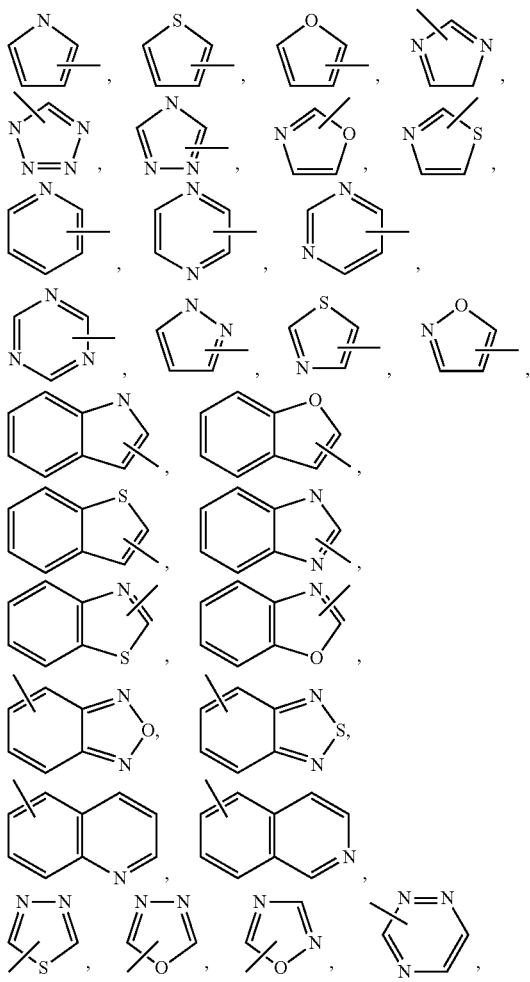

and the like.

Unless otherwise indicated, the term "lower alkoxy", "alkoxy", "aryloxy" or "aralkoxy" as employed herein alone or as part of another group includes any of the above alkyl, aralkyl or aryl groups linked to an oxygen atom.

Unless otherwise indicated, the term "lower alkylthio", alkylthio", "arylthio" or "aralkylthio" as employed herein alone or as part of another group includes any of the above alkyl, aralkyl or aryl groups linked to a sulfur atom.

The term "polyhaloalkyl" as used herein refers to an "alkyl" group as defined above which includes from 2 to 9, preferably from 2 to 5, halo substituents, such as F or Cl, preferably F, such as $CF_3CH_2$, $CF_3$ or $CF_3CF_2CH_2$.

The term "polyhaloalkyloxy" as used herein refers to an "alkoxy" or "alkyloxy" group as defined above which includes from 2 to 9, preferably from 2 to 5, halo substituents, such as F or Cl, preferably F, such as $CF_3CH_2O$, $CF_3O$ or $CF_3CF_2CH_2O$.

The term "acyl" as used herein alone or as part of another group refers to a radical linked to a carbonyl (C=O) group which radical can be, for example, lower alkyl, aryl, heterocyclo, heteroaryl, cycloalkyl, lower alkoxy or amino.

The term "cyclic amine" refers to a group having the formula

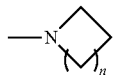

wherein n is 1, 2, or 3, that may contain further heteroatoms, such as O, N, or S. Preferred cyclic amine groups of the present invention include azetidinyl, pyrrolidyl, piperidyl, mopholinyl, thiomorpholinyl, and 1,1-dioxo-1-thiomorphilinyl.

Pharmaceutical Compositions

According to some embodiments of the present invention, pharmaceutical compositions are provided, comprising at least one compound having Formula I, as described herein, and at least one pharmaceutically acceptable diluent or carrier. The pharmaceutical compositions of the present invention, may optionally include at least one additional therapeutic agent selected from the group consisting of anti-obesity agents; anti-diabetic agents, appetite suppressants; cholesterol/lipid-lowering agents, and HDL-raising agents, as defined herein.

The present invention is also directed to pharmaceutical combinations, comprising at least one compound having the Formula I, and at least one additional therapeutic agent, selected from the group consisting of anti-obesity agents; anti-diabetic agents, appetite suppressants; cholesterol/lipid-lowering agents, and HDL-raising agents, as defined herein.

According to one embodiment of the present invention, the anti-diabetic agent is selected from the group consisting of insulin secretagogues, insulin sensitizers, glucokinase inhibitors, glucocorticoid antagonist, fructose 1,6-bis phosphatase inhibitors, AMP kinase activators, incretin modulators glucosidase inhibitors, aldose reductase inhibitors PPAR γ agonists, PPAR α agonists, PPAR δ antagonists or agonists, PPAR α/γ dual agonists, 11-β-HSD-1 inhibitors, dipeptidyl peptidase IV (DP4) inhibitors, SGLT2 inhibitors, insulin, glucagon-like peptide-1 (GLP-1), GLP-1 agonists, and PTP-1B inhibitors.

According to one embodiment of the present invention, the additional therapeutic agent is an antiobesity agent selected from group consisting of melanocortin receptor (MC4R) agonists, cannabinoid receptor modulators, growth hormone secretagogue receptor (GHSR) antagonists, galanin receptor modulators, orexin antagonists, CCK agonists, GLP-1 agonists, Pre-proglucagon-derived peptides; NPY1 or NPY5 antagonists; NPY2 and NPY4 modulators; orticotropin releasing factor agonists, histamine receptor-3 (H3) modulators, aP2 inhibitors, PPAR gamma modulators, PPAR delta modulators, acetyl-CoA carboxylase (ACC) inhibitors, 11-β-HSD-1 inhibitors, adinopectin receptor modulators; beta 3 adrenergic agonists, thyroid receptor beta modulators, lipase inhibitors, serotonin receptor agonists, monoamine reuptake inhibitors or releasing agents, anorectic agents, CNTF, BDNF, DGAT inhibitors, leptin, leptin receptor modulators, and cannabinoid-1 receptor inverse agonists/neutral antagonists.

Methods of Use

According to one embodiment of the present invention, methods are provided for treating obesity in a patient in need of such treatment, which includes the step of administering a therapeutically effective amount of at least one compound according to Formula I alone or in combination with one or more additional antiobesity agents, wherein the obesity agent is selected from those described herein.

According to one embodiment of the present invention, methods are provided for treating diabetes, especially Type II diabetes, in a patient in need of such treatment, which includes the step of administering a therapeutically effective amount of at least one compound according to Formula I alone or in combination with one or more additional antidiabetic agents, wherein the diabetic agent is described herein.

According to one embodiment of the present invention, methods for treating depression in a patient are provided, which includes the step of administering a therapeutically effective amount of at least one compound according to Formula I.

According to one embodiment of the present invention, methods are provided for treating anxiety in a patient in need of such treatment, which includes the step of administering a therapeutically effective amount of a compound having Formula I.

According to another embodiment of the present invention, methods are provided for treating intestinal inflammatory conditions, such as inflammatory bowel disease (IBD), colitis and Crohn's disease (CD) in a patient in need of such treatment which includes the step of administering a therapeutically effective amount of a compound of Formula I.

The assessment of activity of the compounds of Formula I of the invention in treating intestinal inflammation such as caused by inflammatory bowel disease, colitis and/or Crohn's disease, as described above, may be carried out employing the various assays as disclosed in Kokkotou, E. et al., "Melanin-concentrating hormone as a mediator of intestinal inflammation", *Proc. Natl. Acad. Sci.*, 105(30):10613-10618 (Jul. 29, 2008).

Utility

The compounds of the present invention can be administered to mammals, preferably humans, for the treatment of a variety of conditions and disorders, including, but not limited to metabolic and eating disorders as well as conditions associated with metabolic disorders (e.g., obesity, diabetes, arteriosclerosis, hypertension, polycystic ovary disease, cardiovascular disease, osteoarthritis, dermatological disorders, impaired glucose hemostasis, insulin resistance, hypercholesterolemia, hypertriglyceridemia, choletithiasis, dislipidemic conditions, bulimia nervosa and compulsive eating disorders); sleep disorders; and psychiatric disorders, such as depression, anxiety, schizophrenia, substance abuse, cognition-enhancement and Parkinson's disease; and inflammatory diseases such as inflammatory bowel disease, colitis and/or Crohn's disease.

The compounds described in the present invention could be used to enhance the effects of cognition-enhancing agents, such as acetylcholinesterase inhibitors (e.g., tacrine), muscarinic receptor-1 agonists (e.g., milameline), nicotinic agonists, glutamic acid receptor (AMPA and NMDA) modulators, and neurotropic agents (e.g., piracetam, levetiracetam). Examples of suitable therapies for treatment of Alzheimer's disease and cognitive disorders for use in combination with the compounds of the present invention include donepezil, tacrine, revastigraine, 5HT6, gamma secretase inhibitors, beta secretase inhibitors, SK channel blockers, Maxi-K blockers, and KCNQs blockers.

The compounds described in the present invention could be used to enhance the effects of agents used in the treatment of Parkinson's Disease. Examples of agents used to treat Parkinson's Disease include: levadopa with or without a COMT inhibitor, antiglutamatergic drugs (amantadine, riluzole), alpha-2 adrenergic antagonists such as idazoxan, opiate antagonists, such as naltrexone, other dopamine agonists or transporter modulators, such as ropinirole, or pramipexole or neurotrophic factors such as glial derived neurotrophic factor (GDNF).

Dosage Forms

The compounds of the present invention can be administered in oral dosage form. The dosage form for said pharmaceutical composition includes such oral dosage forms as granules, powders, tablets, capsules, syrups, emulsions, suspensions, etc. and such non-oral dosage forms as injections (e.g., subcutaneous, intravenous, intramuscular and intraperitoneal injections), drip infusions, external application forms (e.g., nasal spray preparations, transdermal preparations, ointments, etc.), and suppositories (e.g., rectal and vaginal suppositories).

These dosage forms can be manufactured by the per se known technique conventionally used in pharmaceutical procedures. The specific manufacturing procedures are as follows.

To manufacture an oral dosage form, an excipient (e.g., lactose, sucrose, starch, mannitol, etc.), a disintegrator (e.g., calcium carbonate, carboxymethylcellulose calcium, etc.), a binder (e.g., α-starch, gum arabic, carboxymethylcellulose, polyvinylpyrrolidone, hydroxypropylcellulose, etc.), and a lubricant (e.g., talc, magnesium stearate, polyethylene glycol 6000, etc.), for instance, are added to the active component or components and the resulting composition is compressed. Where necessary, the compressed product is coated, by the per se known technique, for masking the taste or for enteric dissolution or sustained release. The coating material that can be used includes, for instance, ethylcellulose, hydroxymethylcellulose, polyoxyethylene glycol, cellulose acetate phthalate, hydroxypropylmethylcellulose phthalate, and EUDRAGIT® (Rohm & Haas, Germany, methacrylic-acrylic copolymer).

Injections can be manufactured typically by the following procedure. The active component or components are dissolved, suspended or emulsified in an aqueous vehicle (e.g., distilled water, physiological saline, Ringer's solution, etc.) or an oily vehicle (e.g., vegetable oil such as olive oil, sesame oil, cottonseed oil, corn oil, etc. or propylene glycol) together with a dispersant, e.g., Tween 80 (Atlas Powder, U.S.A.), HCO 60 (Nikko Chemicals), polyethylene glycol, carboxymethylcellulose, sodium alginate, etc.), a preservative (e.g., methyl p-hydroxybenzoate, propyl p-hydroxybenzoate, benzyl alcohol, chlorobutanol, phenol, etc.), an isotonizing agent (e.g., sodium chloride, glycerol, sorbitol, glucose, inverted sugar, etc.) and other additives. If desired, a solubilizer (e.g., sodium salicylate, sodium acetate, etc.), a stabilizer (e.g., human serum albumin), a soothing agent (e.g., benzalkonium chloride, procaine hydrochloride, etc.) and other additives can also be added.

A dosage form for external application can be manufactured by processing the active component or components into a solid, semi-solid or liquid composition. To manufacture a solid composition, for instance, the active component or components, either as they are or in admixture with an excipient (e.g., lactose, mannitol, starch, microcrystalline cellulose, sucrose, etc.), a thickener (e.g., natural gums, cellulose derivatives, acrylic polymers, etc.), etc., are processed into powders. The liquid composition can be manufactured in substantially the same manner as the injections mentioned above. The semi-solid composition is preferably provided in a hydrous or oily gel form or an ointment form. These compositions may optionally contain a pH control agent (e.g., carbonic acid, phosphoric acid, citric acid, hydrochloric acid, sodium hydroxide, etc.), and a preservative (e.g., p-hydroxybenzoic acid esters, chlorobutanol, benzalkonium chloride, etc.), among other additives.

Suppositories can be manufactured by processing the active component or components into an oily or aqueous composition, whether solid, semi-solid or liquid. The oleaginous base that can be used includes, for instance, higher fatty acid glycerides [e.g., cacao butter, Witepsols (Dinamit-Nobel), etc.], medium-chain fatty acids [e.g., Migriols (Dinamit-Nobel), etc.], vegetable oils (e.g., sesame oil, soybean oil, cotton-seed oil, etc.), etc. The water-soluble base includes, for instance, polyethylene glycols propylene glycol, etc. The hydrophilic base includes, for instance, natural gums, cellulose derivatives, vinyl polymers, and acrylic polymers, etc.

Dosages

The dosage of the pharmaceutical composition of the present invention may be appropriately determined with reference to the dosages recommended for the respective active components and can be selected appropriately according to the recipient, the recipient's age and body weight, current clinical status, administration time, dosage form, method of administration, and combination of the active components, among other factors. For example, the dosage of the insulin sensitivity enhancer for an adult can be selected from the clinical oral dose range of 0.01 to 10 mg/kg body weight (preferably 0.05 to 10 mg/kg body weight, more preferably 0.05 to 5 mg/kg body weight) or the clinical parenteral dose range of 0.005 to 10 mg/kg body weight (preferably 0.01 to 10 mg/kg body weight, more preferably 0.01 to 1 mg/kg body weight). The other active component or components having different modes of action for use in combination can also be used in dose ranges selected by referring to the respective recommended clinical dose ranges.

The proportions of the active components in the pharmaceutical composition of the present invention can be appropriately selected according to the recipient, the recipient's age and body weight, current clinical status, administration time, dosage form, method of administration, and combination of active components, among other factors.

Pharmaceutical Combinations

The present invention includes within its scope pharmaceutical compositions includes, as an active ingredient, a therapeutically effective amount of at least one of the compounds of Formula I of the invention, alone or in combination with a pharmaceutical carrier or diluent. Optionally, compounds of the present invention can be used alone, in combination with other suitable therapeutic agents useful in the treatment of the aforementioned disorders including: anti-obesity agents; anti-diabetic agents, appetite suppressants; cholesterol/lipid-lowering agents, HDL-raising agents, cognition enhancing agents, agents used to treat neurodegeneration, agents used to treat respiratory conditions, agents used to treat bowel disorders, anti-inflammatory agents; anti-anxiety agents; anti-depressants; anti-hypertensive agents; cardiac glycosides; and anti-tumor agents.

The pharmaceutical combinations of the present invention can be formulated in combination, or separately by mixing the respective active components either together or independently with a physiologically acceptable carrier, excipient, binder, diluent, etc. When the active components are formulated independently, the respective formulations can be extemporaneously admixed using a diluent or the like and administered or can be administered independently of each other, either concurrently or at staggered times to the same subject. So, such other therapeutic agent(s) may be administered prior to, simultaneously with, or following the administration of the melanin-concentrating hormone receptor (MCHR) antagonists in accordance with the invention.

Examples of suitable anti-obesity agents for use in combination with the compounds of the present invention include melanocortin receptor (MC4R) agonists, cannabinoid receptor modulators, growth hormone secretagogue receptor (GHSR) antagonists, galanin receptor modulators, orexin antagonists, CCK agonists, GLP-1 agonists, and other Preproglucagon-derived peptides; NPY1 or NPY5 antagonist, NPY2 and NPY4 modulators, corticotropin releasing factor agonists, histamine receptor-3 (H3) modulators, aP2 inhibitors, PPAR gamma modulators, PPAR delta modulators, acetyl-CoA carboxylase (ACC) inhibitors, 11-β-HSD-1 inhibitors, adinopectin receptor modulators; beta 3 adrenergic agonists, such as AJ9677 (Takeda/Dainippon), L750355 (Merck), or CP331648 (Pfizer) or other known beta δ agonists as disclosed in U.S. Pat. Nos. 5,541,204, 5,770,615, 5,491, 134, 5,776,983 and 5,488,064, a thyroid receptor beta modulator, such as a thyroid receptor ligand as disclosed in WO 97/21993 (U. Cal SF), WO 99/00353 (KaroBio) and WO 00/039077 (KaroBio), a lipase inhibitor, such as orlistat or ATL-962 (Alizyme), serotonin receptor agonists, (e.g., BVT-933 (Biovitrum)), monoamine reuptake inhibitors or releasing agents, such as fenfluramine, dexfenfluramine, fluvoxamine, fluoxetine, paroxetine, sertraline, chlorphentermine, cloforex, clortermine, picilorex, sibutramine, dexamphetamine, phentermine, phenylpropanolamine or mazindol, anorectic agents such as topiramate (Johnson & Johnson), CNTF (ciliary neurotrophic factor)/AXOKINE® (Regeneron), BDNF (brain-derived neurotrophic factor), leptin and leptin receptor modulators, or cannabinoid-1 receptor inverse agonists/neutral antagonists, such as SR-141716 (Sanofi) or SLV-319 (Solvay) and DGAT inhibitors such as those described in WO 2006/134317 (A1) (Astra Zeneca), WO 2006/044775 (A2) (Bayer), WO 2006/06019020 (A1) (Sankyo), WO 2006/082010 (A1) (Roche), WO 2004/047755 (A2) (Japan Tobacco, Tularik), and WO 2005/0727401 (A2) (Amgen, Japan Tobacco).

Examples of suitable anti-diabetic agents for use in combination with the compounds of the present invention include: insulin secretagogues or insulin sensitizers, which may include biguanides, sulfonyl ureas, glucosidase inhibitors, aldose reductase inhibitors, PPAR γ agonists such as thiazolidinediones, PPAR α agonists (such as fibric acid derivatives), PPAR δ antagonists or agonists, PPAR α/γ dual agonists, 1'-β-HSD-1 inhibitors, dipeptidyl peptidase IV (DP4) inhibitors including saxagliptin, vildagliptin and sitagliptin, SGLT2 inhibitors including dapagliflozin and serglifozin, glycogen phosphorylase inhibitors, and/or meglitinides, as well as insulin, and/or glucagon-like peptide-1 (GLP-1), GLP-1 agonist, and/or a PTP-1B inhibitor (protein tyrosine phosphatase-1B inhibitor).

The antidiabetic agent may be an oral antihyperglycemic agent preferably a biguanide such as metformin or phenformin or salts thereof, preferably metformin HCl. Where the antidiabetic agent is a biguanide, the compounds of the present invention will be employed in a weight ratio to biguanide within the range from about 0.001:1 to about 10:1, preferably from about 0.01:1 to about 5:1.

The antidiabetic agent may also preferably be a sulfonyl urea such as glyburide (also known as glibenclamide), glimepiride (disclosed in U.S. Pat. No. 4,379,785), glipizide, gliclazide or chlorpropamide, other known sulfonylureas or other antihyperglycemic agents which act on the ATP-dependent channel of the beta-cells, with glyburide and glipizide being preferred, which may be administered in the same or in separate oral dosage forms. The oral antidiabetic agent may also be a glucosidase inhibitor such as acarbose (disclosed in U.S. Pat. No. 4,904,769) or miglitol (disclosed in U.S. Pat. No. 4,639,436), which may be administered in the same or in a separate oral dosage forms.

The compounds of the present invention may be employed in combination with a PPAR γ agonist such as a thiazolidinedione oral anti-diabetic agent or other insulin sensitizers (which has an insulin sensitivity effect in NIDDM patients) such as rosiglitazone (SKB), pioglitazone (Takeda), Mitsubishi's MCC-555 (disclosed in U.S. Pat. No. 5,594, 016), Glaxo-Wellcome's GL-262570, englitazone (CP-68722, Pfizer) or darglitazone (CP-86325, Pfizer, isaglitazone (MIT/J&J), JTT-501 (JPNT/P&U), L-895645 (Merck), R-119702 (Sankyo/WL), NN-2344 (Dr. Reddy/NN), or YM-440 (Yamanouchi), preferably rosiglitazone and pioglitazone.

The compounds of the present invention may be employed with a PPARα/γ dual agonist such as MK-767/KRP-297 (Merck/Kyorin; as described in Yajima, K. et al., *Am. J. Physiol. Endocrinol. Metab.*, 284:E966-E971 (2003)), AZ-242 (tesaglitazar; Astra-Zeneca; as described in Ljung, B. et al., *J. Lipid Res.*, 43:1855-1863 (2002)); muraglitazar; or the compounds described in U.S. Pat. No. 6,414,002.

The compounds of the present invention may be employed in combination with anti-hyperlipidemia agents, or agents used to treat arteriosclerosis. An example of an hypolipidemic agent would be an HMG CoA reductase inhibitor which includes, but is not limited to, mevastatin and related compounds as disclosed in U.S. Pat. No. 3,983,140, lovastatin (mevinolin) and related compounds as disclosed in U.S. Pat. No. 4,231,938, pravastatin and related compounds such as disclosed in U.S. Pat. No. 4,346,227, simvastatin and related compounds as disclosed in U.S. Pat. Nos. 4,448,784 and 4,450,171. Other HMG CoA reductase inhibitors which may be employed herein include, but are not limited to, fluvastatin, disclosed in U.S. Pat. No. 5,354,772, cerivastatin disclosed in U.S. Pat. Nos. 5,006,530 and 5,177,080, atorvastatin disclosed in U.S. Pat. Nos. 4,681,893, 5,273,995, 5,385,929 and 5,686,104, pitavastatin (Nissan/Sankyo's nisvastatin (NK-104) or itavastatin), disclosed in U.S. Pat. No. 5,011,930, Shionogi-Astra/Zeneca rosuvastatin (visastatin (ZD-4522)) disclosed in U.S. Pat. No. 5,260,440, and related statin compounds disclosed in U.S. Pat. No. 5,753,675, pyrazole analogs of mevalonolactone derivatives as disclosed in U.S. Pat. No. 4,613,610, indene analogs of mevalonolactone derivatives as disclosed in PCT application WO 86/03488, 6-[2-(substituted-pyrrol-1-yl)-alkyl)pyran-2-ones and derivatives thereof as disclosed in U.S. Pat. No. 4,647,576, Searle's SC-45355 (a 3-substituted pentanedioic acid derivative) dichloroacetate, imidazole analogs of mevalonolactone as disclosed in PCT application WO 86/07054, 3-carboxy-2-hydroxy-propane-phosphonic acid derivatives as disclosed in French Patent No. 2,596,393,2,3-disubstituted pyrrole, furan and thiophene derivatives as disclosed in European Patent Application No. 0221025, naphthyl analogs of mevalonolactone as disclosed in U.S. Pat. No. 4,686,237, octahydronaphthalenes such as disclosed in U.S. Pat. No. 4,499,289, keto analogs of mevinolin (lovastatin) as disclosed in European Patent Application No. 0142146A2, and quinoline and pyridine derivatives disclosed in U.S. Pat. Nos. 5,506,219 and 5,691,322. In addition, phosphinic acid compounds useful in inhibiting HMG CoA reductase suitable for use herein are disclosed in GB 2205837.

The squalene synthetase inhibitors suitable for use herein include, but are not limited to, α-phosphono-sulfonates disclosed in U.S. Pat. No. 5,712,396, those disclosed by Biller et al., *J. Med. Chem.*, 31:1869-1871 (1998) including isoprenoid (phosphinyl-methyl)phosphonates as well as other known squalene synthetase inhibitors, for example, as disclosed in U.S. Pat. Nos. 4,871,721 and 4,924,024 and in Biller, S. A. et al., *Current Pharmaceutical Design*, 2:1-40 (1996).

In addition, other squalene synthetase inhibitors suitable for use herein include the terpenoid pyrophosphates disclosed by Ortiz de Montellano, P. et al., *J. Med. Chem.*, 20:243-249 (1977), the farnesyl diphosphate analog A and presqualene pyrophosphate (PSQ-PP) analogs as disclosed by Corey et al., *J. Am. Chem. Soc.*, 98:1291-1293 (1976), phosphinylphosphonates reported by McClard, R. W. et al., *J. Am. Chem. Soc.*, 109:5544 (1987) and cyclopropanes reported by Capson, T. L., Ph.D. dissertation, June, 1987, Dept. Med. Chem. U of Utah, Abstract, Table of Contents, pp. 16, 17, 40-43, 48-51, Summary.

Other hypolipidemic agents suitable for use herein include, but are not limited to, fibric acid derivatives, such as fenofibrate, gemfibrozil, clofibrate, bezafibrate, ciprofibrate, clinofibrate and the like, probucol, and related compounds as disclosed in U.S. Pat. No. 3,674,836, probucol and gemfibrozil being preferred, bile acid sequestrants such as cholestyramine, colestipol and DEAE-Sephadex (SEC-HOLEX®, Policexide) and cholestagel (Sankyo/Geltex), as well as LIPOSTABIL® (Rhone-Poulenc), EISAI® E-5050 (an N-substituted ethanolamine derivative), imanixil (HOE-402), tetrahydrolipstatin (THL), istigmastanylphos-phorylcholine (SPC, Roche), aminocyclodextrin (Tanabe Seiyoku), Ajinomoto AJ-814 (azulene derivative), melinamide (Sumitomo), Sandoz 58-035, American Cyanamid CL-277,082 and CL-283,546 (disubstituted urea derivatives), nicotinic acid (niacin), acipimox, acifran, neomycin, p-aminosalicylic acid, aspirin, poly(diallylmethylamine) derivatives such as disclosed in U.S. Pat. No. 4,759,923, quaternary amine poly (diallyldimethylammonium chloride) and ionenes such as disclosed in U.S. Pat. No. 4,027,009, and other known serum cholesterol lowering agents.

The other hypolipidemic agent may be an ACAT inhibitor (which also has anti-atherosclerosis activity) such as disclosed in, *Drugs of the Future*, 24:9-15 (1999) (Avasimibe); Nicolosi et al., "The ACAT inhibitor, C1-1011 is effective in the prevention and regression of aortic fatty streak area in hamsters", Atherosclerosis (Shannon, Irel.), 137(1):77-85 (1998); Ghiselli, G., "The pharmacological profile of FCE 27677: a novel ACAT inhibitor with potent hypolipidemic activity mediated by selective suppression of the hepatic secretion of ApoB100-containing lipoprotein", *Cardiovasc. Drug Rev.*, 16(1):16-30 (1998); Smith, C. et al., "RP 73163: a bioavailable alkylsulfinyl-diphenylimidazole ACAT inhibitor", *Bioorg. Med. Chem. Lett.*, 6(1):47-50 (1996); Krause, B. R. et al., Chapter 6: "ACAT Inhibitors: Physiologic Mechanisms for Hypolipidemic and Anti-Atherosclerotic Activities in Experimental Animals", *Inflammation: Mediators and Pathways*, CRC Press, Inc., publ., Ruffolo, Jr., R. R. et al., eds., pp. 173-198 (1995); Sliskovic et al., "ACAT inhibitors: potential anti-atherosclerotic agents", *Curr. Med. Chem.*, 1(3):204-225 (1994); Stout et al., "Inhibitors of acyl-CoA: cholesterol O-acyl transferase (ACAT) as hypocholesterolemic agents. 6. The first water-soluble ACAT inhibitor with lipid-regulating activity. Inhibitors of acyl-CoA:cholesterol acyltransferase (ACAT). 7. Development of a series of substituted N-phenyl-N'-[(1-phenylcyclopentyl)-methyl]ureas with enhanced hypocholesterolemic activity", *Chemtracts: Org. Chem.*, 8(6):359-362 (1995), or TS-962 (Taisho Pharmaceutical Co. Ltd), as well as F-1394, CS-505, F-12511, HL-004, K-10085 and YIC-C8-434.

The hypolipidemic agent may be an upregulator of LDL receptor activity such as MD-700 (Taisho Pharmaceutical Co. Ltd) and LY295427 (Eli Lilly). The hypolipidemic agent may be a cholesterol absorption inhibitor preferably Schering-Plough's SCH48461 (ezetimibe) as well as those disclosed in *Atherosclerosis*, 115:45-63 (1995) and *J. Med. Chem.*, 41:973 (1998).

The other lipid agent or lipid-modulating agent may be a cholesteryl transfer protein inhibitor (CETP) such as Pfizer's CP-529,414 as well as those disclosed in WO 00/38722 and in EP 818448 (Bayer) and EP 992496, and Pharmacia's SC-744 and SC-795, as well as CETi-1 and JTT-705.

The hypolipidemic agent may be an ileal Na$^+$/bile acid cotransporter inhibitor such as disclosed in *Drugs of the Future*, 24:425-430 (1999). The ATP citrate lyase inhibitor which may be employed in the combination of the invention may include, for example, those disclosed in U.S. Pat. No. 5,447,954.

The other lipid agent also includes a phytoestrogen compound such as disclosed in WO 00/30665 including isolated soy bean protein, soy protein concentrate or soy flour as well as an isoflavone such as genistein, daidzein, glycitein or equol, or phytosterols, phytostanol or tocotrienol as disclosed in WO 2000/015201; a beta-lactam cholesterol absorption inhibitor such as disclosed in EP 675714; an HDL upregulator such as an LXR agonist, a PPAR α-agonist and/or an FXR agonist; an LDL catabolism promoter such as disclosed in EP 1022272; a sodium-proton exchange inhibitor such as disclosed in DE 19622222; an LDL-receptor inducer or a steroidal glycoside such as disclosed in U.S. Pat. No. 5,698,527 and GB 2304106; an anti-oxidant such as beta-carotene, ascorbic acid, α-tocopherol or retinol as disclosed in WO 94/15592 as well as Vitamin C and an antihomocysteine agent such as folic acid, a folate, Vitamin B6, Vitamin B 12 and Vitamin E; isoniazid as disclosed in WO 97/35576; a cholesterol absorption inhibitor, an HMG-CoA synthase inhibitor, or a lanosterol demethylase inhibitor as disclosed in WO 97/48701; a PPAR δ agonist for treating dyslipidemia; or a sterol regulating element binding protein-I (SREBP-1) as disclosed in WO 2000/050574, for example, a sphingolipid, such as ceramide, or neutral sphingomyelenase (N-SMase) or fragment thereof. Preferred hypolipidemic agents are pravastatin, lovastatin, simvastatin, atorvastatin, fluvastatin, pitavastatin, rosuvastatin, and ezetimibe as well as niacin and/or cholestagel.

The compounds of the present invention may be employed in combination with anti-hypertensive agents. Examples of suitable anti-hypertensive agents for use in combination with the compounds of the present invention include beta adrenergic blockers, calcium channel blockers (L-type and/or T-type; e.g., diltiazem, verapamil, nifedipine, amlodipine and mybefradil), diuretics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolactone), renin inhibitors, ACE inhibitors (e.g., captopril, zofenopril, fosinopril, enalapril, ceranopril, cilazopril, delapril, pentopril, quinapril, ramipril, lisinopril), AT-1 receptor antagonists (e.g., losartan, irbesartan, valsartan), ET receptor antagonists (e.g., sitaxsentan, atrsentan and compounds disclosed in U.S. Pat. Nos. 5,612,359 and 6,043, 265), Dual ET/A11 antagonist (e.g., compounds disclosed in WO 00/01389), neutral endopeptidase (NEP) inhibitors, vasopepsidase inhibitors (dual NEP-ACE inhibitors) (e.g., omapatrilat and gemopatrilat), and nitrates.

MCHR1 antagonists could be useful in treating other diseases associated with obesity, including sleep disorders. Therefore, the compounds described in accordance with the present invention could be used in combination with therapeutics for treating sleep disorders. Examples of suitable therapies for treatment of sleeping disorders for use in combination with the compounds of the present invention include melatonin analogs, melatonin receptor antagonists, ML 1 B agonists, GABA receptor modulators; NMDA receptor modulators, histamine-3 (H3) receptor modulators, dopamine agonists and orexin receptor modulators.

MCHR1 antagonists may reduce or ameliorate substance abuse or addictive disorders. Therefore, combination of cannabinoid receptor modulators with agents used to treat addictive disorders may reduce the dose requirement or improve the efficacy of current addictive disorder therapeutics. Examples of agents used to treat substance abuse or addictive disorders are: selective serotonin reuptake inhibitors (SSRI), methadone, buprenorphine, nicotine and bupropion.

MCHR1 antagonists may reduce anxiety or depression; therefore, the compounds described in accordance with the present invention may be used in combination with anti-anxiety agents or antidepressants. Examples of suitable anti-anxiety agents for use in combination with the compounds of the present invention include benzodiazepines (e.g., diazepam, lorazepam, oxazepam, alprazolam, chlordiazepoxide, clonazepam, chlorazepate, halazepam and prazepam), 5HT1A receptor agonists (e.g., buspirone, flesinoxan, gepirone and ipsapirone), and corticotropin releasing factor (CRF) antagonists.

Examples of suitable classes of anti-depressants for use in combination with the compounds of the present invention include norepinephrine reuptake inhibitors (tertiary and secondary amine tricyclics), selective serotonin reuptake inhibitors (SSRIs) (fluoxetine, fluvoxamine, paroxetine and sertraline), monoamine oxidase inhibitors (MAOIs) (isocarboxazid, phenelzine, tranylcypromine, selegiline), reversible inhibitors of monoamine oxidase (RIMAs) (moclobemide), serotonin and norepinephrine reuptake inhibitors (SNRIs) (venlafaxine), corticotropin releasing factor (CRF) receptor antagonists, alpha-adrenoreceptor antagonists, and atypical antidepressants (bupropion, lithium, nefazodone, trazodone and viloxazine).

The combination of a conventional antipsychotic drug with a MCHR1 antagonist could also enhance symptom reduction in the treatment of psychosis or mania. Further, such a combination could enable rapid symptom reduction, reducing the need for chronic treatment with antipsychotic agents. Such a combination could also reduce the effective antipsychotic dose requirement, resulting in reduced probability of developing the motor dysfunction typical of chronic antipsychotic treatment.

Examples of suitable antipsychotic agents for use in combination with the compounds of the present invention include the phenothiazine (chlorpromazine, mesoridazine, thioridazine, acetophenazine, fluphenazine, perphenazine and trifluoperazine), thioxanthine (chlorprothixene, thiothixene), heterocyclic dibenzazepine (clozapine, olanzepine and aripiprazole), butyrophenone (haloperidol), diphenylbutylpiperidine (pimozide) and indolone (molindolone) classes of antipsychotic agents. Other antipsychotic agents with potential therapeutic value in combination with the compounds in the present invention include loxapine, sulpiride and risperidone.

Combination of the compounds in the present invention with conventional antipsychotic drugs could also provide an enhanced therapeutic effect for the treatment of schizophrenic disorders, as described above for manic disorders. As used here, schizophrenic disorders include paranoid, disorganized, catatonic, undifferentiated and residual schizophrenia, schizophreniform disorder, schizoaffective disorder, delusional disorder, brief psychotic disorder and psychotic disorder not specified. Examples of suitable antipsychotic drugs for combination with the compounds in the present invention include the antipsychotics mentioned above, as well as dopamine receptor antagonists, muscarinic receptor agonists, 5HT2A receptor antagonists and 5HT2A/dopamine receptor antagonists or partial agonists (e.g., olanzepine, aripiprazole, risperidone, ziprasidone).

Methods of Preparation

The compounds of the present invention can be prepared in a number of ways well known to one skilled in the art of organic synthesis using the methods described below, together with synthetic methods known in the art of synthetic organic chemistry, or variations thereon as appreciated by those skilled in the art. Preferred methods include, but are not limited to, those described below. All references cited herein are hereby incorporated in their entirety by reference.

The novel compounds of Formula I may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including solvent, reaction atmosphere, reaction temperature, duration of the experiment and workup procedures, are chosen to be the conditions standard for that reaction, which should be readily recognized by one skilled in the art. One skilled in the art of organic synthesis understands that the functionality present on various portions of the edict molecule must be compatible with the reagents and reactions proposed. Not all compounds of Formula I falling into a given class may be compatible with some of the reaction conditions required in some of the methods described. Such restrictions to the substituents, which are compatible with the reaction conditions, will be readily apparent to one skilled in the art and alternate methods must be used.

Azolotriazinones can be prepared by one of two general routes shown in Schemes 1 and 2. As shown in Scheme 1, azole 1 can be converted to the bromoazole methyl ester 3 via bromination and treatment with NaOMe. Azole 1, where E=G=CH, is commercially available. Azole ester 3a, where E=N, G=CH, can be prepared as shown in Example 7A. Azole ester amine 4a, where E=CH and G=N, can prepared as described in Example 5A from 5-($R^1$)-2H-pyrazole-3-carboxylic acid ethyl ester (synthesized as reported by Wei et al., *Bioorg. Med. Chem. Leu.*, 16:6342-6347 (2006)).

Amination of 3 with a suitable aminating reagent such as chloramine affords amine 4 which upon treatment with DMF-dimethyl acetal yields amidine 5, which upon condensation with a primary amine 6 affords azolotriazinone 7. Examples of preparation of primary amines 6 are shown in Schemes 6A and 6B. In the case where compound 6 is defined as 6a with M, Q=$CR^3$, compound 6a is prepared via reaction of appropriate phenol 26 with either an alkyl halide or an appropriately substituted epoxide to yield nitro derivatives 29. Alternatively, when M, Q=$CR^3$ or N, intermediate 29 can be prepared via SNAr displacement of an aryl halide such as 30 with an appropriate alcohol or amine 30a in the presence of base. Reduction of intermediate 29 using methods commonly used in the literature, such as $H_2$/Pd—C or Sn/HCl, can provide amines 6a.

In the case when amines 6 are defined as 6a, an appropriately substituted cyclic amine 32 is reacted with haloarene or haloheteroarene 31 to afford compounds 33, which after reduction as indicated above, can yield amines 34.

Suzuki coupling of 7 with the appropriate boronic acid partner 8 gives the desired compound of invention I. Alternatively, the $R^1$ group can be installed at an earlier stage in the sequence starting from a bromoazole intermediate such as 2 or 3 to yield 3a and then following a similar sequence via N-amination of 3a to yield I. Compounds I can also be prepared via boron species such as 7a followed by Pd-catalyzed coupling to introduce the $R^1$ group.

As shown in Scheme 2, a similar sequence can be followed except that amine 9, where P is a group (such as benzyl, p-methoxybenzyl or allyl) that can be removed after the formation of the azolotriazinone ring, can be used in place of amine 6 (Scheme 1) to yield intermediate 10 which, after Suzuki coupling with boronic acid partner 8 and deprotection, affords the free azolotriazinone 11. Alternatively, 11 can be directly obtained from 4 via reaction with formamide followed by Suzuki coupling. Coupling with either a boronic acid 12 in the presence of a suitable catalyst (for example, Pd-, Cu-based) or a bromide 13 under Buchwald-coupling type conditions affords the desired compounds of invention I. A sequence similar to one shown from 3 to 11 in Scheme 2 can also be used to convert 3a to 11. Finally, in Schemes 1 and 2, $R^1$ group can be installed at any stage in the sequence starting from a suitable bromoazole intermediate.

Imidazolotriazinones IA of the invention, of the type shown in Scheme 3, were accessed via condensation of N-aminoimidazole esters such as 17 with enamines such as 18. The N-aminoimidazole ester 17 can be prepared by amination of 16 with a suitable aminating agent such as chloroamine. Compound 16 may be prepared as outlined in Scheme 3.

Scheme 4 depicts an alternative method of preparing compounds I via boron species such as 22. Intermediate 22 can be coupled with the appropriate aniline component 6 under standard conditions and then cyclized to afford compounds I.

Scheme 5 describes the synthesis of a phosphate prodrug (compound 24) of compounds I via a route that uses compound 23, which can be readily prepared from commercially available starting materials following a literature procedure (Chao, H.-G. et al., *J. Org. Chem.*, 59(22):6687-6691 (1994)). Thus, reaction of compounds I with bis(2-(trimethylsilyl)ethyl) diisopropylphosphoramidite, followed by oxidation with $H_2O_2$, can afford bis-trimethylsilylethyl-protected compounds 24. Deprotection using TFA can afford phosphate prodrugs 25. The phosphate esters can alternatively be prepared using other methods known in the literature. For example, dibenzyldiisopropylphosphoramidite or di-t-butyl-diisopropylphosphoramidite can be used in place of bis(2-(trimethylsilyl)ethyl) diisopropylphosphoramidite followed by oxidation and suitable deprotection protocols commonly used in the literature.

The amino acid prodrugs can be prepared using methods commonly described in the literature or as exemplified in this application.

Scheme 1
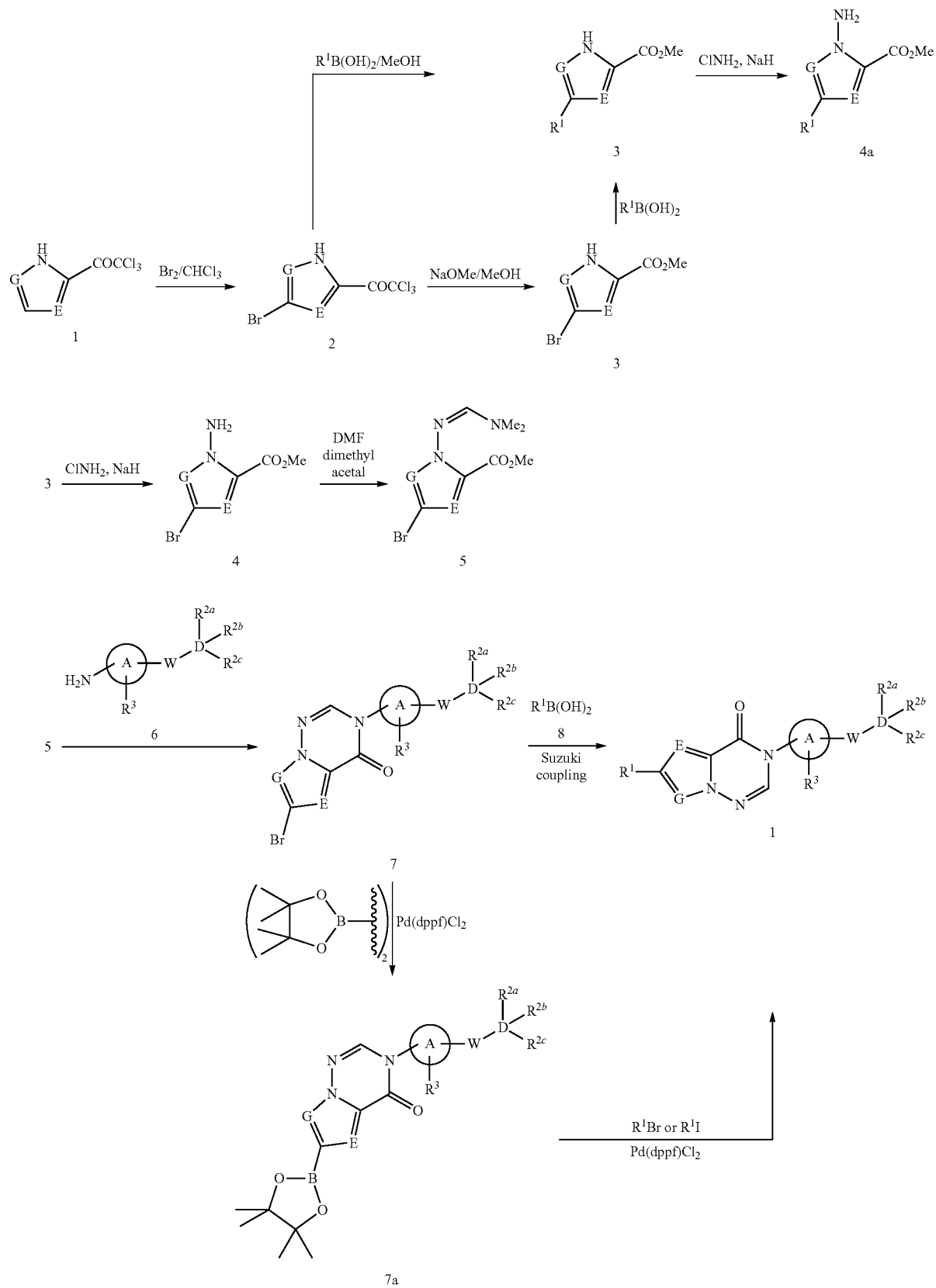

Scheme 2
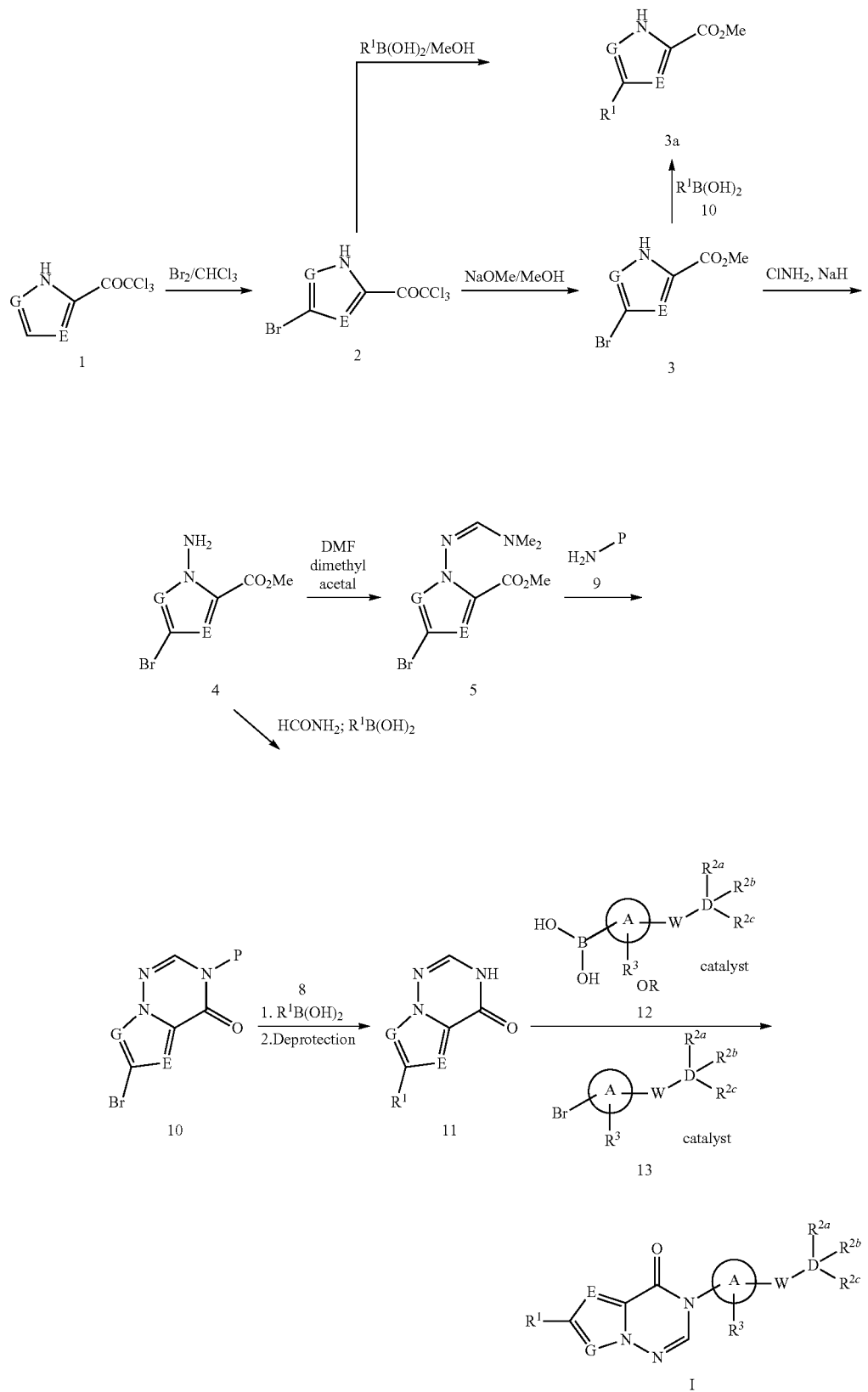

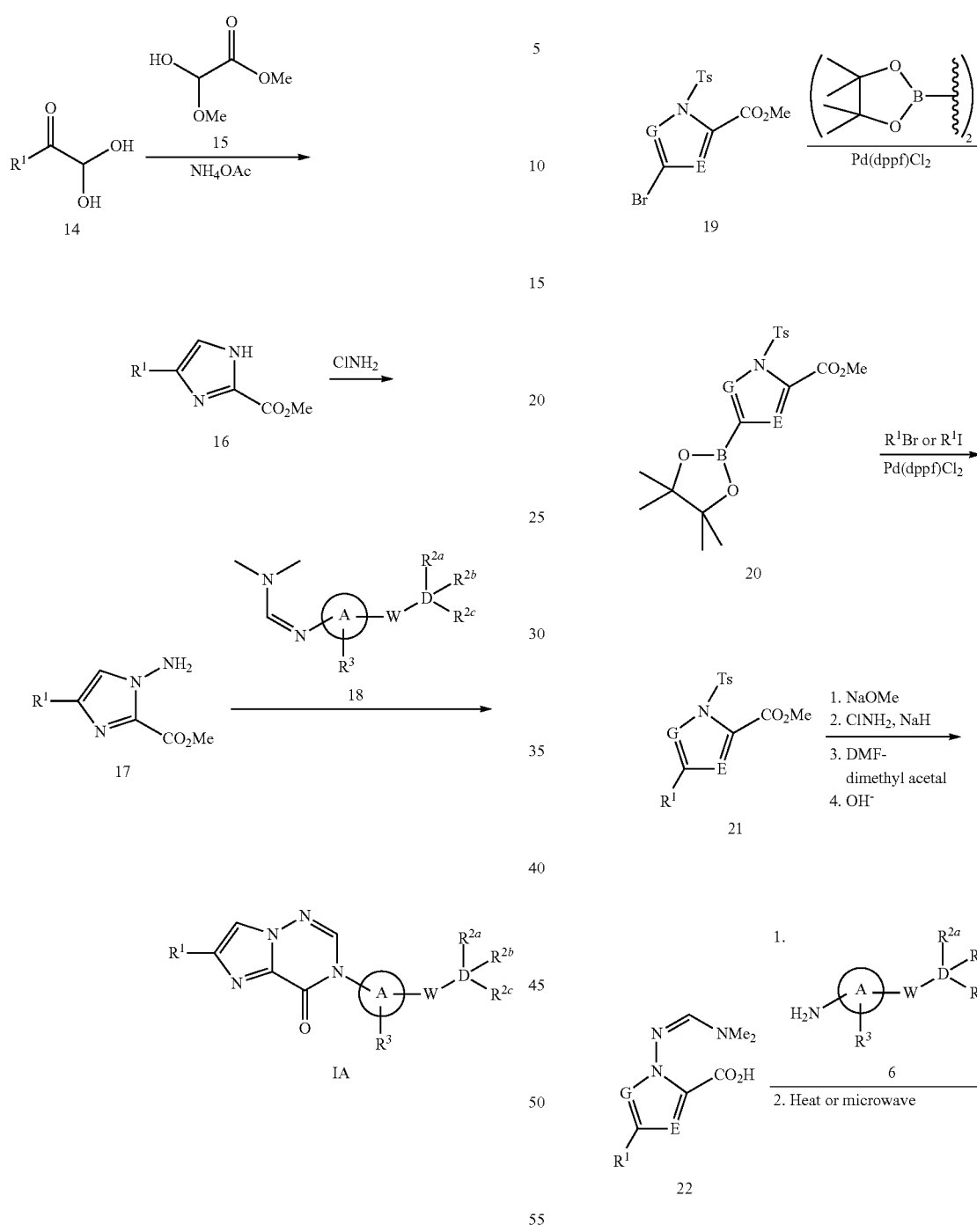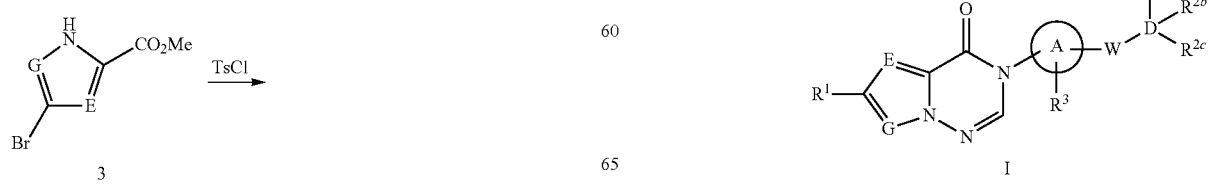

Scheme 5
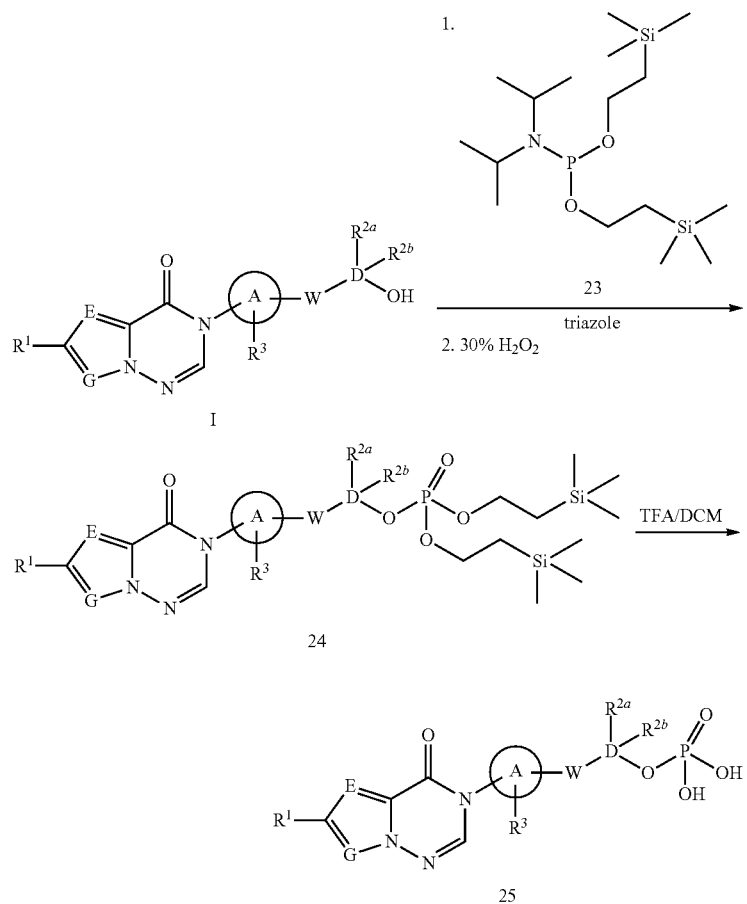
Scheme 6A
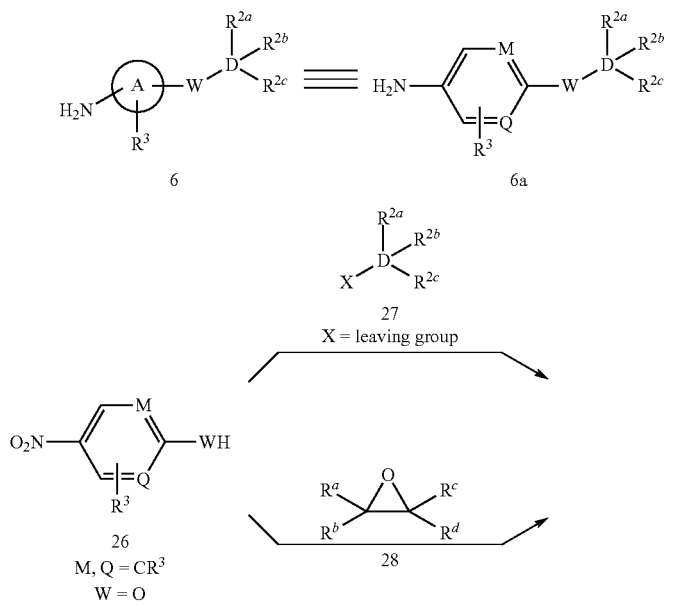

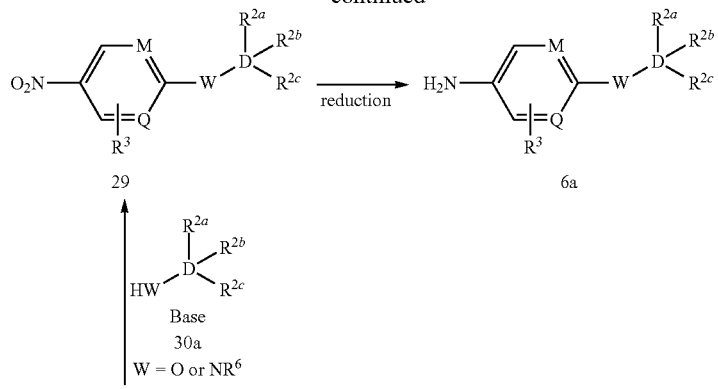
29

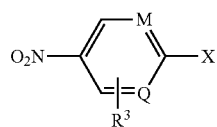
Base
30a
W = O or NR⁶

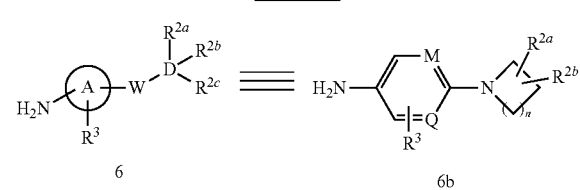
30
X = leaving group
M, Q = CR³ or N

Scheme 6B

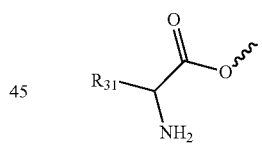

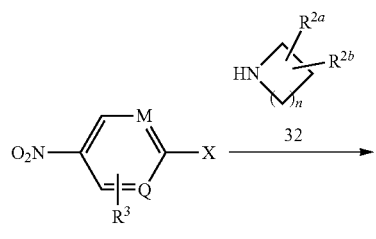
31
X = leaving group
M, Q = CR³ or N

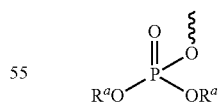
33

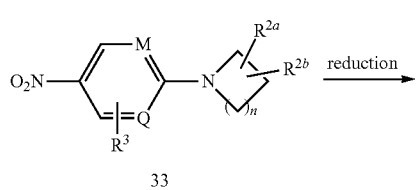
34

Prodrugs, Salts, Stereoisomers and Isotopes

The term "prodrug" encompasses both the term "prodrug esters" and the term "prodrug ethers". The term "prodrug esters" as employed herein includes esters and carbonates formed by reacting one or more hydroxyls of compounds of Formula I with either alkyl, alkoxy, or aryl substituted acylating agents or phosphorylating agent employing procedures known to those skilled in the art to generate acetates, pivalates, methylcarbonates, benzoates, amino acid esters, phosphates and the like. Preferred prodrugs include amino acid esters having the formula —OC(O)CH(NH₂)R³¹,

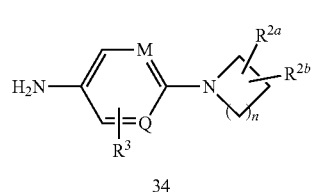

wherein $R^{31}$ is H or $C_1$ to $C_4$ alkyl, and phosphoric acid esters having the formula

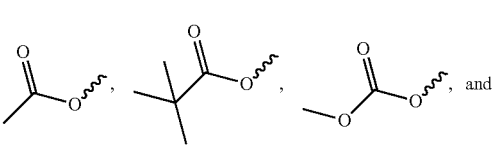

wherein $R^a$ is H. Additional examples of prodrug moieties of the present invention include

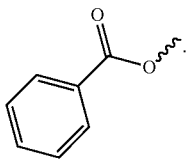

The term "prodrug ethers" include both phosphate acetals and O-glucosides. Representative examples of such prodrug ethers include

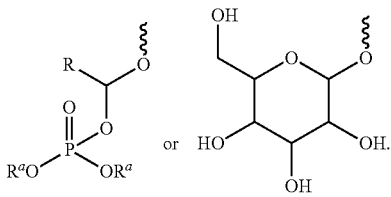

In the above formulae, R is alkyl or H and $R^a$ is H, alkyl, or benzyl.

The compounds of the present invention can be present as salts, which are also within the scope of this invention. Pharmaceutically acceptable (i.e., non-toxic, physiologically acceptable) salts are preferred. If the compounds of Formula I have, for example, at least one basic center, they can form acid addition salts. These are formed, for example, with strong inorganic acids, such as mineral acids, for example sulfuric acid, phosphoric acid or a hydrohalic acid, with organic carboxylic acids, such as alkanecarboxylic acids of 1 to 4 carbon atoms, for example acetic acid, which are unsubstituted or substituted, for example, by halogen as chloroacetic acid, such as saturated or unsaturated dicarboxylic acids, for example oxalic, malonic, succinic, maleic, fumaric, phthalic or terephthalic acid, such as hydroxycarboxylic acids, for example ascorbic, glycolic, lactic, malic, tartaric or citric acid, such as amino acids, (for example aspartic or glutamic acid or lysine or arginine), or benzoic acid, or with organic sulfonic acids, such as ($C_1$-$C_4$) alkyl or arylsulfonic acids which are unsubstituted or substituted, for example by halogen, for example methyl- or p-toluene-sulfonic acid. Corresponding acid addition salts can also be formed having, if desired, an additionally present basic center. The compounds of Formula I having at least one acid group (for example COOH) can also form salts with bases. Suitable salts with bases are, for example, metal salts, such as alkali metal or alkaline earth metal salts, for example sodium, potassium or magnesium salts, or salts with ammonia or an organic amine, such as morpholine, thiomorpholine, piperidine, pyrrolidine, a mono, di or tri-lower alkylamine, for example ethyl, tert-butyl, diethyl, diisopropyl, triethyl, tributyl or dimethyl-propylamine, or a mono, di or trihydroxy lower alkylamine, for example mono, di or triethanolamine. Corresponding internal salts may furthermore be formed. Salts which are unsuitable for pharmaceutical uses but which can be employed, for example, for the isolation or purification of free compounds of Formula I or their pharmaceutically acceptable salts, are also included.

Preferred salts of the compounds of Formula I which contain a basic group include monohydrochloride, hydrogensulfate, methanesulfonate, phosphate, nitrate or acetate.

Preferred salts of the compounds of Formula I which contain an acid group include sodium, potassium and magnesium salts and pharmaceutically acceptable organic amines All stereoisomers of the compound of the instant application are contemplated, either in admixture or in pure or substantially pure form. The compound of the present application can have asymmetric centers at any of the carbon atoms including any one of the R substituents. Consequently, compound of Formula I can exist in enantiomeric or diastereomeric forms or in mixtures thereof. The processes for preparation can utilize racemates, enantiomers or diastereomers as starting materials. When diastereomeric or enantiomeric products are prepared, they can be separated by conventional methods for example, chromatographic or fractional crystallization.

The present invention is intended to include all isotopes of atoms occurring in the present compounds of the invention. Isotopes include those atoms having the same atomic number but different mass numbers. By way of general example and without limitation, isotopes of hydrogen include deuterium and tritium. Isotopes of carbon include $^{13}$C and $^{14}$C. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

Abbreviations

The following abbreviations are employed herein:
Ph=phenyl
Bn=benzyl
t-Bu=tertiary butyl
Me=methyl
Et=ethyl
TMS=trimethylsilyl
TBS=tert-butyldimethylsilyl
THF=tetrahydrofuran
$Et_2O$=diethyl ether
EtOAc=ethyl acetate
DMF=dimethyl formamide
MeOH=methanol
EtOH=ethanol
i-PrOH=isopropanol
HOAc or AcOH=acetic acid
TFA=trifluoroacetic acid
i-$Pr_2$NEt=diisopropylethylamine
$Et_3$N=triethylamine
DMAP=4-dimethylaminopyridine
$NaBH_4$=sodium borohydride
n-BuLi=n-butyllithium
Pd/C=palladium on carbon
KOH=potassium hydroxide
NaOH=sodium hydroxide
LiOH=lithium hydroxide
$K_2CO_3$=potassium carbonate
$NaHCO_3$=sodium bicarbonate
Ar=argon
$N_2$=nitrogen
min=minute(s)
h or hr=hour(s)
L=liter
mL=milliliter
μL=microliter
g=gram(s)
mg=milligram(s)
mol=moles
mmol=millimole(s)
meq=milliequivalent
RT=room temperature sat or sat'd=saturated
aq.=aqueous
TLC=thin layer chromatography
HPLC=high performance liquid chromatography
LC/MS=high performance liquid chromatography/mass spectrometry
MS or Mass Spec=mass spectrometry
NMR=nuclear magnetic resonance
mp=melting point
HPLC-1: Sunfire C18 (4.6×150 mm) 3.5 micron, gradient 10 to 100% B:A for 12 min, then 3 min hold at 100% B.
Mobile phase A: 0.05% TFA in water: $CH_3CN$ (95:5)
Mobile phase B: 0.05% TFA in $CH_3CN$:water (95:5)
TFA Buffer pH=2.5; Flow rate: 1 mL/min; Wavelength: 254 nm, 220 nm.
HPLC-2: XBridge Phenyl (4.6×150 mm) 3.5 micron, gradient 10 to 100% B:A for 12 min, then 3 min hold at 100% B.
Mobile phase A: 0.05% TFA in water: $CH_3CN$ (95:5)
Mobile phase B: 0.05% TFA in $CH_3CN$:water (95:5)
TFA Buffer pH=2.5; Flow rate: 1 mL/min; Wavelength: 254 nm, 220 nm.

EXAMPLES

The following Examples serve to better illustrate, but not limit, some of the preferred embodiments of the invention.

Example 1

6-(4-Chlorophenyl)-3-(4-(2-hydroxy-2-methylpropoxy)-3-methoxyphenyl)pyrrolo[1,2-f][1,2,4]triazin-4(3H)-one

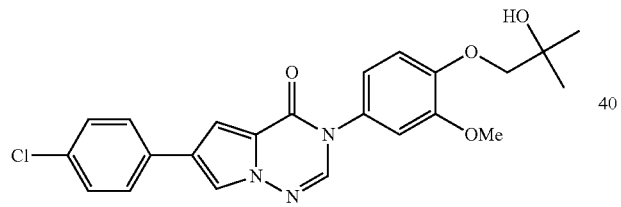

Example 1A

2-Trichloroacetylpyrrole

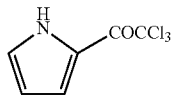

To trichloroacetyl chloride (48 mL; 0.43 mol) taken in anhydrous ether (150 mL) under nitrogen was added pyrrole (25 g, 0.37 mol) dissolved in anhydrous ether (500 mL) through a dropping funnel over a 2-hour period. The violet ether solution began to reflux during addition. Refluxing was continued for 1 h before the reaction was quenched with a solution of sodium carbonate (33 g, 0.31 mol) in water (200 mL). The layers were separated and the red organic layer was washed four times with water (4×50 mL) and once with brine (1×50 mL) and finally dried over anhydrous sodium sulphate. The red ether solution was then filtered through CELITE® and washed with ether. The solvent was removed under vacuum to afford 2-trichloroacetylpyrrole (Example 1A, 72 g, 91% yield).) as an ash colored solid (72 g, 91% yield). LC-MS, $[M-H]^+$=212. $^1H$ NMR (DMSO-$d_6$, 300 MHz): δ 9.63 (brs, 1H), 7.39 (m, 1H), 7.19 (m, 1H), 6.40 (m, 1H).

Example 1B

4-Bromo-2-trichloroacetylpyrrole

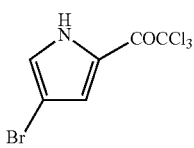

To a solution of Example 1A (21.2 g, 99 mmol) in $CHCl_3$ (100 mL), cooled in an ice-bath, bromine (17 g, 106 mmol) was added dropwise. The resulting solution was stirred at ambient temperature for 10 min and then poured into water. The organic phase was separated, washed with saturated aq. $NaHCO_3$ (50 mL) and water (50 mL), dried ($MgSO_4$) and evaporated under reduced pressure. Recrystallization of the residue from hexane gave the product 4-bromo-2-trichloroacetylpyrrole (Example 1B, 21 g, 73%) as an off-white solid. LC-MS, $[M-H]^+$=289. $^1H$ NMR (DMSO-$d_6$, 300 MHz): δ 12.9 (brs, 1H), 7.55 (s, 1H), 7.31 (s, 1H).

Example 1C

4-Bromo-2-methoxycarbonylpyrrole

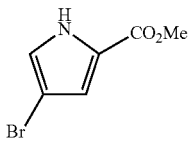

To a solution of Example 1B (20 g, 68 mmol) in methanol (100 mL), a solution of NaOMe (1M in MeOH, 34 mL, 34 mmol) was added slowly. This mixture was then stirred at ambient temperature for 1 h after which it was diluted with water (300 mL) and the organic layer was separated. The aqueous phase was extracted with $CH_2Cl_2$ and the combined organic layer and extracts were washed with water (2×50 mL), dried ($MgSO_4$) and evaporated under reduced pressure. Recrystallization of the residue from hexane gave 4-Bromo-2-methoxycarbonylpyrrole (Example 1C, 12 g, 85%) as a white solid. LC-MS, $[M-H]^+$=203. $^1H$ NMR (DMSO-$d_6$, 400 MHz): δ 12.31 (brs, 1H), 7.16 (s, 1H), 6.81 (s, 1H), 3.75 (s, 3H).

Example 1D

1-Amino-4-bromo-2-methoxycarbonylpyrrole

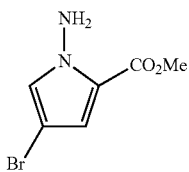

To a solution of 4-bromo-2-methoxycarbonylpyrrole (Example 1C, 1.8 g, 8.9 mmol) in 20 mL DMF was added NaH (0.34 g of 60% NaH) in three portions at 0° C. and then kept stirring at room temperature. After 1 h, chloramine solution in MTBE was added to the above reaction mass at 0° C. slowly and stirred for 4 h. After monitoring the progress of the reaction with LC-MS, the reaction was quenched with 50% sodium thiosulphate solution (50 mL) slowly and extracted with ethyl acetate extract (3×50 mL). Then the combined organic fractions were dried and concentrated to yield Example 1D (1.3 g, 67% yield) as a brown solid. LC-MS, [M+H]$^+$=219. $^1$H NMR (DMSO-d$_6$, 300 MHz): δ 7.19 (s, 1H), 6.75 (s, 1H), 6.34 (brs, 2H), 3.74 (s, 3H).

Chloramine synthesis: To 2 g of ammonium chloride taken in MTBE (75 mL) at −10° C. was added ammonium hydroxide (3.3 mL solution saturated with ammonia) and sodium hypochlorite (48 mL of 17% aqueous solution) slowly. The resultant mixture was stirred for 30 min at 0° C. Then MTBE layer was given brine wash (1×50 mL) and dried with anhydrous sodium sulphate at −40° C. for about 1 h.

Example 1E

4-Bromo-1-(dimethylamino-methyleneamino)-1H-pyrrole-2-carboxylic acid methyl ester

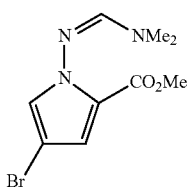

1-Amino-4-bromo-2-methoxycarbonylpyrrole (Example 1D, 1 g, 4.6 mmol) was taken in 20 volumes of DMF-dimethyl acetal and then kept stirred at 60° C. for 3 h. After monitoring the completion of the reaction with TLC, the solvent was evaporated under reduced pressure and the residue was purified through neutral alumina column (with dichloromethane as eluent) to yield the yellow-colored viscous enamine (Example 1E, 0.8 g, 64% yield). LC-MS, [M+H]$^+$=274. $^1$H NMR (DMSO-d$_6$, 400 MHz): δ 7.94 (s, 1H), 7.16 (s, 1H), 6.74 (s, 1H), 3.66 (s, 3H), 2.95 (s, 3H), 2.86 (s, 3H).

Example 1F 1-(4-Amino-2-methoxyphenoxy)-2-methylpropan-2-ol

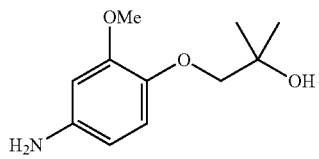

Example 1F was prepared as per application US 2007/0093509

Example 1G

6-Bromo-3-(4-(2-hydroxy-2-methylpropoxy)-3-methoxyphenyl)pyrrolo[1,2-f][1,2,4]triazin-4(3H)-one

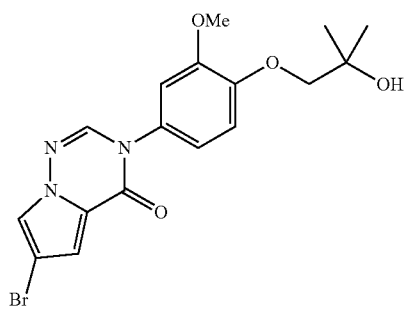 [SMILES: COc1cc(-n2cnn3cc(Br)cc3c2=O)ccc1OCC(C)(C)O]

To a solution of Example 1F (170 mg, 0.81 mmol) taken in acetonitrile and acetic acid (2:1) mixture, Example 1E (220 mg, 0.81 mmol) was added and the reaction mixture was heated up to 160° C. for 30 min under microwave irradiation. The reaction mass was concentrated to remove acetonitrile and acetic acid. Then the residue was diluted with ethyl acetate (30 mL), given water (30 mL) and brine washes (30 mL), and dried over Na$_2$SO$_4$. Concentration of organic layer followed by purification (60-120 mesh silica column, 0-10% ethyl acetate in pet ether) yielded Example 1G as an off-white solid (60 mg, 18% yield). LC-MS, [M+H]$^+$=408; [M+H−18]$^+$=390.

Example 1

6-(4-Chlorophenyl)-3-(4-(2-hydroxy-2-methylpropoxy)-3-methoxyphenyl)pyrrolo[1,2-f][1,2,4]triazin-4(3H)-one

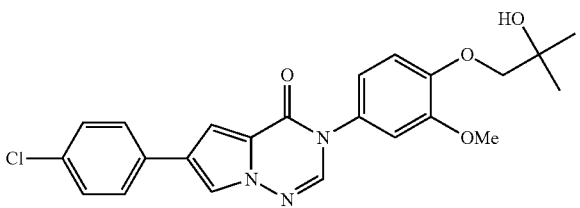 [SMILES: COc1cc(-n2cnn3cc(-c4ccc(Cl)cc4)cc3c2=O)ccc1OCC(C)(C)O]

A pressure tube with a screw cap was charged with bromo intermediate Example 1G (60 mg, 0.15 mmol), 4-chlorobenzene boronic acid (28 mg, 0.18 mmol), potassium carbonate (42 mg, 0.30 mmol), toluene (2 ml), water (1 ml) and tetra n-butyl ammonium hydroxide (0.05 mL, catalytic amount). This reaction mixture was purged with nitrogen for 15 min, and to it was added Pd(dppf)Cl$_2$ (13 mg, 10 mol %) under nitrogen and the mixture was again degassed. The reaction mass was heated up to 90° C. overnight. After confirmation of completion of reaction with TLC, toluene was removed under reduced pressure and the reaction mass was diluted with ethyl acetate (30 mL). Organic layer was given water (25 mL) and brine (25 mL) washes and dried over Na$_2$SO$_4$. The concentrate after purification (60-120 mesh silica column, 0-15% ethyl acetate in pet ether) yielded Example 1 as an off-white solid (15 mg, 24% yield). LC-MS, [M+H]$^+$=439. $^1$H NMR (DMSO-d$_6$, 400 MHz): δ 8.26 (d, J=1.9 Hz, 1H), 8.11 (s, 1H), 7.84 (d, J=8.4 Hz, 2H), 7.47 (d, J=1.9 Hz, 1H), 7.46 (d, J=8.4 Hz, 2H), 7.16 (d, J=2.4 Hz, 1H), 7.09 (d, J=8.6 Hz, 1H), 7.02 (dd, J=2.4, 8.5 Hz, 1H), 4.63 (s, 1H), 3.78 (s, 3H), 3.75 (s, 2H), 1.22 (s, 6H). HPLC-1: Purity=92.1%, Rt=11.474 min. HPLC-2: Purity=92.1%, Rt=10.525 min.

Example 2

6-(4-Chlorophenyl)-3-(3,4-dimethoxyphenyl)pyrrolo[1,2-f][1,2,4]triazin-4(3H)-one

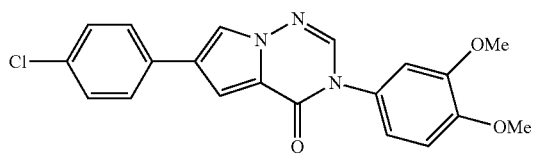 [SMILES: COc1ccc(-n2cnn3cc(-c4ccc(Cl)cc4)cc3c2=O)cc1OC]

Example 2A

6-Bromo-3-(3,4-dimethoxyphenyl)pyrrolo[1,2-f][1,2,4]triazin-4(3H)-one

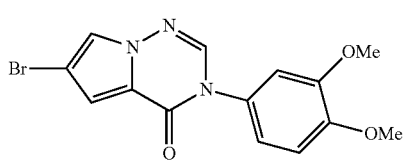 [SMILES: COc1ccc(-n2cnn3cc(Br)cc3c2=O)cc1OC]

Example 2A was prepared using a method analogous to Example 1G except that 3,4-dimethoxyaniline was used in place of Example 1F. LC-MS, [M+H]$^+$=350. $^1$H NMR (DMSO-d$_6$, 300 MHz): δ 8.13 (s, 1H), 7.92 (d, J=1.9 Hz, 1H), 7.15 (d, J=2.3 Hz, 1H), 7.09 (m, 2H), 7.03 (dd, J=2.3, 8.5 Hz, 1H), 3.81 (s, 3H), 3.75 (s, 3H).

Example 2

6-(4-Chlorophenyl)-3-(3,4-dimethoxyphenyl)pyrrolo[1,2-f][1,2,4]triazin-4(3H)-one Example 2 was prepared using a method analogous to Example 1 except that Example 1G was replaced by Example 2A. Yield=46%. LC-MS, [M+H]$^+$=382. $^1$H NMR (DMSO-d$_6$, 400 MHz): δ 8.26 (s, 1H), 8.12 (s, 1H), 7.84 (d, J=8.4 Hz, 2H), 7.47 (m, 3H), 7.16 (m, 1H), 7.10 (m, 2H), 3.81 (s, 3H), 3.77 (s, 3H). HPLC-1: Purity=96.9%, Rt=19.754 min and HPLC-2: Purity=96.6%, Rt=17.546 min.

Example 3

6-(4-Chlorophenyl)-3-(4-(2-cyclopropyl-2-hydroxyethoxy)-3-methoxyphenyl)pyrrolo[1,2-f][1,2,4]triazin-4(3H)-one

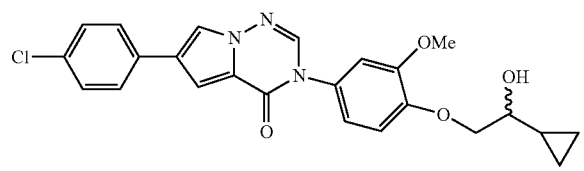 [SMILES: COc1cc(-n2cnn3cc(-c4ccc(Cl)cc4)cc3c2=O)ccc1OCC(O)C1CC1]

Example 3A 4-(2-(tert-Butyldimethylsilyloxy)-2-cyclopropylethoxy)-3-methoxyaniline

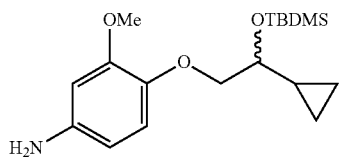 [SMILES: COc1cc(N)ccc1OCC(O[Si](C)(C)C(C)(C)C)C1CC1]

Example 3A was prepared by silylation of racemic 1-cyclopropyl-2-(2-methoxy-4-nitrophenoxy)ethanol (obtained during the synthesis of Example 48C), followed by reduction in the presence of H$_2$/Pd—C.

Example 3B

6-Bromo-3-(4-(2-(tert-butyldimethylsilyloxy)-2-cyclopropylethoxy)-3-methoxyphenyl)pyrrolo[1,2-f][1,2,4]triazin-4(3H)-one

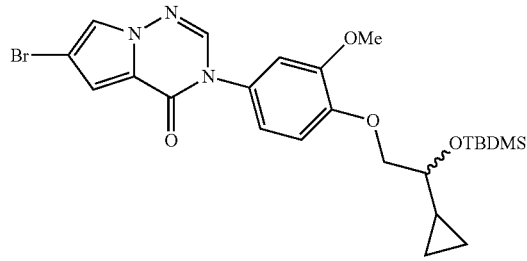 [SMILES: COc1cc(-n2cnn3cc(Br)cc3c2=O)ccc1OCC(O[Si](C)(C)C(C)(C)C)C1CC1]

Example 3A was prepared using a procedure analogous to Example 1G above except that Example IF was replaced by Example 3A. LC-MS, [M+H]$^+$=534. $^1$H NMR (DMSO-d$_6$, 300 MHz): δ 8.13 (s, 1H), 7.92 (d, J=1.7 Hz, 1H), 7.14 (d, J=2.1 Hz, 1H), 7.08 (d, J=1.4 Hz, 1H), 7.07 (d, J=8.28 Hz, 1H), 6.99 (dd, J=2.4, 8.3 Hz, 1H), 3.74 (m, 2H), 3.32 (s, 3H), 3.64 (m, 1H), 0.95 (m, 1H), 0.85 (s, 9H), 0.45 (m, 2H), 0.32 (m, 2H), 0.10 (s, 3H), 0.06 (s, 3H).

Example 3C 3-(4-(2-(tert-Butyldimethylsilyloxy)-2-cyclopropylethoxy)-3-methoxyphenyl)-6-(4-chlorophenyl)pyrrolo[1,2-f][1,2,4]triazin-4(3H)-one

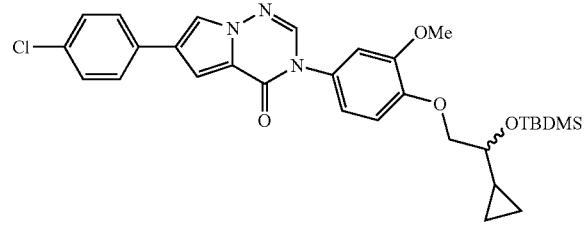 [SMILES: COc1cc(-n2cnn3cc(-c4ccc(Cl)cc4)cc3c2=O)ccc1OCC(O[Si](C)(C)C(C)(C)C)C1CC1]

Example 3C was prepared using a procedure analogous to Example 1 above except that Example 1G was replaced by Example 3B. LC-MS, [M+H]$^+$=566. $^1$H NMR (DMSO-d$_6$, 300 MHz): δ 8.25 (s, 1H), 8.12 (s, 1H), 7.84 (m, 2H), 7.45 (m, 3H), 7.16 (m, 1H), 7.06 (m, 1H), 7.01 (m, 1H), 4.01 (m, 2H), 3.76 (s, 3H), 3.60 (m, 1H), 0.95 (m, 1H), 0.86 (s, 9H), 0.45 (m, 2H), 0.33 (m, 2H), 0.11 (s, 3H), 0.07 (s, 3H).

Example 3

6-(4-Chlorophenyl)-3-(4-(2-cyclopropyl-2-hydroxyethoxy)-3-methoxyphenyl)pyrrolo[1,2-f][1,2,4]triazin-4(3H)-one

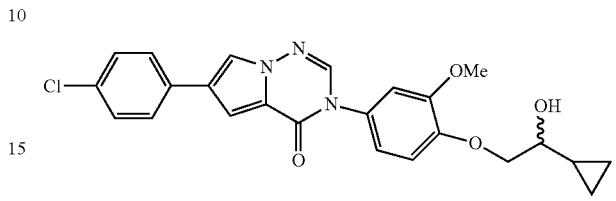

To Example 3C (35 mg, 0.06 mmol) taken in THF was added tetra n-butyl ammonium fluoride (0.12 mL, 0.12 mmol of 1 molar solution in THF) at room temperature and stirred for 3 h. After confirmation of reaction completion (with TLC), the reaction mass was concentrated and water was added to precipitate the target as a solid. The crude product was recrystallized from diethyl ether to yield Example 3 as an off-white solid (15 mg, 55% yield). LC-MS, [M+H]$^+$=452. $^1$H NMR (DMSO-d$_6$, 400 MHz): δ 8.28 (s, 1H), 8.13 (s, 1H), 7.85 (d, J=8.4 Hz, 2H), 7.48 (s, 1H), 7.46 (d, J=8.4 Hz, 2H), 7.17 (m, 1H), 7.12 (m, 1H), 7.03 (m, 1H), 4.90 (m, 1H), 4.03 (m, 2H), 3.78 (s, 3H), 3.29 (m, 1H), 0.97 (m, 1H), 0.42 (m, 2H), 0.33 (m, 2H). HPLC-1: Purity=92.1%, Rt=11.862 min. HPLC-2: Purity=92.7%, Rt=10.821 min.

Example 4

6-(4-Chlorophenyl)-3-(3-methoxy-4-(2-(pyrrolidin-1-yl)ethoxy)phenyl)pyrrolo[1,2-f][1,2,4]triazin-4(3H)-one

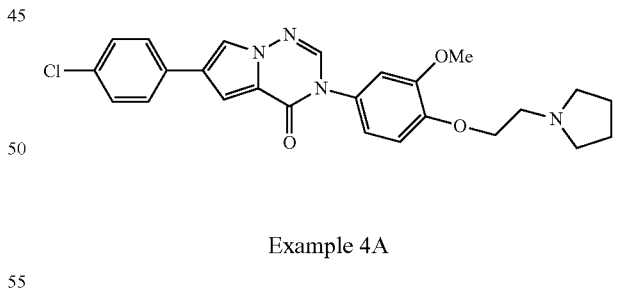

Example 4A

3-Methoxy-4-(2-(pyrrolidin-1-yl)ethoxy)aniline

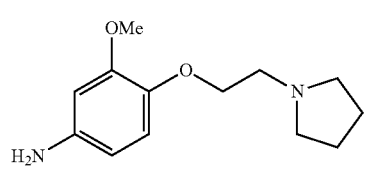 [SMILES: COc1cc(N)ccc1OCCN1CCCC1]

Example 4A was prepared following a procedure described in application WO 2002/101146.

Example 4B (Z)-Methyl 4-(4-chlorophenyl)-1-((dimethylamino)methyleneamino)-1H-pyrrole-2-carboxylate

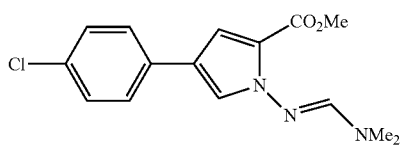 [SMILES: COC(=O)c1cc(-c2ccc(Cl)cc2)cn1/N=C/N(C)C]

Example 4B was prepared via Suzuki coupling of Example 1C with 4-chlorophenylboronic acid using conditions similar to those described in Example 1.

Example 4

6-(4-Chlorophenyl)-3-(3-methoxy-4-(2-(pyrrolidin-1-yl)ethoxy)phenyl)pyrrolo[1,2-f][1,2,4]triazin-4(3H)-one

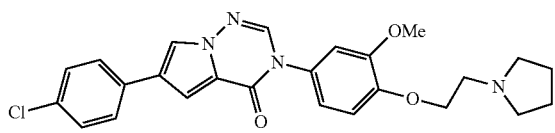 [SMILES: COc1cc(-n2cnn3cc(-c4ccc(Cl)cc4)cc3c2=O)ccc1OCCN1CCCC1]

To a solution of Example 4A (323 mg, 1.37 mmol) in acetonitrile and acetic acid (1:1) mixture (4 mL), Example 4B (350 mg, 1.15 mmol) was added and the reaction mixture was heated up to 120° C. for 60 min under microwave irradiation. The reaction mass was concentrated to remove acetonitrile and acetic acid. Then the residue was directly packed into a neutral alumina column and washed with methylene dichloride:methanol mixture (2% methanol). The crude product was purified by preparative HPLC column (XTERRA® C18, 19×300 mm, 10 micron, mobile phase A: 0.1% TFA in water; mobile phase B: CH₃CN, gradient from 10-40% B, flow rate: 15 mL/min; wavelength: 210 nm) to obtain pure Example 4 (10 mg, 2% yield) as an off-white solid. LC-MS, [M+H]$^+$=465. $^1$H NMR (DMSO-d$_6$, 400 MHz): δ 8.29 (s, 1H), 8.13 (s, 1H), 7.86 (d, J=8.8 Hz, 2H), 7.48 (m, 3H), 7.27 (d, J=2.4 Hz, 1H), 7.22 (d, J=8.4 Hz, 1H), 7.11 (dd, J=2.4, 8.4 Hz, 1H), 4.36 (m, 2H), 3.82 (s, 3H), 3.64 (m, 4H), 3.18 (m, 2H), 2.05 (m, 2H), 1.91 (m, 2H). HPLC-1: Purity=98%, Rt=7.9 min. HPLC-2: Purity=97%, Rt=9.7 min.

Example 5

6-(4-Chlorophenyl)-3-(3,4-dimethoxyphenyl)pyrazolo[1,5-f][1,2,4]triazin-4(3H)-one

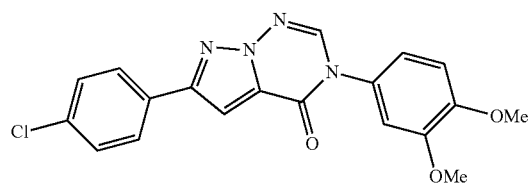 [SMILES: COc1ccc(-n2cnn3nc(-c4ccc(Cl)cc4)cc3c2=O)cc1OC]

Example 5A

2-Amino-5-(4-chlorophenyl)-2H-pyrazole-3-carboxylic acid ethyl ester

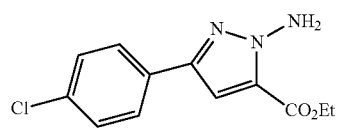 [SMILES: CCOC(=O)c1cc(-c2ccc(Cl)cc2)nn1N]

To a solution of 5-(4-chlorophenyl)-2H-pyrazole-3-carboxylic acid ethyl ester (synthesized as reported by Wei et al., Bioorg. Med. Chem. Leu., 16:6342-6347 (2006)) (2 g, 8 mmol) in 15 mL DMF was added NaH (0.446 g of 60% NaH) in three portions at 0° C. and then kept stirring at room temperature. After 1 h, chloramine solution in MTBE was added to the above reaction mass at 0° C. slowly and stirred for 4 h. The reaction was quenched with 50% sodium thiosulphate solution (60 mL) slowly and extracted with MTBE extract (3×50 mL). Then the combined organic fraction was dried and concentrated to yield Example 5A (2.0 g, 94% yield) as a yellow solid. LC-MS, [M+H]$^+$=266. $^1$H NMR (DMSO-d$_6$, 400 MHz): δ 7.85 (d, J=8.4 Hz, 2H), 7.47 (d, J=8.4 Hz, 2H), 7.27 (s, 1H), 7.06 (s, 2H), 4.35 (q, J=7.08 Hz, 2H), 1.34 (t, J=7.08 Hz, 3H).

Example 5B

Synthesis of 5-(4-chlorophenyl)-2-(dimethylaminomethyleneamino)-2H-pyrazole-3-carboxylic acid ethyl ester

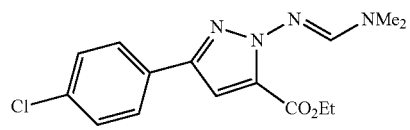 [SMILES: CCOC(=O)c1cc(-c2ccc(Cl)cc2)nn1/N=C/N(C)C]

1-Amino-4-(4-chlorophenyl)-1H-pyrrole-2-carboxylic acid methyl ester (Example 5A, 0.8 g, 3.0 mmol) was taken in DMF-dimethyl acetal (4 mL) and then stirred at 60° C. for 3 h. The solvent was evaporated under reduced pressure to yield Example 5B (0.75 g, 78% yield) as a yellow solid. LC-MS, [M+H]$^+$=306. $^1$H NMR (DMSO-d$_6$, 300 MHz): δ 8.40 (s, 1H), 7.87 (d, J=8.5 Hz, 2H), 7.46 (d, J=8.5 Hz, 2H), 7.29 (s, 1H), 4.26 (q, J=7.02 Hz, 2H), 3.04 (s, 3H), 2.87 (s, 3H), 1.31 (t, J=7.08 Hz, 3H).

Example 5

6-(4-Chlorophenyl)-3-(3,4-dimethoxyphenyl)pyrazolo[1,5-f][1,2,4]triazin-4(3H)-one

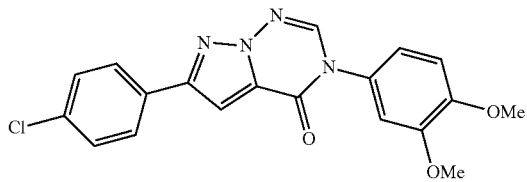 [SMILES: COc1ccc(-n2cnn3nc(-c4ccc(Cl)cc4)cc3c2=O)cc1OC]

To a solution of 3,4-dimethoxyaniline (0.14 g, 0.94 mmol) taken in acetonitrile and acetic acid (1:1) mixture (6 mL), Example 5B (0.3 g, 0.94 mmol) was added and the reaction mixture was heated up to 120° C. overnight. The reaction mass was quenched with water (30 mL), extracted with ethyl acetate (3×30 mL), dried and concentrated. Then the residue was packed into silica gel (60-120 mesh) column and eluted with ethyl acetate/hexane mixture (20 to 100% ethyl acetate). Thus product was re-purified by recrystallization (hexanes/ethyl acetate) to obtain pure Example 5 (20 mg, 6% yield) as a white solid. LC-MS, [M+H]$^+$=383. $^1$H NMR (DMSO-d$_6$, 400 MHz): δ 8.38 (s, 1H), 8.06 (dd, J=2.4, 8.4 Hz, 2H), 7.74 (s, 1H), 7.57 (dd, J=2.4, 8.8 Hz, 2H), 7.22 (d, J=2.0 Hz, 1H), 7.12 (m, 2H), 3.83 (s, 3H), 3.78 (s, 3H). $^{13}$C NMR (DMSO-d$_6$, 100 MHz): δ 153, 149, 148, 147, 142, 133, 131, 130, 129, 128, 127, 119, 112, 111, 101, 56. HPLC-1: Purity=98%, Rt=11.38 min. HPLC-2: Purity=97%, Rt=10.41 min.

Example 6

6-(4-Chlorophenyl)-3-(4-(2-(3-hydroxypyrrolidin-1-yl)ethoxy)-3-methoxyphenyl)pyrazolo[1,5-f][1,2,4]triazin-4(3H)-one

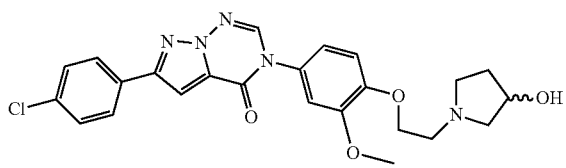 [SMILES: COc1cc(-n2cnn3nc(-c4ccc(Cl)cc4)cc3c2=O)ccc1OCCN1CCC(O)C1]

To a solution of 1-(2-(4-amino-2-methoxyphenoxy)ethyl)pyrrolidin-3-ol (0.35 g, 1.38 mmol) taken in acetonitrile and acetic acid (1:1) mixture (6 mL), Example 5B (0.445 g, 1.38 mmol) was added and the reaction mixture was heated up to 160° C. for 60 min under microwave irradiation. The reaction mixture was concentrated to remove acetonitrile and acetic acid. Then the residue was directly packed into silica gel (60-120 mesh) column and eluted with methylene dichloride: methanol mixture (4-5% methanol) to obtain pure Example 6 (50 mg, 7.5% yield) as an off-white solid. LC-MS, [M+H]$^+$=482. $^1$H NMR (DMSO-d$_6$, 400 MHz): δ 8.39 (s, 1H), 8.06 (d, J=8.4 Hz, 2H), 7.75 (s, 1H), 7.57 (d, J=8.4 Hz, 2H), 7.23 (s, 1H), 7.16 (d, J=8.8 Hz, 1H), 7.09 (d, J=8.4 Hz, 1H), 4.80 (brs, 1H), 4.20 (m, 1H), 4.14 (m, 2H), 3.78 (s, 3H), 2.87 (m, 2H), 1.99 (m, 2H), 1.60 (m, 2H). HPLC-1: Purity=95%, Rt=7.26 min. HPLC-2: Purity=96%, Rt=8.7 min.

Example 7

6-(4-Chlorophenyl)-3-(3-methoxy-4-(2-(pyrrolidin-1-yl)ethoxy)phenyl)imidazo[1,2-f][1,2,4]triazin-4(3H)-one

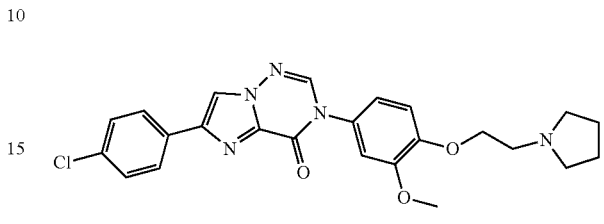

Example 7A 4-(4-Chlorophenyl)-1H-imidazole-2-carboxylic acid methyl ester

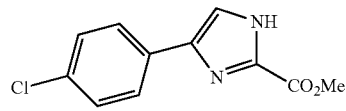 [SMILES: COC(=O)c1nc(-c2ccc(Cl)cc2)c[nH]1]

To a solution of ammonium acetate (1.36 g, 17.7 mmol) in water (5 mL) and acetonitrile (10 mL) at 0° C. was added methyl glyoxate (2.13 g, 17.7 mmol) followed by 1-(4-chlorophenyl)-2,2-dihydroxy-ethanone (1.1 g, 5.91 mmol) in acetonitrile (5 mL) over a period of 20 min at 0° C. The mixture was stirred at 0-5° C. for 30 min and at room temperature for overnight. After removal of acetonitrile the mixture was partitioned between ethyl acetate and water. The organic layer was washed with brine and dried over sodium sulfate, filtered and concentrated. The residue obtained was purified by recrystallization using (hexanes/ethyl acetate) to give the Example 7A (0.5 g, 34%) as a pale yellow solid. LC-MS, [M+H]$^+$=237. $^1$H NMR (DMSO-d$_6$, 400 MHz): δ 13.56 (brs, 1H), 7.97 (s, 1H), 7.88 (d, J=8.4 Hz, 2H), 7.45 (d, J=8.4 Hz, 2H), 3.87 (s, 3H).

Example 7B

1-Amino-4-(4-chlorophenyl)-1H-imidazole-2-carboxylic acid methyl ester

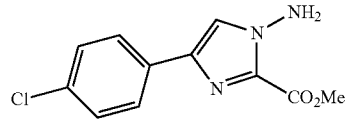 [SMILES: COC(=O)c1nc(-c2ccc(Cl)cc2)cn1N]

To a solution of 4-(4-chlorophenyl)-1H-imidazole-2-carboxylic acid methyl ester (Example 7A, 0.5 g, 2 mmol) in 10 mL DMF was added NaH (0.05 g of 60% NaH) at 0° C. and then stirred at room temperature. After 1 h, chloramine solution in MTBE was added to the above reaction mixture at 0° C. slowly and then stirred at room temperature for 4 h. After monitoring the progress of the reaction with LCMS, the reaction was quenched with 50% sodium thiosulphate solution (30 mL) slowly and extracted with MTBE extract (3×25 mL). Then the combined organic fraction was dried and concentrated to yield Example 7B (0.36 g, 72% yield) as a yellow solid. LC-MS, [M+H]⁺=252. ¹H NMR (DMSO-$d_6$, 400 MHz): δ 7.99 (s, 1H), 7.87 (d, J=8.4 Hz, 2H), 7.44 (d, J=8.4 Hz, 2H), 6.66 (brs, 2H), 3.85 (s, 3H).

Example 7C

N'-[3-Methoxy-4-(2-pyrrolidin-1-yl-ethoxy)-phenyl]-N,N-dimethyl-formamidine

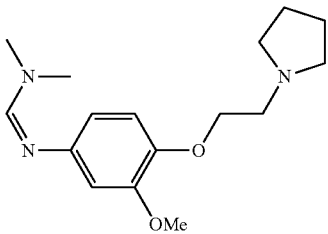 [SMILES: COc1cc(/N=C\N(C)C)ccc1OCCN1CCCC1]

3-Methoxy-4-(2-pyrrolidin-1-yl-ethoxy)-phenylamine (0.13 g, 0.55 mmol) was taken in DMF-dimethyl acetal (2 mL) and then stirred at 60° C. for 3 h. The solvent was evaporated under reduced pressure to obtain Example 7C (0.12 g, 75% yield) as a brown oil. LC-MS, [M+H]⁺=292. ¹H NMR (DMSO-$d_6$, 300 MHz): δ 7.66 (s, 1H), 6.79 (d, J=8.5 Hz, 1H), 6.53 (s, 1H), 6.38 (d, J=8.0 Hz, 1H), 3.95 (t, J=6.0 Hz, 2H), 3.72 (s, 3H), 2.93 (m, 6H), 2.74 (t, J=6.0 Hz, 2H), 2.40 (s, 2H), 1.66 (m, 6H).

Example 7

6-(4-Chlorophenyl)-3-(3-methoxy-4-(2-(pyrrolidin-1-yl)ethoxy)phenyl)imidazo[1,2-f][1,2,4]triazin-4(3H)-one

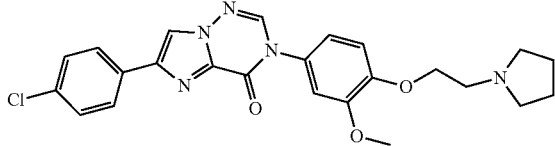 [SMILES: COc1cc(-n2cnn3cc(-c4ccc(Cl)cc4)nc3c2=O)ccc1OCCN1CCCC1]

To a solution of Example 7B (0.112 g, 0.45 mmol) taken in acetonitrile and acetic acid (1:1) mixture (4 mL), Example 7C (0.13 g, 0.45 mmol) was added and the reaction mixture was heated up to 160° C. for 60 min under microwave irradiation. The reaction mixture was concentrated to remove acetonitrile and acetic acid. Then the residue was directly packed into silica gel (60-120 mesh) column and eluted with methylene dichloride:methanol mixture (4-5% methanol) to obtain Example 7 (10 mg, 5% yield) as a brown solid. LC-MS, [M+H]⁺=466. ¹H NMR (DMSO-$d_6$, 400 MHz): δ 8.69 (s, 1H), 8.40 (s, 1H), 8.03 (d, J=8.4 Hz, 2H), 7.55 (d, J=8.4 Hz, 2H), 7.25 (m, 1H), 7.19 (d, J=8.4 Hz, 1H), 7.11 (dd, J=2.4, 8.8 Hz, 1H), 4.26 (brs, 2H), 3.79 (s, 3H), 3.00 (brs, 6H), 1.84 (brs, 4H). HPLC-1: Purity=90%, Rt=6.9 min. HPLC-2: Purity=89%, Rt=8.6 min.

Examples 8 to 14

The following examples were prepared in a manner analogous to Example 4.

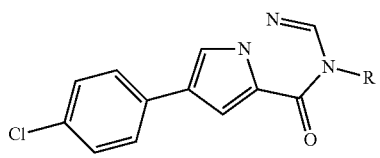

| Ex. No. | Name | R | LC-MS, [M + H]⁺ | ¹H NMR (DMSO-$d_6$, 400 MHz): δ | HPLC-1: Rt min, purity; HPLC-2: Rt min, purity | Synthesis Comments |
|---|---|---|---|---|---|---|
| 8 | N-(1-(5-(2-(4-Chlorophenyl)-6-oxopyrrolo[3,4-c]pyrazol-5(2H,4H,6H)-yl)pyridin-2-yl)pyrrolidin-3-yl)-N-methyl-acetamide | (structure: OMe-phenyl-N-pyrrolidinyl-OH) | 437 | 8.24 (s, 1H), 8.08 (s, 1H), 7.83 (d, J = 8.4 Hz, 2H), 7.44 (m, 3H), 7.04 (d, J = 2.04 Hz, 1H), 6.92 (d, J = 8.16 Hz, 1H), 6.69 (dd, J = 2.04, 8.16 Hz, 1H), 4.85 (d, J = 3.6 Hz, 1H), 4.32 (m, 1H), 3.75 (s, 3H), 3.62 (m, 1H), 3.46 (m, 1H), 3.27 (m, 1H), 3.13 (m, 1H), 1.99 (m, 1H), 1.81 (m, 1H). | 8.57, 95%; 10.0, 95% | Via OTBS-protected aniline. |

-continued

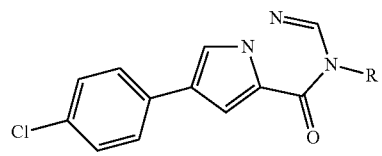

| Ex. No. | Name | R | LC-MS, [M + H]+ | 1H NMR (DMSO-d6, 400 MHz): δ | HPLC-1: Rt min, purity; HPLC-2: Rt min, purity | Synthesis Comments |
|---|---|---|---|---|---|---|
| 9 | 6-(4-Chloro-phenyl)-3-(3-methoxy-4-pyrrolidin-1-ylphenyl) pyrrolo [2,1-f][1,2,4] triazin-4(3H)-one | 3-methoxy-4-(pyrrolidin-1-yl)phenyl | 421 | 8.25 (s, 1H), 8.09 (s, 1H), 7.83 (d, J = 8.4 Hz, 2H), 7.45 (m, 3H), 7.05 (d, J = 2.0 Hz, 1H), 6.93 (d, J = 8.0 Hz, 1H), 6.69 (dd, J = 2.0, 8.0 Hz, 1H), 3.75 (s, 3H), 3.32 (m, 4H), 1.87 (m, 4H). | 9.4; 95% 8.5; 95% | |
| 10 | 6-(4-Chloro-phenyl)-3-(6-(3-(methyl-amino)pyrrolidin-1-yl)pyridin-3-yl)pyrrolo[1,2-f][1,2,4]triazin-4(3H)-one | 6-(3-(methylamino)pyrrolidin-1-yl)pyridin-3-yl | 421 | 8.26 (s, 1H), 8.14 (d, J = 2.4 Hz, 1H), 8.10 (s, 1H), 7.84 (d, J = 8.4 Hz, 2H), 7.62 (dd, J = 2.4, 8.8 Hz, 1H), 7.47 (m, 3H), 6.55 (d, J = 8.8 Hz, 1H), 3.59 (m, 1H), 3.52 (m, 1H), 3.43 (m, 2H), 3.24 (m, 2H), 2.33 (s, 3H), 2.11 (m, 1H), 1.85 (m, 1H). | 6.89, 97%; 8.06, 96% | See foot-note 1. |
| 11 | 6-(4-Chloro-phenyl)-3-{4-[2-(3-hydroxy-pyrrolidin-1-yl)-ethoxy]-3-methoxy-phenyl}-3H-pyrrolo[2,1-f][1,2,4] triazin-4-one | 4-[2-(3-hydroxypyrrolidin-1-yl)ethoxy]-3-methoxyphenyl | 481 | 8.25 (s, 1H), 8.12 (s, 1H), 7.84 (d, J = 8.4 Hz, 2H), 7.46 (m, 3H), 7.18 (d, J = 1.9 Hz, 1H), 7.12 (d, J = 8.6 Hz, 1H), 7.04 (dd, J = 1.9, 8.6 Hz, 1H), 4.84 (br s, 1H), 4.22 (s, 1H), 4.15 (t, J = 5.3 Hz, 2H), 3.90 (s, 3H), 2.92 (m, 3H), 2.81 (m, 1H), 2.66 (m, 1H), 2.57 (m, 1H), 2.05 (m, 1H), 1.59 (m, 1H). | 7.59, 95%; 8.57, 94% | Aniline prepared according to WO 2007/11286. |
| 12 | 3-{4-[2-(2-Aza-bicyclo[2.2.1]hept-2-yl)-ethoxy]-3-methoxy-phenyl}-6-(4-chloro-phenyl)-3H-pyrrolo[2,1-f][1,2,4]triazin-4-one, HCl | 4-[2-(2-azabicyclo[2.2.1]hept-2-yl)ethoxy]-3-methoxyphenyl | 491 | 9.9 (br s, 1H), 8.28 (s, 1H), 8.13 (s, 1H), 7.85 (d, J = 8.4 Hz, 2H), 7.48 (m, 3H), 7.26 (d, J = 2.4 Hz, 1H), 7.20 (d, J = 8.8 Hz, 1H), 7.10 (dd, J = 2.4, 8.8 Hz, 1H), 4.43 (t, J = 4.8 Hz, 2H), 4.39 (m, 1H), 3.81 (s, 3H), 3.37 (m, 1H), 3.16 (m, 1H), 2.81 (m, 1H), 2.66 (m, 1H), 2.08 (m, 2H), 1.76 (m, 4H), 1.41 (m, 1H). | 7.98, 96%; 9.40, 95% | Using Example 12A. |
| 13 | 6-(4-Chloro-phenyl)-3-[3-methoxy-4-(2-pyrrolidin-1-yl-propoxy)-phenyl]-3H-pyrrolo[2,1-f][1,2,4]triazin-4-one | 3-methoxy-4-(2-pyrrolidin-1-ylpropoxy)phenyl | 479 | 8.28 (s, 1H), 8.13 (s, 1H), 7.84 (d, J = 8.6 Hz, 2H), 7.48 (m, 3H), 7.25 (d, J = 2.4 Hz, 1H), 7.21 (d, J = 8.6 Hz, 1H), 7.09 (dd, J = 2.4, 8.6 Hz, 1H), 4.32 (d, J = 4.7 Hz, 2H), 3.80 (m, 4H), 3.57 (m, 2H), 3.26 (m, 2H), 2.00 (m, 2H), 1.97 (m, 2H), 1.4 (s, 3H). | 8.02, 97%; 9.30, 96% | Aniline preparation as in Example 12. |

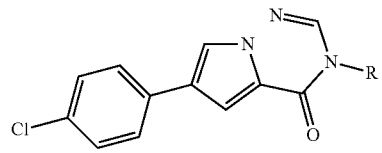

| Ex. No. | Name | R | LC-MS, [M + H]+ | 1H NMR (DMSO-d6, 400 MHz): δ | HPLC-1: Rt min, purity; HPLC-2: Rt min, purity | Synthesis Comments |
|---|---|---|---|---|---|---|
| 14 | 6-(4-Chloro-phenyl)-3-[3-methoxy-4-(2-methyl-2-pyrrolidin-1-yl-propoxy)-phenyl]-3H-pyrrolo[2,1-f][1,2,4]triazin-4-one | | 493 | 8.28 (s, 1H), 8.13 (s, 1H), 7.85 (d, J = 8.4 Hz, 2H), 7.48 (m, 3H), 7.27 (m, 2H), 7.13 (m, 1H), 4.21 (s, 2H), 3.82 (s, 3H), 3.41 (m, 4H), 1.91 (m, 4H), 1.40 (s, 6H). | 7.99, 97%; 9.55, 96% | Aniline preparation as in Example 12. |

[1] Via tert-butyl 1-(5-aminopyridin-2-yl)pyrrolidin-3-yl(methyl)carbamate, made by a method adapted from *Bioorganic & Medicinal Chemistry Letters*; 15(16): 3701-3706 (2005).

Example 12A 4-(2-(2-Azabicyclo[2.2.1]heptan-2-yl)ethoxy)-3-methoxyaniline

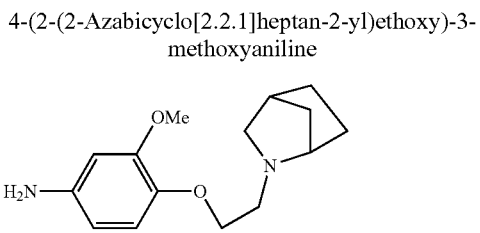

In 20 mL of dry dimethyl formamide, 2-(2-azabicyclo[2.2.1]heptan-2-yl)ethanol (0.5 g, 3.5 mmol) was added followed by sodium hydride at 0° C. After 1 h, 1-chloro-2-methoxy-4-nitrobenzene dissolved in DMF was added to the reaction mass and stirred overnight. Then DMF was removed under vacuum, added water and extracted with dichloromethane. The concentrate was purified by silica gel column (60-120 mesh) using 5-6% methanol in chloroform as eluent. Thus obtained nitro compound (0.27 g) was reduced in ethanol using Pd/C to yield Example 12A (0.2 g, 83%).

Example 15

2-(4-(6-(4-Chlorophenyl)-4-oxopyrrolo[1,2-f][1,2,4]triazin-3(4H)-yl)-2-methoxyphenoxy)-1-cyclopropylethyl 2-amino-3-methylbutanoate, HCl

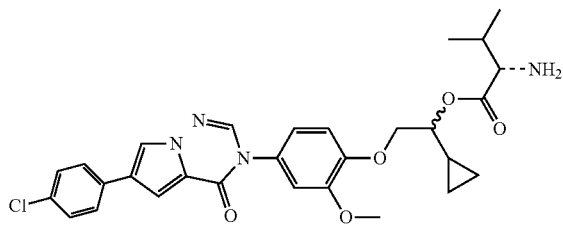 [SMILES: COc1cc(N(C=N)C(=O)c2cc(-c3ccc(Cl)cc3)c[nH]2)ccc1OCC(OC(=O)[C@@H](N)C(C)C)C1CC1]

Example 15 was prepared from Example 3 following a procedure similar to the one described in U.S. Publication No. 2009/0011994 (A1). LC-MS, [M+H]+=551. 1H NMR (DMSO-d6, 400 MHz): δ 8.40 (m, 3H), 8.26 (s, 1H), 8.11 (s, 1H), 7.84 (d, J=8.44 Hz, 2H), 7.46 (m, 3H), 7.20 (m, 2H), 7.05 (m, 1H), 4.70 (m, 1H), 4.28 (m, 2H), 4.11 (m, 1H), 3.77 (s, 3H), 3.10 (m, 1H), 2.30 (m, 1H), 1.09 (m, 6H), 0.61 (m, 4H). HPLC-1: Purity=98%, Rt=8.29 min. HPLC-2: Purity=99%, Rt=14.3 min.

Example 16

(1-{5-[6-(4-Chlorophenyl)-4-oxo-4H-pyrrolo[2,1-f][1,2,4]triazin-3-yl]-pyridin-2-yl}-pyrrolidin-3-yl)-methyl-carbamic acid methyl ester

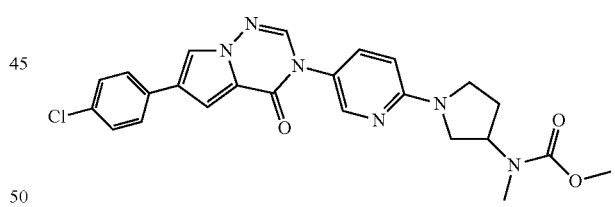

To a solution of Example 10 in dichloromethane (0.05 g in 2 mL) was added triethylamine (0.033 mL, 2 equiv.) and then methyl chloroformate (0.02 mL, 1.5 equiv.). After 3 h stirring at room temperature, the reaction mass was diluted with dichloromethane (10 mL), washed with water (10 mL) and then concentrated. The concentrate was recrystallized with acetonitrile to yield Example 16 (0.02 g, 25% yield). LC-MS, [M+H]+=479. 1H NMR (DMSO-d6, 400 MHz): δ 8.27 (s, 1H), 8.18 (d, J=2.4 Hz, 1H), 8.12 (s, 1H), 7.85 (d, J=8.4 Hz, 2H), 7.66 (dd, J=2.4, 8.4 Hz, 1H), 7.48 (m, 3H), 6.61 (d, J=8.8 Hz, 1H), 4.81 (br s, 1H), 3.65 (m, 5H), 3.45 (m, 2H), 2.81 (s, 3H), 2.16 (m, 2H). HPLC-1: Purity=96%, Rt=9.24 min. HPLC-2: Purity=96%, Rt=9.4 min.

Example 17

6-(4-Chlorophenyl)-3-(2-pyrrolidin-1-yl-pyrimidin-5-yl)-3H-pyrrolo[2,1-f][1,2,4]triazin-4-one, HCl

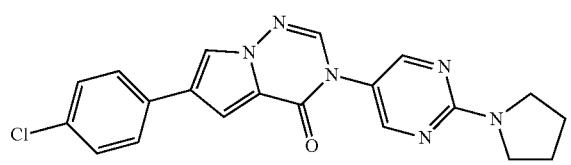 [SMILES: O=c1c2cc(-c3ccc(Cl)cc3)cn2ncn1-c1cnc(N2CCCC2)nc1]

Example 17A

Methyl 1-amino-4-(4-chlorophenyl)-1H-pyrrole-2-carboxylate

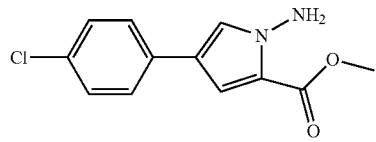 [SMILES: COC(=O)c1cc(-c2ccc(Cl)cc2)cn1N]

To a solution of methyl 4-(4-chlorophenyl)-1H-pyrrole-2-carboxylate (0.8 g, 3.4 mmol) in 10 mL DMF was added NaH (0.16 g of 60% NaH) in three portions at 0° C. and then kept stirring at room temperature. After 1 h, chloramine solution in MTBE was added to the above reaction mass at 0° C. slowly and stirred for 4 h. The reaction was quenched with 50% sodium thiosulphate solution (40 mL) slowly and extracted with MTBE extract (3×30 mL). Then the combined organic fraction was dried and concentrated to yield Example 17B (0.75 g, 88% yield) as a yellow solid. LC-MS, [M+H]$^+$=251.

Example 17B 6-(4-Chlorophenyl)pyrrolo[1,2-f][1,2,4]triazin-4(3H)-one

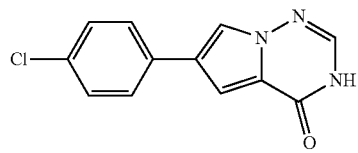 [SMILES: O=c1[nH]cnn2cc(-c3ccc(Cl)cc3)cc12]

A solution of Example 17A (0.75 g, 3 mmol) in formamide (10 mL) was heated to 150° C. in a pressure tube for 12 h. Water was added to the reaction mixture to precipitate a solid which was filtered to yield Example 17B as pale brown solid (0.4 g, 54%). LC-MS, [M+H]$^+$=246.

Example 17

6-(4-Chlorophenyl)-3-(2-pyrrolidin-1-yl-pyrimidin-5-yl)-3H-pyrrolo[2,1-f][1,2,4]triazin-4-one, HCl

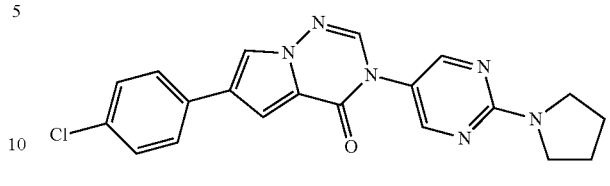

To a solution of 2-(pyrrolidin-1-yl)-5-(4,4,5,5-tetramethyl-1,3,2-dioxaborolan-2-yl)pyrimidine (0.22 g, 0.82 mmol) and Example 17B (0.1 g, 0.41 mmol) in dichloromethane (3 mL) and DMF (1 mL) was added copper acetate (0.15 g, 2 eq), triethylamine (0.12 g, 3 eq) and 1 g 4 Å molecular sieves. The reaction mixture was stirred at room temperature for 24 h open to air. The title compound was then purified by neutral alumina column chromatography with ethyl acetate and hexane as eluents. The resultant solid was taken in ether and HCl in ether added to it to obtain Example 17 as an HCl salt. LC-MS, [M+H]$^+$=393. $^1$H NMR (DMSO-d$_6$, 400 MHz): δ 8.46 (s, 2H), 8.28 (d, J=1.76 Hz, 1H), 8.15 (s, 1H), 7.84 (d, J=8.56 Hz, 2H), 7.49 (d, J=1.76 Hz, 1H), 7.45 (d, J=8.56 Hz, 2H), 3.54 (m, 4H), 1.97 (m, 4H). HPLC-1: Purity=95%, Rt=12.03 min. HPLC-2: Purity=95%, Rt=10.78 min.

Example 18

6-(4-Chlorophenyl)-3-(6-(4-hydroxypiperidin-1-yl)pyridin-3-yl)pyrrolo[1,2-f][1,2,4]triazin-4(3H)-one

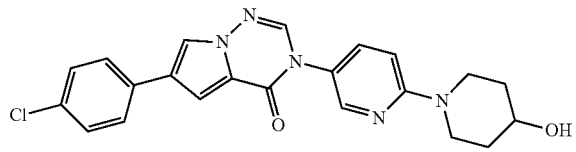 [SMILES: O=c1c2cc(-c3ccc(Cl)cc3)cn2ncn1-c1ccc(N2CCC(O)CC2)nc1]

Example 18A 4-(4-Chlorophenyl)-1-(dimethylamino-methylene-amino)-1H-pyrrole-2-carboxylic acid

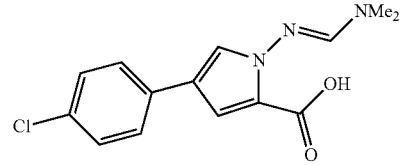 [SMILES: CN(C)/C=N/n1cc(-c2ccc(Cl)cc2)cc1C(=O)O]

Methyl 4-(4-chlorophenyl)-1-((dimethylamino)methyleneamino)-1H-pyrrole-2-carboxylate (Example 4B, 4 g, 13 mmol) was taken in THF/water mixture (30 mL/15 mL) and LiOH (3.29 g, 78 mmol, 6 equiv.) was added to it. Then the mixture was stirred at 60° C. overnight. After confirmation of reaction completion with TLC, THF was removed and the crude mass was neutralized to pH 6-7 using 1.5 N HCl. The white solid obtained was filtered, washed with water and dried to yield Example 18A (2.5 g, 65%). LC-MS, [M+H]$^+$=292. $^1$H NMR (DMSO-d$_6$, 400 MHz): δ 11.0 (br s, 1H), 7.90 (s, 1H), 7.48 (d, J=8.40 Hz, 2H), 7.30 (d, J=8.40 Hz, 2H), 7.07 (d, J=2.40 Hz, 1H), 6.62 (d, J=2.40 Hz, 1H), 2.90 (br s, 6H).

Example 18B 1-(5-Nitropyridin-2-yl)piperidin-4-ol

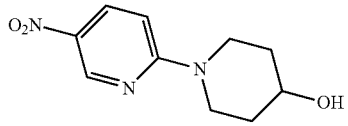 [SMILES: O=[N+]([O-])c1ccc(N2CCC(O)CC2)nc1]

To a solution of 2-chloro-5-nitro pyridine (0.5 g, 3.2 mmol) in DMF was added potassium bicarbonate (0.65 g, 6.4 mmol) and 4-hydroxy piperidine (0.38 g, 3.7 mmol). After heating the reaction mixture for 3 h at 80° C., the mass was quenched into water to obtain a yellow solid obtained which was filtered and dried to yield Example 18B (0.63 g). LC-MS, [M+H]$^+$=224. $^1$H NMR (DMSO-d$_6$, 400 MHz): δ 8.94 (d, J=2.76 Hz, 1H), 8.19 (dd, J=2.76, 9.72 Hz, 1H), 6.95 (d, J=9.72 Hz, 1H), 4.80 (m, 1H), 4.14 (m, 2H), 3.79 (m, 1H), 3.46 (m, 2H), 1.79 (m, 2H), 1.40 (m, 2H).

Example 18C 1-(5-Aminopyridin-2-yl)piperidin-4-ol

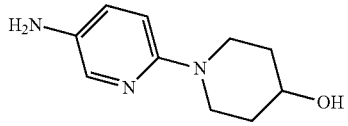

A solution of 1-(5-nitropyridin-2-yl)piperidin-4-ol (Example, 18B, 0.6 g, 2.6 mmol) in ethanol was added 10% palladium on carbon (0.3 g) and the mass was stirred at RT with hydrogen bladder for 3 h. Reaction mass was filtered through CELITE® and concentrated to remove ethanol to yield Example 18C (0.45 g, 89% yield) as a brown oil. LC-MS, [M+H]$^+$=194. $^1$H NMR (CD$_3$OD, 400 MHz): δ 7.70 (d, J=2.6 Hz, 1H), 7.10 (dd, J=2.6, 8.8 Hz, 1H), 6.73 (d, J=8.8 Hz, 1H), 3.76 (m, 3H), 2.91 (m, 2H), 1.89 (m, 2H), 1.51 (m, 2H).

Example 18D 4-(4-Chlorophenyl)-1-((dimethylamino)methyleneamino)-N-(6-(4-hydroxypiperidin-1-yl)pyridin-3-yl)-1H-pyrrole-2-carboxamide

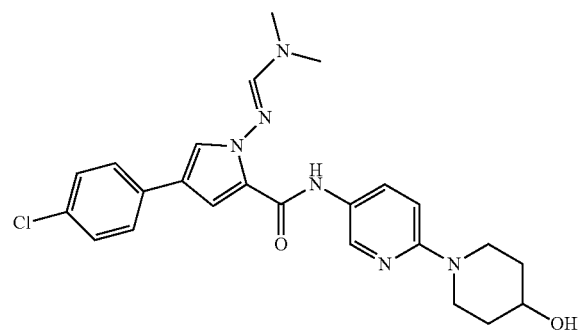 [SMILES: CN(C)/C=N/n1cc(-c2ccc(Cl)cc2)cc1C(=O)Nc1ccc(N2CCC(O)CC2)nc1]

To a mixture of 5-(4-chlorophenyl)-2-(dimethylaminomethyleneamino)-2H-pyrazole-3-carboxylic acid (Example 18A, 0.175 g, 0.59 mmol) and DMF (2 mL) was added HOBT (0.039 g, 0.3 mmol), EDCI HCl (0.33 g, 1.7 mmol) and DIPEA (0.15 g, 1.18 mmol). The resulting mixture was stirred at room temperature for 15 min. Example 18C was then added and the mixture was stirred at room temperature overnight. Reaction mass was quenched into water, solid obtained was filtered and washed with water. Pale brown solid (Example 18D, 0.1 g, 37% yield) obtained was taken to the next step without purification. LC-MS, [M+H]$^+$=467.

Example 18

6-(4-Chlorophenyl)-3-(4-hydroxy-3,4,5,6-tetrahydro-2H-[1,2']bipyridinyl-5'-yl)-3H-pyrrolo[2,1-f][1,2,4]triazin-4-one

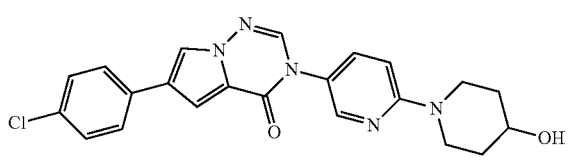 [SMILES: O=c1c2cc(-c3ccc(Cl)cc3)cn2ncn1-c1ccc(N2CCC(O)CC2)nc1]

To a solution of 4-(4-chlorophenyl)-1-((dimethylamino)methyleneamino)-N-(6-(4-hydroxypiperidin-1-yl)pyridin-3-yl)-1H-pyrrole-2-carboxamide (Example 18D, 0.1 g, 0.2 mmol) in acetonitrile was added two drops of acetic acid and the mixture was heated to 160° C. under microwave conditions for 60 min. Reaction mass was cooled to room temperature to yield Example 18 (0.06 g, 71% yield) as an off-white solid after recrystallization with acetonitrile. LC-MS, [M+H]$^+$=422. $^1$H NMR (DMSO-d$_6$, 400 MHz): δ 8.25 (s, 1H), 8.16 (d, J=2.6 Hz, 1H), 8.12 (s, 1H), 7.83 (d, J=8.52 Hz, 2H), 7.64 (dd, J=2.6, 9.2 Hz, 1H), 7.46 (m, 3H), 6.96 (d, J=9.2 Hz, 1H), 4.71 (d, J=4.0 Hz, 1H), 4.07 (m, 2H), 3.76 (m, 1H), 3.20 (m, 2H), 1.81 (m, 2H), 1.41 (m, 2H). HPLC-1: Purity=97%, Rt=8.92 min. HPLC-2: Purity=94%, Rt=8.91 min.

Examples 19 to 21 were prepared in a manner analogous to one described for Example 18.

Example 19

N-(1-{5-[6-(4-Chlorophenyl)-4-oxo-4H-pyrrolo[2,1-f][1,2,4]triazin-3-yl]-pyridin-2-yl}-pyrrolidin-3-yl)-N-ethyl-acetamide

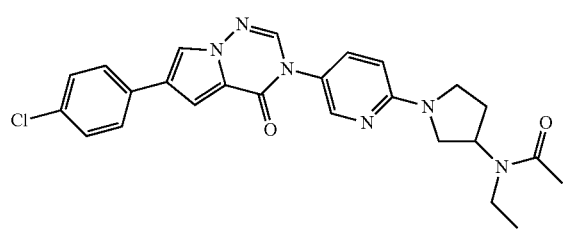 [SMILES: CCN(C(C)=O)C1CCN(c2ccc(-n3cnn4cc(-c5ccc(Cl)cc5)cc4c3=O)cn2)C1]

LC-MS, [M+H]$^+$=477. $^1$H NMR (DMSO-d$_6$, 400 MHz): δ 8.30 (m, 2H), 8.17 (s, 1H), 7.93 (m, 1H), 7.85 (d, J=8.4 Hz, 2H), 7.51 (s, 1H), 7.46 (d, J=8.4 Hz, 2H), 6.98 (d, J=9.2 Hz, 1H), 4.82 (m, 1H), 3.77 (m, 3H), 3.51 (m, 3H), 2.24 (m, 2H), 1.91 (s, 3H), 1.18 (m, 3H). HPLC-1: Purity=98%, Rt=8.56 min. HPLC-2: Purity=98%, Rt=8.79 min.

Example 20

6-(4-Chlorophenyl)-3-[6-(3-hydroxy-azetidin-1-yl)-pyridin-3-yl]-3H-pyrrolo[2,1-f][1,2,4]triazin-4-one

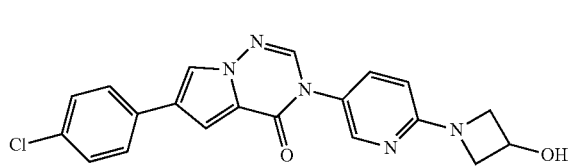 [SMILES: O=c1c2cc(-c3ccc(Cl)cc3)cn2ncn1-c1ccc(N2CC(O)C2)nc1]

LC-MS, [M+H]$^+$=394. $^1$H NMR (DMSO-d$_6$, 400 MHz): δ 8.26 (s, 1H), 8.14 (d, J=2.4 Hz, 1H), 8.11 (s, 1H), 7.83 (d, J=8.48 Hz, 2H), 7.65 (dd, J=2.40, 8.72 Hz, 1H), 7.47 (m, 3H), 6.50 (d, J=8.72 Hz, 1H), 5.71 (d, J=6.44 Hz, 1H), 4.61 (m, 1H), 4.22 (m, 2H), 3.74 (m, 2H). HPLC-1: Purity=92%, Rt=7.45 min. HPLC-2: Purity=92%, Rt=8.15 min.

Example 21

(R)-6-(4-Chlorophenyl)-3-(6-(3-hydroxypyrrolidin-1-yl)pyridin-3-yl)pyrrolo[1,2-f][1,2,4]triazin-4(3H)-one

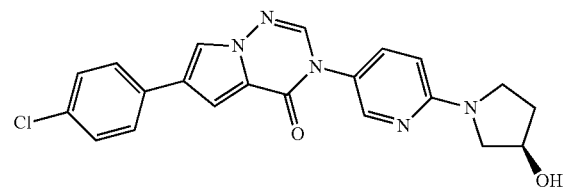 [SMILES: O=c1c2cc(-c3ccc(Cl)cc3)cn2ncn1-c1ccc(N2CC[C@@H](O)C2)nc1]

LC-MS, [M+H]$^+$=408. $^1$H NMR (DMSO-d$_6$, 400 MHz): δ 8.26 (s, 1H), 8.13 (d, J=2.4 Hz, 1H), 8.10 (s, 1H), 7.84 (d, J=8.2 Hz, 2H), 7.61 (dd, J=2.4, 9.0 Hz, 1H), 7.46 (m, 3H), 6.55 (d, J=9.0 Hz, 1H), 4.99 (d, J=2.84 Hz, 1H), 4.41 (m, 1H), 3.52 (m, 4H), 2.07 (m, 2H). HPLC-1: Purity=96%, Rt=7.49 min.

Example 22

1-(4-(6-(4-Chlorophenyl)-4-oxopyrrolo[1,2-f][1,2,4]triazin-3(4H)-yl)-2-methoxyphenoxy)-2-methylpropan-2-yl 2-aminoacetate, HCl

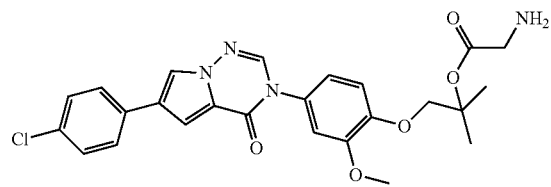 [SMILES: COc1cc(-n2cnn3cc(-c4ccc(Cl)cc4)cc3c2=O)ccc1OCC(C)(C)OC(=O)CN]

Example 22A 1-(2-Methoxy-4-nitrophenoxy)-2-methylpropan-2-yl 2-(tert-butoxycarbonylamino)acetate

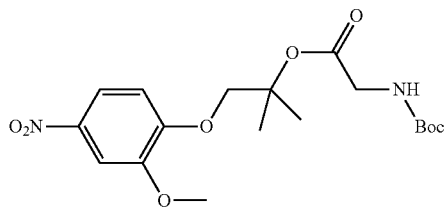 [SMILES: COc1cc([N+](=O)[O-])ccc1OCC(C)(C)OC(=O)CNC(=O)OC(C)(C)C]

To a solution of 1-(2-methoxy-4-nitro-phenoxy)-2-methyl-propan-2-ol (5 g, 21 mmol) in dry dichloromethane, Boc-glycine (10.86 g, 62 mmol, 3 equiv.) and DMAP (3.78 g, 31 mmol, 1.5 equiv.) were added. Then the reaction mass was heated to 40° C. and DIC (7.8 g, 62 mmol, 3 equiv.) was added slowly for a period of 1 h. After completion of addition, the reaction mass was allowed to stir at 40° C. for 4 h. After consumption of starting material, the reaction mass was cooled to room temperature, hydrazine hydrate (3.1 g, 62 mmol, 3 equiv.) was added, and the mixture stirred for 30 min. The reaction mass was filtered and the filtrate was treated with water, saturated brine solution and then dried over sodium sulphate. The concentrate was purified on a 60-120 mesh silica column (0-25% ethyl acetate in pet ether) to yield Example 22A as a yellow oil (7 g, 85% yield). LC-MS, [M+H]$^+$=399. $^1$H NMR (DMSO-d$_6$, 300 MHz): 7.88 (s, 1H), 7.74 (d, 1H), 7.21 (s, 1H), 7.18 (m, 1H), 4.25 (s, 2H), 3.89 (s, 3H), 3.5 (d, 2H), 1.5 (s, 6H), 1.38 (s, 9H).

Example 22B 1-(4-Amino-2-methoxyphenoxy)-2-methylpropan-2-yl 2-(tert-butoxycarbonylamino)acetate

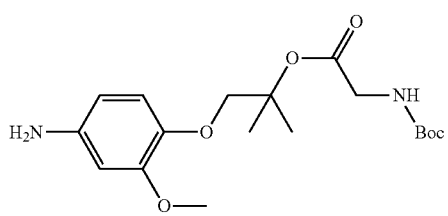 [SMILES: COc1cc(N)ccc1OCC(C)(C)OC(=O)CNC(=O)OC(C)(C)C]

To a solution of Example 22A (7 g, 0.0175 mol) in ethanol was added 10% palladium on carbon and the mass was stirred at RT under hydrogen bladder for 3 h. The reaction mass was filtered through CELITE® and concentrated to remove ethanol to obtain Example 22B (6 g, 93% yield) as a brown oil. LC-MS, [M+H]$^+$=369. $^1$H NMR (DMSO-d$_6$, 300 MHz): 8.3

(s, 1H), 7.1 (s, 1H), 6.57 (d, 1H), 6.23 (d, 1H), 6.03 (m, 1H), 4.71 (s, 2H), 3.87 (s, 3H), 3.5 (d, 2H), 1.46 (s, 6H), 1.36 (s, 9H).

Example 22C 1-(4-(4-(4-Chlorophenyl)-1-((dimethylamino)methyleneamino)-1H-pyrrole-2-carboxamido)-2-methoxyphenoxy)-2-methylpropan-2-yl 2-(tert-butoxycarbonylamino)acetate

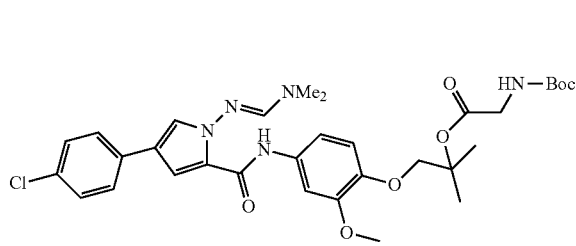 [SMILES: COc1cc(NC(=O)c2cc(-c3ccc(Cl)cc3)cn2/N=C/N(C)C)ccc1OCC(C)(C)OC(=O)CNC(=O)OC(C)(C)C]

To a mixture of 5-(4-chlorophenyl)-2-(dimethylaminomethyleneamino)-2H-pyrazole-3-carboxylic acid (0.5 g, 1.7 mmol) and DMF was added HOBT (0.114 g, 0.85 mmol), EDCI HCl (0.97 g, 5.1 mmol) and DIPEA (0.43 g, 3.4 mmol). The resultant mixture was stirred at room temperature for 15 min, then aniline Example 22B was added and the mixture stirred overnight at the same temperature. Reaction mass was quenched with water to obtain Example 22C as a pale brown solid (0.7 g, 64% yield). LC-MS, [M+H]$^+$=642. $^1$H NMR (DMSO-d$_6$, 400 MHz): 10.08 (s, 1H), 8.39 (s, 1H), 7.82 (d, 1H), 7.62 (d, 2H), 7.39 (d, 3H), 7.14 (m, 3H), 6.9 (s, 1H), 4.04 (s, 2H), 3.76 (s, 3H), 3.56 (d, 2H), 3.08 (s, 6H), 1.48 (s, 6H), 1.36 (s, 9H).

Example 22D 1-(4-(6-(4-Chlorophenyl)-4-oxopyrrolo[1,2-f][1,2,4]triazin-3(4H)-yl)-2-methoxyphenoxy)-2-methylpropan-2-yl 2-(tert-butoxycarbonylamino)acetate

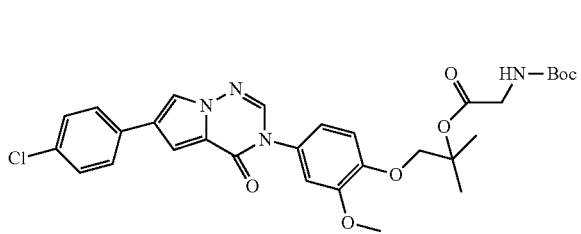 [SMILES: COc1cc(-n2cnn3cc(-c4ccc(Cl)cc4)cc3c2=O)ccc1OCC(C)(C)OC(=O)CNC(=O)OC(C)(C)C]

Example 22C (0.7 g, 1.1 mmol) was taken in acetonitrile and this solution was heated to 160° C. for 30 min under microwave irradiation. Then acetonitrile was removed in vacuo and the crude product was purified by neutral alumina column chromatography using 0-25% ethyl acetate in hexane to obtain Example 22D (0.25 g, 42% yield) as a white solid. LC-MS, [M+H]$^+$=597. $^1$H NMR (DMSO-d$_6$, 400 MHz): 8.25 (s, 1H), 8.11 (s, 1H), 7.83 (m, 2H), 7.46 (m, 3H), 7.14 (m, 4H), 4.15 (s, 2H), 3.78 (s, 3H), 3.56 (d, 2H), 1.51 (s, 6H), 1.36 (s, 9H).

Example 22

2-{4-[6-(4-Chlorophenyl)-4-oxo-4H-pyrrolo[2,1-f][1,2,4]triazin-3-yl]-2-methoxy-phenoxy}-1,1-dimethyl-ethyl ester, HCl

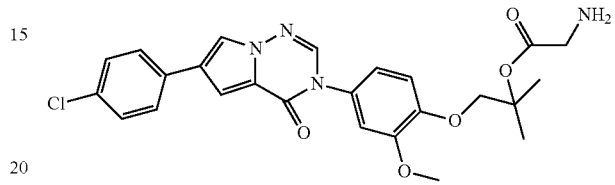

Example 22D (0.25 g, 0.4 mmol) was taken in 5 mL diethyl ether and HCl in diethyl ether 2 mL was added to it while maintaining the temperature ~5-10° C. The solution turned gummy and upon washing with ether became a free-flowing solid (Example 22, 0.2 g, 95% yield). LC-MS, [M+H]$^+$=497. $^1$H NMR (DMSO-d$_6$, 400 MHz): δ 8.28 (m, 4H), 8.11 (s, 1H), 7.84 (d, J=8.52 Hz, 2H), 7.47 (m, 3H), 7.21 (d, J=2.32 Hz, 1H), 7.14 (d, J=8.68 Hz, 1H), 7.05 (dd, J=2.32, 8.86 Hz, 1H), 4.21 (s, 2H), 3.79 (s, 3H), 3.73 (m, 2H), 1.58 (s, 6H). HPLC-1: Purity=97%, Rt=7.99 min. HPLC-2: Purity=97%, Rt=9.34 min.

Example 23

3-(2-Acetyl-1,2,3,4-tetrahydro-isoquinolin-6-yl)-6-(4-chlorophenyl)-3H-pyrrolo[2,1-j][1,2,4]triazin-4-one

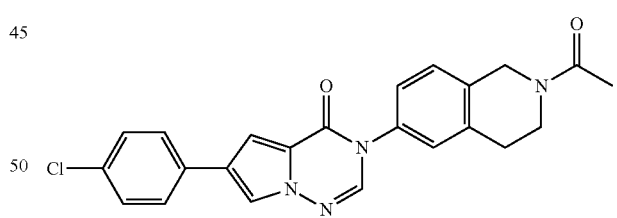

To a solution of Example 17B (0.03 g, 0.12 mmol) and 1-(6-bromo-3,4-dihydroisoquinolin-2(1H)-yl)ethanone (0.1 g, 0.39 mmol) in DMF/1,4-dioxane mixture, potassium phosphate tribasic (0.15 g, 0.7 mmol) and dimethyl trans-cyclohexane diamine (0.1 mL, 0.6 mmol) were added. Then copper iodide was added to the reaction mass and the mixture irradiated in a microwave reactor at 120° C. for 1 h. Water was added and the reaction mixture extracted with ethyl acetate. The concentrate was purified with preparative HPLC to yield Example 23 as a pale yellow solid (0.015 g, 20% yield). LC-MS, [M+H]$^+$=419. $^1$H NMR (DMSO-d$_6$, 400 MHz): δ 8.27 (s, 1H), 8.13 (s, 1H), 7.84 (d, J=8.36 Hz, 2H), 7.48 (s, 1H), 7.45 (d, J=8.36 Hz, 2H), 7.38 (m, 3H), 4.72 (m, 2H), 3.69 (m, 2H), 2.93 (m, 2H), 2.11 (s, 3H). HPLC-1: Purity=93%, Rt=10.99 min.

Example 24

(S)—((R)-1-(4-(6-(4-Chlorophenyl)-4-oxopyrrolo[1,2-f][1,2,4]triazin-3(4H)-yl)-2-methoxyphenyl)pyrrolidin-3-yl) 2-amino-3-methylbutanoate, HCl

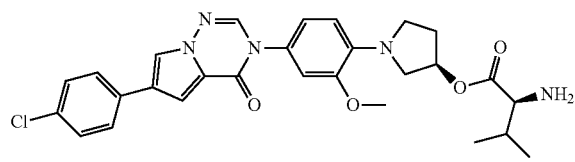 [SMILES: COc1cc(-n2cnn3cc(-c4ccc(Cl)cc4)cc3c2=O)ccc1N1CC[C@@H](OC(=O)[C@@H](N)C(C)C)C1]

Example 24A (R)-1-(2-Methoxy-4-nitrophenyl)pyrrolidin-3-ol

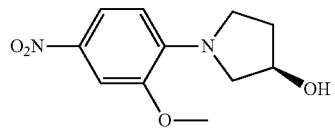 [SMILES: COc1cc([N+](=O)[O-])ccc1N1CC[C@@H](O)C1]

A mixture of 2-chloro-5-nitroanisole (0.59 g, 3.1 mmol) and 3-hydroxy pyrrolidine (0.55 g, 6.2 mmol) was heated neat to 110° C. over night. Reaction mass was diluted with ethyl acetate and the organic layer was given water and brine wash, dried over Na$_2$SO$_4$, concentration yields dark red solid (0.6 g, 82% yield). LC-MS, [M+H]$^+$=239.

Example 24B (S)—((R)-1-(2-Methoxy-4-nitrophenyl)pyrrolidin-3-yl) 2-(tert-butoxycarbonylamino)-3-methylbutanoate

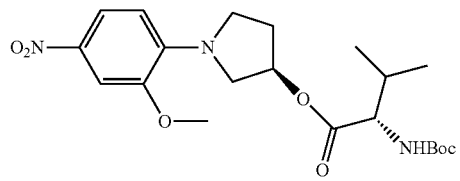 [SMILES: COc1cc([N+](=O)[O-])ccc1N1CC[C@@H](OC(=O)[C@@H](NC(=O)OC(C)(C)C)C(C)C)C1]

To a solution of (R)-1-(2-methoxy-4-nitrophenyl)pyrrolidin-3-ol, (1.0 g, 4.2 mmol) in dichloromethane was added Boc-valine (1.8 g, 8.4 mmol) and 4-dimethylamino pyridine (0.25 g, 2.1 mmol) and the mixture stirred at room temperature for 30 min. N,N-diisopropylcarbodimide (1.05 g, 8.4 mmol) was then added and the mixture stirred overnight at room temperature under nitrogen. Reaction mass was then diluted with ethyl acetate and the organic layer was given water and brine washes and dried over Na$_2$SO$_4$. Concentration of organic layer yielded Example 24B (1.7 g, 94% yield). LC-MS, [M+H]$^+$=438.

Example 24C (S)—((R)-1-(4-Amino-2-methoxyphenyl)pyrrolidin-3-yl) 2-(tert-butoxycarbonylamino)-3-methylbutanoate

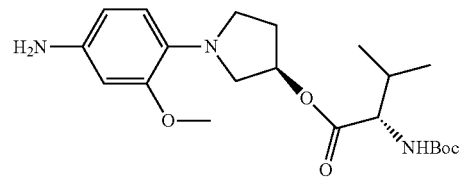

To a solution of Example 24B (1.7 g, 3.8 mmol) in ethanol was added 10% palladium on carbon (0.9 g) and the mass was stirred at RT under hydrogen atmosphere (bladder) for 3 h. Reaction mass was filtered through CELITE® and evaporated in vacuo to yield Example 24C (1.5 g, 97% yield) as a brown oil.

Example 24

(S)—((R)-1-(4-(6-(4-Chlorophenyl)-4-oxopyrrolo[1,2-f][1,2,4]triazin-3(4H)-yl)-2-methoxyphenyl)pyrrolidin-3-yl) 2-amino-3-methylbutanoate, HCl

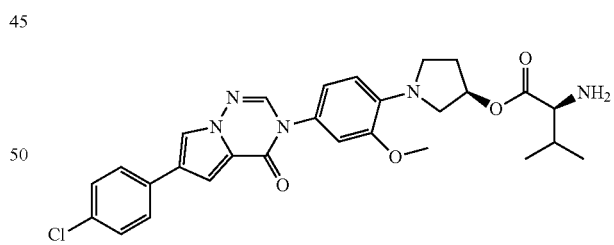

Example 24 was obtained according to the procedure adopted for Example 22 from Example 24C and Example 18A. LC-MS, [M+H]$^+$=536. $^1$H NMR (DMSO-d$_6$, 400 MHz): δ 8.31 (m, 4H), 8.10 (s, 1H), 7.85 (d, J=8.40 Hz, 2H), 7.46 (m, 3H), 7.10 (d, J=2.00 Hz, 1H), 6.98 (dd, J=2.00, 8.40 Hz, 1H), 6.79 (d, J=8.40 Hz, 1H), 5.46 (m, 1H), 3.93 (m, 3H), 3.78 (s, 3H), 3.39 (m, 2H), 2.33 (m, 3H), 1.00 (m, 6H). HPLC-1: Purity=95%, Rt=8.65 min. HPLC-2: Purity=95%, Rt=9.79 min.

Examples 25 to 28 were prepared in a manner analogous to Example 18 from the corresponding anilines and Example 18A.

Example 25

6-(4-Chlorophenyl)-3-[4-(2-hydroxy-propoxy)-3-methoxy-phenyl]-3H-pyrrolo[2,1-f][1,2,4]triazin-4-one

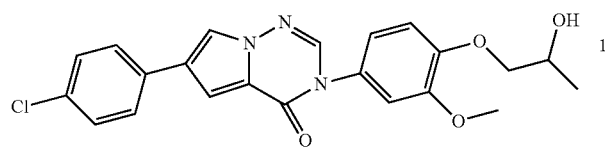

LC-MS, [M+H]$^+$=426. $^1$H NMR (DMSO-d$_6$, 400 MHz): δ 8.28 (s, 1H), 8.13 (s, 1H), 7.85 (d, J=8.4 Hz, 2H), 7.48 (m, 3H), 7.17 (d, J=2.00 Hz, 1H), 7.10 (d, J=8.40 Hz, 1H), 7.03 (dd, J=2.00, 8.40 Hz, 1H), 4.90 (d, J=4.80 Hz, 1H), 3.99 (m, 3H), 3.82 (s, 3H), 1.18 (d, J=4.80 Hz, 3H). HPLC-1: Purity=99%, Rt=17.86 min. HPLC-2: Purity=98%, Rt=16.03 min.

Example 26

6-(4-Chlorophenyl)-3-[4-(3,4-dihydroxy-pyrrolidin-1-yl)-3-methoxy-phenyl]-3H-pyrrolo[2,1-f][1,2,4]triazin-4-one

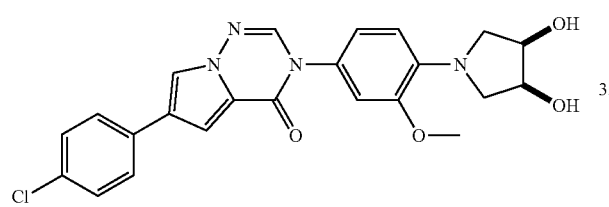

LC-MS, [M+H]$^+$=453. $^1$H NMR (DMSO-d$_6$, 400 MHz): δ 8.26 (s, 1H), 8.09 (s, 1H), 7.85 (d, J=8.4 Hz, 2H), 7.46 (m, 3H), 7.04 (d, J=2.00 Hz, 1H), 6.93 (dd, J=2.00, 8.40 Hz, 1H), 6.63 (d, J=8.40 Hz, 1H), 4.83 (d, J=4.40 Hz, 2H), 4.08 (m, 2H), 3.75 (s, 3H), 3.56 (m, 2H), 3.23 (m, 2H). HPLC-1: Purity=96%, Rt=10.09 min. HPLC-2: Purity=97%, Rt=9.40 min.

Example 27

6-(4-Chlorophenyl)-3-{6-[3-(3-hydroxy-azetidin-1-yl)-pyrrolidin-1-yl]-pyridin-3-yl}-3H-pyrrolo[2,1-f][1,2,4]triazin-4-one, HCl salt

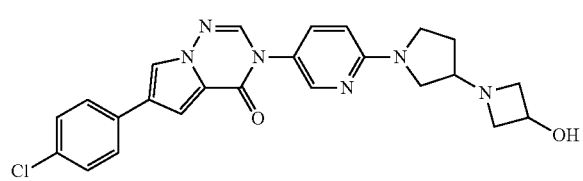 [SMILES: O=c1c2cc(-c3ccc(Cl)cc3)cn2ncn1-c1ccc(N2CCC(N3CC(O)C3)C2)nc1]

LC-MS, [M+H]$^+$=463. $^1$H NMR (DMSO-d$_6$, 400 MHz): δ 11.08 (br s, 1H), 8.28 (m, 3H), 7.84 (m, 3H), 7.48 (m, 3H), 6.76 (m, 1H), 4.43 (m, 5H), 3.93 (m, 4H), 2.34 (m, 4H). HPLC-2: Purity=91%, Rt=13.51 min.

Example 28

6-(4-Chlorophenyl)-3-[4-(1,1-dioxo-1λ$^6$-thiomorpholin-4-yl)-3-methoxy-phenyl]-3H-pyrrolo[2,1-f][1,2,4]triazin-4-one

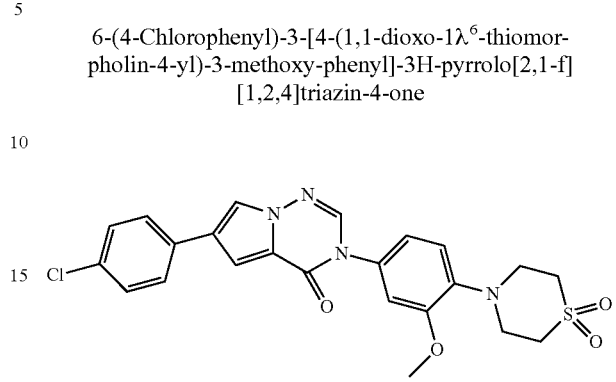

LC-MS, [M+H]$^+$=485. $^1$H NMR (DMSO-d$_6$, 400 MHz): δ 8.28 (s, 1H), 8.14 (s, 1H), 7.85 (d, J=8.80 Hz, 2H), 7.49 (m, 3H), 7.20 (d, J=2.0 Hz, 1H), 7.15 (d, J=8.40 Hz, 1H), 7.06 (dd, J=2.0, 8.40 Hz, 1H), 3.83 (s, 3H), 3.49 (m, 4H), 3.26 (m, 4H). HPLC-1: Purity=98%, Rt=11.36 min. HPLC-2: Purity=98%, Rt=10.59 min.

Example 29

6-(5-Chloropyridin-2-yl)-3-[4-(2-cyclopropyl-2-hydroxy-ethoxy)-3-methoxy-phenyl]-3H-pyrrolo[2,1-f][1,2,4]triazin-4-one

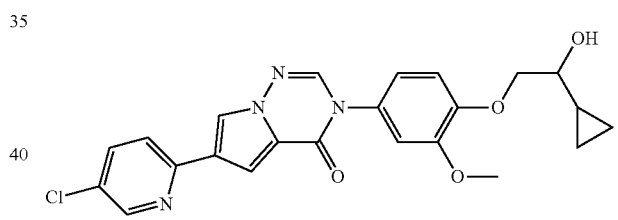

Example 29A

4-Bromo-1-(dimethylamino-methyleneamino)-1H-pyrrole-2-carboxylic acid [4-(2-cyclopropyl-2-hydroxy-ethoxy)-3-methoxy-phenyl]-amide

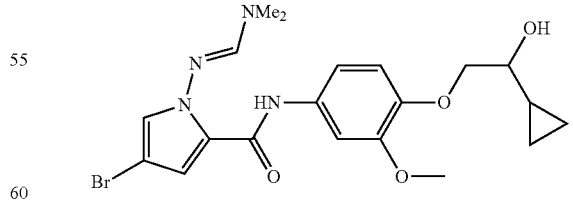

To a solution of 4-bromo-1-(dimethylamino-methyleneamino)-1H-pyrrole-2-carboxylic acid (synthesized from Example 1E using a method similar to one used for Example 18A, 0.23 g, 0.88 mmol) in dry DMF was added HOBT (0.14 g, 1.06 mmol), EDCI HCl (0.20 g, 1.06 mmol) and DIPEA (0.45 mL, 2.65 mmol). The mixture was stirred at room temperature for 15 min, then 2-(4-amino-2-methoxyphenoxy)-1-cyclopropylethanol (prepared by a method adapted from Example 48D, 0.24 g, 1.07 mmol) was added and the mixture stirred at room temperature overnight. Reaction mass was quenched into water, solid obtained was filtered and washed with water. Example 29A (0.15 g, 36% yield) was obtained as an off-white solid. LC-MS, [M+H]$^+$=465.

Example 29B

6-Bromo-3-[4-(2-cyclopropyl-2-hydroxy-ethoxy)-3-methoxy-phenyl]-3H-pyrrolo[2,1-f][1,2,4]triazin-4-one

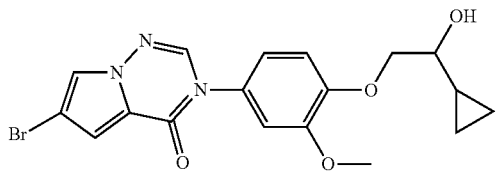

Example 29A, (0.15 g, 0.32 mmol) was taken in acetonitrile and catalytic amount of acetic acid added to it. This mass was heated to 160° C. for 30 min under microwave irradiation. Reaction mass was cooled to room temperature, the solid obtained was filtered and washed with acetonitrile to yield Example 29B (0.12 g, 89% yield) as a pale brown solid. LC-MS, [M+H]$^+$=420.

Example 29C

3-[4-(2-Cyclopropyl-2-hydroxy-ethoxy)-3-methoxy-phenyl]-6-(4,4,5,5-tetramethyl-[1,3,2]dioxaborolan-2-yl)-3H-pyrrolo[2,1-f][1,2,4]triazin-4-one

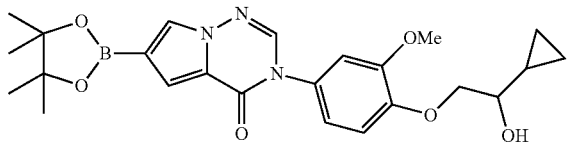 [SMILES: COc1cc(-n2cnn3cc(B4OC(C)(C)C(C)(C)O4)cc3c2=O)ccc1OCC(O)C1CC1]

To Example 29B (0.4 g, 0.95 mmol) in dry DMF in a pressure tube was added bis(pinacalato)diborane (0.29 g, 1.14 mmol), potassium acetate (0.24 g, 2.375 mmol) and the mixture was degassed. Pd(dppf)Cl$_2$ (0.07 g, 0.095 mmol) was then added and the mixture heated to 100° C. overnight. Reaction mass was concentrated to remove DMF and the crude mass was washed with diethyl ether. The solid obtained was filtered, washed with diethyl ether and discarded. The ether layer was washed with water, brine, and dried over Na$_2$SO$_4$. Evaporation yielded Example 29C (0.19 g, 42% yield) as a brown oil which was taken to the next step without further purification.

Example 29

6-(5-Chloropyridin-2-yl)-3-[4-(2-cyclopropyl-2-hydroxy-ethoxy)-3-methoxy-phenyl]-3H-pyrrolo[2,1-f][1,2,4]triazin-4-one

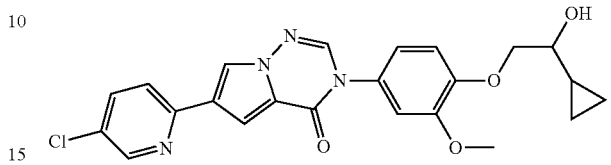

To a solution of Example 29C (0.19 g, 0.4 mmol) in DMF, was added 5-bromo-2-chloro pyridine (0.08 g, 0.4 mmol), potassium carbonate (0.11 g, 0.81 mmol) and water. The mixture was degassed, Pd(dppf)Cl$_2$ (0.033 g, 0.04 mmol) was added and the mixture heated to 100° C. under microwave conditions for 60 min. Reaction mass was concentrated to remove DMF and diluted with ethyl acetate. Organic layer was washed with water, brine, dried over Na$_2$SO$_4$ and concentrated to yield a brown oil. Purification by silica (230-400 mesh) column chromatography using hexane and ethyl acetate as eluents, yielded Example 29 (0.045 g, 24% yield) as a white solid. LC-MS, [M+H]$^+$=453. $^1$H NMR (DMSO-d$_6$, 400 MHz): δ 8.61 (d, J=1.64 Hz, 1H), 8.29 (s, 1H), 8.15 (s, 1H), 7.99 (m, 2H), 7.56 (s, 1H), 7.17 (d, J=2.04 Hz, 1H), 7.11 (d, J=8.60 Hz, 1H), 7.03 (dd, J=2.04, 8.60 Hz, 1H), 4.89 (d, J=5.00 Hz, 1H), 4.02 (m, 2H), 3.77 (s, 3H), 3.35 (m, 1H), 0.97 (m, 1H), 0.41 (m, 2H), 0.39 (m, 2H). HPLC-1: Purity=95%, Rt=10.31 min. HPLC-2: Purity=95%, Rt=9.33 min.

Examples 30 to 34 were prepared in a manner analogous to Example 29.

Example 30

6-(5-Chloropyridin-2-yl)-3-[4-(3-hydroxy-pyrrolidin-1-yl)-3-methoxy-phenyl]-3H-pyrrolo[2,1-f][1,2,4]triazin-4-one

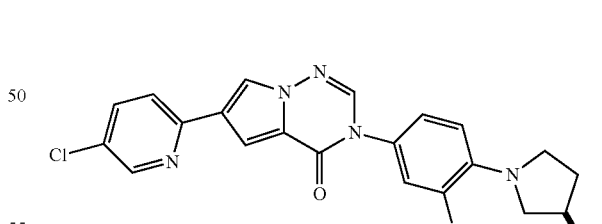

LC-MS, [M+H]$^+$=438. $^1$H NMR (DMSO-d$_6$, 400 MHz): δ 8.60 (d, J=1.40 Hz, 1H), 8.27 (s, 1H), 8.12 (s, 1H), 7.98 (m, 2H), 7.55 (s, 1H), 7.05 (d, J=2.12 Hz, 1H), 6.94 (dd, J=2.12, 8.56 Hz, 1H), 6.69 (d, J=8.56 Hz, 1H), 4.87 (d, J=3.64 Hz, 1H), 4.32 (m, 1H), 3.75 (s, 3H), 3.62 (m, 1H), 3.42 (m, 1H), 3.28 (m, 1H), 3.13 (m, 1H), 1.95 (m, 1H), 1.75 (m, 1H). HPLC-1: Purity=96%, Rt=8.14 min. HPLC-2: Purity=96%, Rt=8.21 min.

Example 31

6-(5-Chloropyridin-2-yl)-3-[6-(3-hydroxy-pyrrolidin-1-yl)-pyridin-3-yl]-3H-pyrrolo[2,1-f][1,2,4]triazin-4-one

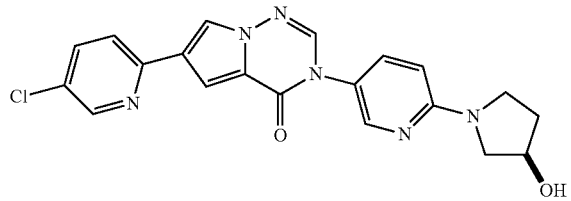 [SMILES: O=c1c2cc(-c3ccc(Cl)cn3)cn2ncn1-c1ccc(N2CC[C@@H](O)C2)nc1]

LC-MS, [M+H]⁺=409. ¹H NMR (DMSO-d₆, 400 MHz): δ 8.61 (s, 1H), 8.29 (s, 1H), 8.15 (m, 2H), 7.99 (m, 2H), 7.63 (dd, J=1.6, 9.2 Hz, 1H), 7.57 (s, 1H), 6.55 (d, J=9.2 Hz, 1H), 5.02 (d, J=3.6 Hz, 1H), 4.41 (m, 1H), 3.54 (m, 3H), 3.44 (m, 1H), 2.09 (m, 1H), 1.99 (m, 1H). HPLC-1: Purity=94%, Rt=6.21 min. HPLC-2: Purity=94%, Rt=6.96 min.

Example 32

6-(5-Chloropyrimidin-2-yl)-3-[4-(2-cyclopropyl-2-hydroxy-ethoxy)-3-methoxy-phenyl]-3H-pyrrolo[2,1-f][1,2,4]triazin-4-one

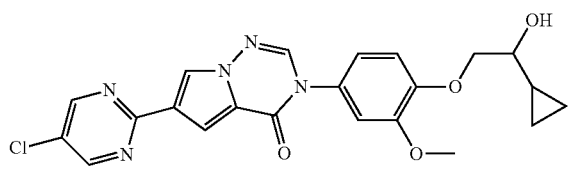 [SMILES: COc1cc(-n2cnn3cc(-c4ncc(Cl)cn4)cc3c2=O)ccc1OCC(O)C1CC1]

LC-MS, [M+H]⁺=454. ¹H NMR (DMSO-d₆, 400 MHz): δ 8.94 (s, 2H), 8.27 (d, J=1.2 Hz, 1H), 8.20 (s, 1H), 7.49 (d, J=1.2 Hz, 1H), 7.19 (d, J=2.0 Hz, 1H), 7.12 (d, J=8.4 Hz, 1H), 7.04 (dd, J=2.0, 8.4 Hz, 1H), 4.90 (d, J=5.2 Hz, 1H), 4.03 (m, 2H), 3.78 (s, 3H), 3.36 (m, 1H), 0.97 (m, 1H), 0.42 (m, 2H), 0.32 (m, 2H). HPLC-1: Purity=97%, Rt=15.69 min. HPLC-2: Purity=97%, Rt=14.10 min.

Example 33

6-(5-Chloropyridin-2-yl)-3-[4-(2-hydroxy-2-methyl-propoxy)-3-methoxy-phenyl]-3H-pyrrolo[2,1-f][1,2,4]triazin-4-one

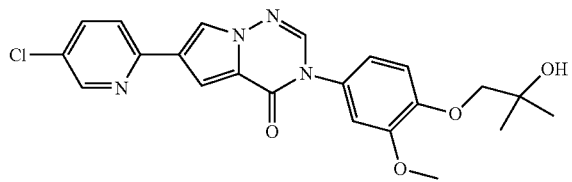 [SMILES: COc1cc(-n2cnn3cc(-c4ccc(Cl)cn4)cc3c2=O)ccc1OCC(C)(C)O]

LC-MS, [M+H]⁺=441. ¹H NMR (DMSO-d₆, 400 MHz): δ 8.62 (d, J=2.00 Hz, 1H), 8.30 (s, 1H), 8.16 (s, 1H), 7.99 (m, 2H), 7.57 (s, 1H), 7.18 (d, J=1.20 Hz, 1H), 7.10 (d, J=8.40 Hz, 1H), 7.04 (dd, J=1.20, 8.40 Hz, 1H), 4.65 (s, 1H), 3.79 (s, 3H), 3.76 (s, 2H), 1.23 (s, 6H). HPLC-1: Purity=92%, Rt=10.07 min. HPLC-2: Purity=93%, Rt=9.30 min.

Example 34

6-(5-Chloropyrimidin-2-yl)-3-[4-(2-hydroxy-2-methyl-propoxy)-3-methoxy-phenyl]-3H-pyrrolo[2,1-f][1,2,4]-triazin-4-one

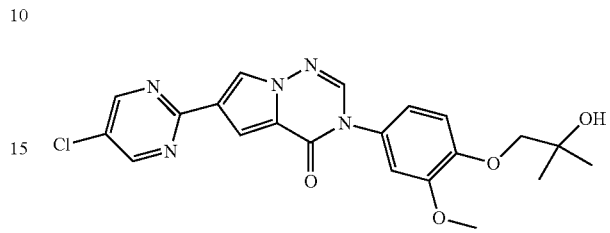

LC-MS, [M+H]⁺=442. ¹H NMR (DMSO-d₆, 400 MHz): δ 8.94 (s, 2H), 8.28 (d, J=1.6 Hz, 1H), 8.20 (s, 1H), 7.49 (d, J=1.6 Hz, 1H), 7.19 (d, J=2.4 Hz, 1H), 7.11 (d, J=8.8 Hz, 1H), 7.04 (dd, J=2.4, 8.8 Hz, 1H), 4.64 (s, 1H), 3.79 (s, 3H), 3.76 (s, 2H), 1.23 (s, 6H). HPLC-1: Purity=96%, Rt=9.72 min. HPLC-2: Purity=96%, Rt=8.85 min.

Examples 35 to 37 were prepared in a manner analogous to Example 6.

Example 35

(3-[4-(2-(Pyrrolidin-1-yl)ethoxy)-3-methoxyphenyl]-6-(4-chlorophenyl)pyrazolo[5,1-f][1,2,4]triazin-4(3H)-one)

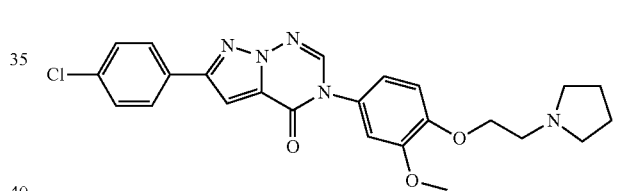

LC-MS, [M+H]⁺=466. ¹H NMR (DMSO-d₆, 400 MHz): δ 8.38 (s, 1H), 8.05 (d, J=8.56 Hz, 2H), 7.73 (s, 1H), 7.56 (d, J=8.56 Hz, 2H), 7.22 (d, J=2.32 Hz, 1H), 7.14 (d, J=8.6 Hz, 1H), 7.08 (dd, J=2.32, 8.5 Hz, 1H), 4.13 (t, J=6.0 Hz, 2H), 3.78 (s, 3H), 2.83 (t, J=6.0 Hz, 2H), 2.53 (m, 4H), 1.70 (m, 4H). HPLC-1: Purity=95%, Rt=7.4 min. HPLC-2: Purity=96%, Rt=8.8 min.

Example 36

6-(4-Chlorophenyl)-3-{6-[3-(methylamino)pyrrolidin-1-yl]pyridin-3-yl}pyrazolo[5,1-f][1,2,4]triazin-4(3H)-one, TFA

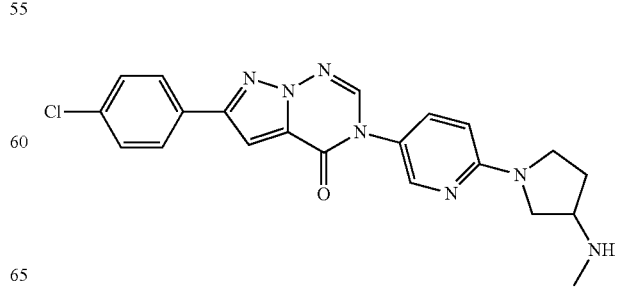

LC-MS, [M+H]⁺=422. ¹H NMR (DMSO-d₆, 400 MHz): δ 8.72 (br s, 2H), 8.38 (s, 1H), 8.25 (d, J=2.4 Hz, 1H), 8.05 (d, J=8.4 Hz, 2H), 7.74 (m, 2H), 7.57 (d, J=8.4 Hz, 2H), 6.70 (d, J=8.8 Hz, 1H), 3.92 (m, 1H), 3.80 (m, 1H), 3.70 (m, 4H), 2.69 (m, 3H), 2.41 (m, 1H), 2.21 (m, 1H). HPLC-1: Purity=98%, Rt=6.68 min. HPLC-2: Purity=98%, Rt=7.74 min.

Example 37

6-(4-Chlorophenyl)-3-[4-(2-cyclopropyl-2-hydroxy-ethoxy)-3-methoxyphenyl]pyrazolo[5,1-f][1,2,4]triazin-4(3H)-one

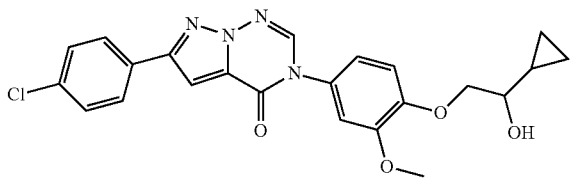 [SMILES: COc1cc(-n2cnn3nc(-c4ccc(Cl)cc4)cc3c2=O)ccc1OCC(O)C1CC1]

LC-MS, [M+H]⁺=453. ¹H NMR (DMSO-d₆, 400 MHz): δ 8.38 (s, 1H), 8.05 (d, J=8.16 Hz, 2H), 7.73 (s, 1H), 7.56 (d, J=8.16 Hz, 2H), 7.21 (d, J=2.0 Hz, 1H), 7.14 (d, J=7.96 Hz, 1H), 7.07 (dd, J=2.0, 7.96 Hz, 1H), 4.89 (d, J=4.4 Hz, 1H), 3.99 (s, 2H), 3.77 (s, 3H), 0.96 (m, 1H), 0.40 (m, 2H), 0.31 (m, 2H). HPLC-1: Purity=96%, Rt=11.1 min. HPLC-2: Purity=95%, Rt=10.2 min.

Example 38

6-(4-Chlorophenyl)-3-(3,4-dimethoxy-phenyl)-3H-imidazo[2,1-f][1,2,4]triazin-4-one

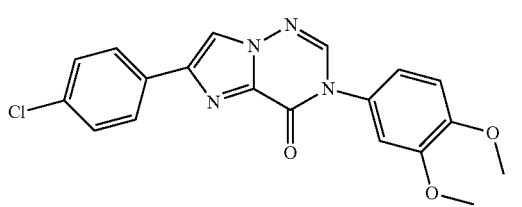 [SMILES: COc1ccc(-n2cnn3cc(-c4ccc(Cl)cc4)nc3c2=O)cc1OC]

Example 38 was prepared using a procedure analogous to Example 7. LC-MS, [M+H]⁺=383. ¹H NMR (DMSO-d₆, 400 MHz): δ 8.68 (s, 1H), 8.40 (s, 1H), 8.02 (d, J=8.4 Hz, 2H), 7.54 (d, J=8.4 Hz, 2H), 7.20 (m, 3H), 3.83 (s, 3H), 3.77 (s, 3H). HPLC-1: Purity=97%, Rt=10.44 min. HPLC-2: Purity=97%, Rt=9.70 min.

Example 39

6-(4-Chlorophenyl)-3-[4-(2-cyclopropyl-2-hydroxy-ethoxy)-3-methoxy-phenyl]-3H-imidazo[2,1-f][1,2,4]triazin-4-one

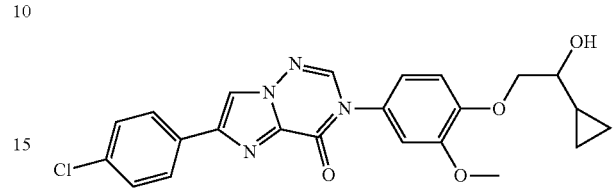

Example 39A (E)-Methyl 4-(4-chlorophenyl)-1-((dimethylamino)methyleneamino)-1H-imidazole-2-carboxylate

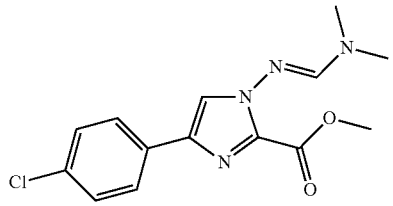 [SMILES: COC(=O)c1nc(-c2ccc(Cl)cc2)cn1/N=C/N(C)C]

Example 39A was prepared from Example 7B in a manner analogous to Example 5B. LC-MS, [M+H]⁺=307. ¹H NMR (DMSO-d₆, 400 MHz): δ 8.11 (s, 1H), 8.01 (s, 1H), 7.82 (d, J=8.4 Hz, 2H), 7.45 (d, J=8.4 Hz, 2H), 3.79 (s, 3H), 3.00 (s, 3H), 2.92 (s, 3H).

Example 39B (E)-4-(4-Chlorophenyl)-1-((dimethylamino)methyl-eneamino)-1H-imidazole-2-carboxylic acid

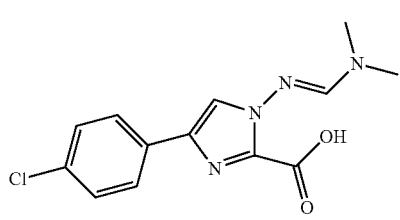 [SMILES: CN(C)/C=N/n1cc(-c2ccc(Cl)cc2)nc1C(=O)O]

Example 39B was prepared using a procedure analogous to Example 18A starting from Example 39A. LC-MS, [M+H]⁺=293.

Example 39

6-(4-Chlorophenyl)-3-[4-(2-cyclopropyl-2-hydroxy-ethoxy)-3-methoxy-phenyl]-3H-imidazo[2,1-f][1,2,4]triazin-4-one

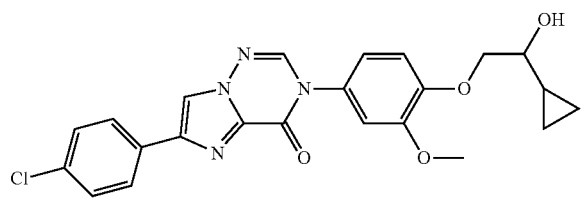

Example 39 was prepared using a procedure analogous to Example 18 above from 2-(4-amino-2-methoxyphenoxy)-1-cyclopropylethanol and Example 39B. LC-MS, [M+H]$^+$=453. $^1$H NMR (DMSO-d$_6$, 400 MHz): δ 8.68 (s, 1H), 8.39 (s, 1H), 8.03 (d, J=8.4 Hz, 2H), 7.54 (d, J=8.4 Hz, 2H), 7.21 (d, J=2.40 Hz, 1H), 7.15 (d, J=8.80 Hz, 1H), 7.07 (dd, J=2.40, 8.80 Hz, 1H), 4.91 (d, J=4.80 Hz, 1H), 4.00 (m, 2H), 3.78 (s, 3H), 3.33 (m, 1H), 0.97 (m, 1H), 0.43 (m, 4H). HPLC-1: Purity=97%, Rt=10.29 min. HPLC-2: Purity=98%, Rt=9.64 min.

Example 40

(S)—((R)-1-(5-(6-(4-Chlorophenyl)-4-oxopyrrolo[1,2-f][1,2,4]triazin-3(4H)-yl)pyridin-2-yl)pyrrolidin-3-yl) 2-amino-3-methylbutanoate, 2 TFA

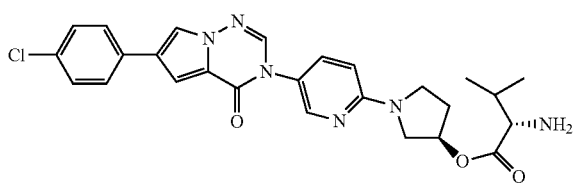 [SMILES: CC(C)[C@H](N)C(=O)O[C@@H]1CCN(c2ccc(-n3cnn4cc(-c5ccc(Cl)cc5)cc4c3=O)cn2)C1]

Example 40A (S)—((R)-1-(5-(6-(4-Chlorophenyl)-4-oxopyrrolo[1,2-f][1,2,4]triazin-3(4H)-yl)pyridin-2-yl)pyrrolidin-3-yl) 2-(tert-butoxycarbonylamino)-3-methylbutanoate

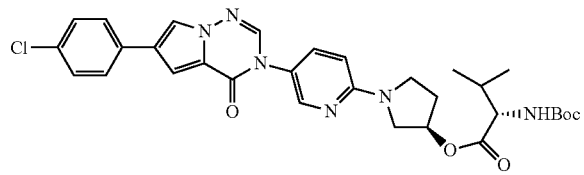 [SMILES: CC(C)[C@H](NC(=O)OC(C)(C)C)C(=O)O[C@@H]1CCN(c2ccc(-n3cnn4cc(-c5ccc(Cl)cc5)cc4c3=O)cn2)C1]

To a solution of Example 21 (20.5 mg, 0.050 mmol), DMAP (1.2 mg, 9.82 μmol), and (S)-2-(tert-butoxycarbonylamino)-3-methylbutanoic acid (14.20 mg, 0.065 mmol) in DCM (0.218 mL) was added DIC (13 μL, 0.080 mmol) at RT and the mixture stirred for 2 h at R.T. Another portion of (S)-2-(tert-butoxycarbonylamino)-3-methylbutanoic acid (2.5 mg) and DIC (8 μL) was added. The resulting mixture was heated at 35° C. for 5 min, then stirred at RT for ½ h. Evaporation, followed by purification by flash chromatography (12 g silica, 0% to 70% EtOAc-Hexanes) yielded Example 40A (31.3 mg) as a white solid. LC-MS, [M+H]$^+$=607.2.

Example 40

(S)—((R)-1-(5-(6-(4-Chlorophenyl)-4-oxopyrrolo[1,2-f][1,2,4]triazin-3(4H)-yl)pyridin-2-yl)pyrrolidin-3-yl) 2-amino-3-methylbutanoate, 2 TFA

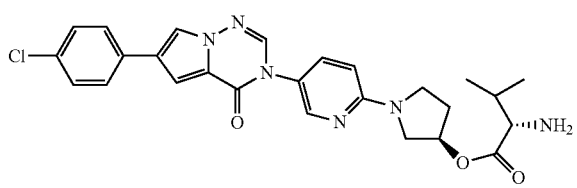 [SMILES: CC(C)[C@H](N)C(=O)O[C@@H]1CCN(c2ccc(-n3cnn4cc(-c5ccc(Cl)cc5)cc4c3=O)cn2)C1]

To a solution of Example 40A (30.5 mg, 0.050 mmol) in CH$_2$Cl$_2$ (2.5 mL) at room temperature was added TFA (0.75 mL). The resulting mixture was stirred at room temperature for 40 min. The solvent was evaporated to give a crude product which was further purified by preparative HPLC (PHENOMENEX® Luna Axia 5μ C18 30×100 mm; 10 min gradient from 70% A: 30% B to 0% A:100% B (A=90% H$_2$O/10% MeOH+0.1% TFA); (B=90% MeOH/10% H$_2$O+0.1% TFA); detection at 220 nm). The desired fraction was collected and concentrated under SPEEDVAC® to give Example 40 as white solid (26 mg, 69%). LC-MS, [M+H]$^+$=507.3. $^1$H NMR (CD$_3$OD, 400 MHz): δ 1.05-1.10 (m, 6H), 2.23-2.54 (m, 3H), 3.69-4.00 (m, 5H), 5.65-5.71 (m, 1H), 7.05-7.08 (m, 1H), 7.35-7.40 (m, 3H), 7.64-7.68 (m, 2H), 7.93 (s, 1H), 7.94-8.00 (m, 2H), 8.24 (d, J=2.0 Hz, 1H).

Example 41

(S)-2-(4-(6-(5-Chloropyridin-2-yl)-4-oxopyrrolo[1,2-f][1,2,4]triazin-3(4H)-yl)-2-methoxyphenoxy)-1-cyclopropylethyl 2-amino-3-methylbutanoate, 2 HCl

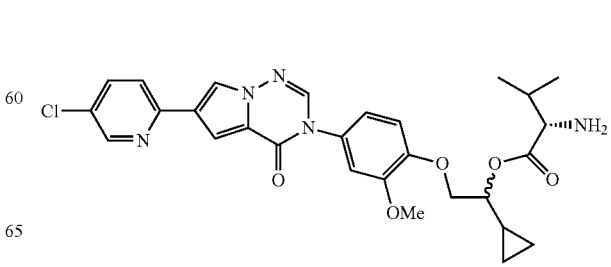

Example 41A (S)-2-(4-(6-(5-Chloropyridin-2-yl)-4-oxopyrrolo[1,2-f][1,2,4]triazin-3(4H)-yl)-2-methoxyphenoxy)-1-cyclopropylethyl 2-(tert-butoxycarbonylamino)-3-methylbutanoate

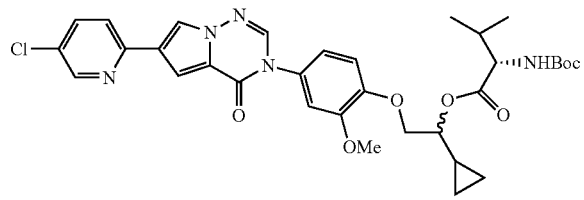 [SMILES: COc1cc(-n2cnn3cc(-c4ccc(Cl)cn4)cc3c2=O)ccc1OCC(OC(=O)[C@@H](NC(=O)OC(C)(C)C)C(C)C)C1CC1]

Example 41A was prepared from Example 29 using a procedure analogous to Example 40A above.

Example 41

(S)-2-(4-(6-(5-Chloropyridin-2-yl)-4-oxopyrrolo[1,2-f][1,2,4]triazin-3 (4H)-yl)-2-methoxyphenoxy)-1-cyclopropylethyl 2-amino-3-methylbutanoate, 2 HCl

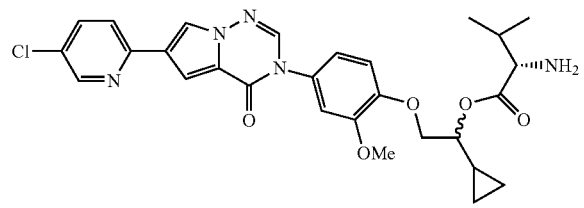 [SMILES: COc1cc(-n2cnn3cc(-c4ccc(Cl)cn4)cc3c2=O)ccc1OCC(OC(=O)[C@@H](N)C(C)C)C1CC1]

A mixture of Example 41A (27 mg, 0.041 mmol) in 4N HCl in dioxane (1.5 mL) was stirred at RT for 2 h. Most of the solvent was evaporated. The resulting slurry was diluted with Et$_2$O (20 mL). The mixture was stirred for 5 min and subjected to filtration. The solid was washed with Et$_2$O (2×10 mL), dried under vacuum to give Example 41 as a white solid (21 mg, 77%). LC-MS, [M+H]$^+$=552.5. $^1$H NMR (CD$_3$OD, 400 MHz): δ 0.48-0.75 (m, 4H), 1.08-1.20 (m, 6H), 1.20-1.35 (m, 1H), 2.25-2.40 (m, 1H), 3.83 (s, 1.5H), 3.86 (s, 1.5H), 3.92 (d, J=4.4 Hz, 0.5H), 4.01 (d, J=4.4 Hz, 0.5H), 4.30-4.38 (m, 2H), 4.70-4.85 (m, 1H), 6.99-7.17 (m, 2H), 7.60 (d, J=2.2 Hz, 1H), 8.01 (s, 1H), 8.05-8.19 (m, 2H), 8.28-8.30 (m, 1H), 8.67-8.70 (m, 1H).

Example 42

(S)—((R)-1-(4-(6-(5-Chloropyridin-2-yl)-4-oxopyrrolo[1,2-f][1,2,4]triazin-3(4H)-yl)-2-methoxyphenyl)pyrrolidin-3-yl) 2-amino-3-methylbutanoate, 2 HCl

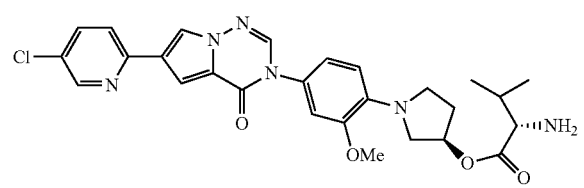 [SMILES: COc1cc(-n2cnn3cc(-c4ccc(Cl)cn4)cc3c2=O)ccc1N1CC[C@@H](OC(=O)[C@@H](N)C(C)C)C1]

Example 42 was prepared from Example 30 using a procedure analogous to Example 41 above. LC-MS, [M+H]$^+$=537.1 $^1$H NMR (CD$_3$OD, 400 MHz): δ 1.10 (d, J=7.1 Hz, 3H), 1.12 (d, J=7.1 Hz, 3H), 2.32-2.41 (m, 2H), 2.61-2.71 (m, 1H), 3.55-4.15 (m, 5H), 4.05 (s, 3H), 5.70 (bt, 1H), 7.15-7.20 (m, 1H), 7.37-7.39 (m, 1H), 7.58-7.72 (m, 2H), 8.08 (s, 1H), 8.13 (s, J=8.8 Hz, 1H), 8.25 (dd, J=8.8, 2.2 Hz, 1H), 8.32 (d, J=2.2 Hz, 1H), 8.72 (s, 0.5H), 8.73 (s, 0.5H).

Example 43

(S)-1-(5-(6-(4-Chlorophenyl)-4-oxopyrrolo[1,2-f][1,2,4]triazin-3(4H)-yl)pyridin-2-yl)piperidin-4-yl 2-amino-3-methylbutanoate, 2 HCl

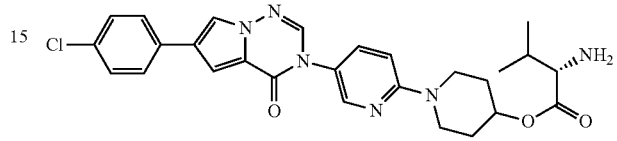

Example 43 was prepared from Example 18 using a procedure analogous to Example 41 above. LC-MS, [M+H]$^+$=521.5. $^1$H NMR (CD$_3$OD, 400 MHz): δ 1.11 (d, J=7.1 Hz, 6H), 1.90-2.03 (m, 2H), 2.15-2.26 (m, 2H), 2.30-2.40 (m, 1H), 3.80-3.90 (m, 2H), 3.95-4.06 (m, 3H), 5.29-5.36 (m, 1H), 7.37-7.40 (m, 2H), 7.41 (d, J=1.8 Hz, 1H), 7.52 (d, J=8.8 Hz, 1H), 7.65-7.70 (m, 2H), 7.98 (s, 1H), 8.00 (d, J=1.8 Hz, 1H), 8.10 (dd, J=8.8, 2.2 Hz, 1H), 8.32 (d, J=2.2 Hz, 1H).

Example 44

1-(4-(6-(5-Chloropyrimidin-2-yl)-4-oxopyrrolo[1,2-f][1,2,4]triazin-3(4H)-yl)-2-methoxyphenoxy)-2-methylpropan-2-yl 2-aminoacetate, HCl

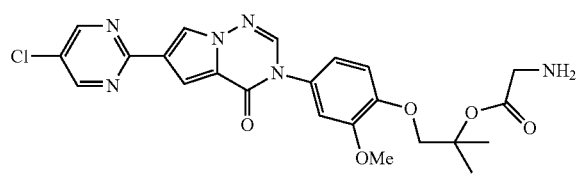 [SMILES: COc1cc(-n2cnn3cc(-c4ncc(Cl)cn4)cc3c2=O)ccc1OCC(C)(C)OC(=O)CN]

Example 44A 1-(4-(6-(5-Chloropyrimidin-2-yl)-4-oxopyrrolo[1,2-f][1,2,4]triazin-3 (4H)-yl)-2-methoxyphenoxy)-2-methylpropan-2-yl 2-(tert-butoxycarbonylamino)acetate

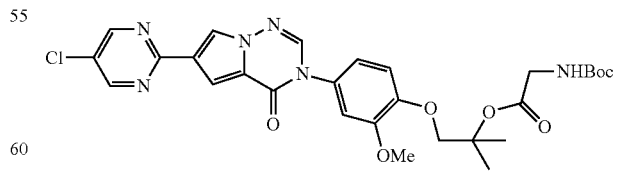

To a solution of Example 34 (8.8 mg, 0.020 mmol), 4-(pyrrolidin-1-yl)pyridine (4.43 mg, 0.030 mmol), and 2-(tert-butoxycarbonylamino)acetic acid (10.47 mg, 0.060 mmol) in DCM (0.332 mL) at 42° C. was added DIC (9.31 μL, 0.060 mmol, dissolved in 0.1 mL DCM) during a period of 1 h. The mixture was stirred at this temperature for 2 h at R.T. Another portion of 4-(pyrrolidin-1-yl)pyridine (4.43 mg, 0.030 mmol), and 2-(tert-butoxycarbonylamino)acetic acid (10.47 mg, 0.060 mmol) were added. DIC (9.31 µL, 0.060 mmol, dissolved in (0.1 mL DCM) was added at this temperature during a period of 1 h. The resulting mixture was stirred at RT for overnight. Hydrazine-H$_2$O (9.76 µL, 0.199 mmol) was added and the reaction was stirred at RT for 1 h, Evaporation, followed by purification by flash chromatography (12 g silica, 0% to 45% EtOAc-Hexanes) yielded Example 44A (9.24 mg, 77%) as a white solid. LC-MS, [M+H]$^+$=598.7

Alternative route: Example 44A was also prepared using a procedure analogous to Example 22 from (E)-4-(5-chloropyrimidin-2-yl)-1-(((dimethylamino)methyleneamino)-1H-pyrrole-2-carboxylic acid (Example 44F) and 1-(4-amino-2-methoxyphenoxy)-2-methylpropan-2-yl 2-(tert-butoxycarbonylamino)acetate (Example 22B).

Example 44B

Methyl 4-bromo-1-tosyl-1H-pyrrole-2-carboxylate

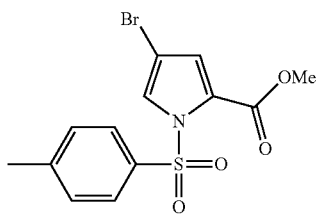 [SMILES: COC(=O)c1cc(Br)cn1S(=O)(=O)c1ccc(C)cc1]

To a solution of methyl 4-bromo-1H-pyrrole-2-carboxylate (2 g, 9.80 mmol) in DCM (20 mL) was added Et$_3$N (3 mL, 21.52 mmol), DMAP (127 mg, 1.040 mmol), and 4-methylbenzene-1-sulfonyl chloride (2.037 g, 10.68 mmol) portionwise at RT. The mixture was allowed to stir for 2.5 h at RT, diluted with DCM (100 mL) and washed with 1N HCl, brine, dried (Na$_2$SO$_4$), and evaporated under reduced pressure to obtain a golden oil, which was purified by flash chromatography (120 g, 0% to 100% EtOAc-Hexanes) to yield Example 44B (3.1 g, 8.65 mmol, 89% yield) as a white solid. $^1$H NMR (CDCl$_3$, 400 MHz): δ 7.9 (d, J=8.4 Hz, 2H), 7.7 (d, J=1.8 Hz, 1H), 7.4 (d, J=8.4 Hz, 2H), 7.0 (d, J=1.8 Hz, 1H), 3.7 (s, 3H), 2.4 (s, 3H). LC-MS, [M+H]$^+$=357.8/359.8.

Example 44C

Methyl 4-(5,5-dimethyl-1,3,2-dioxaborinan-2-yl)-1-(tosylsulfonyl)-1H-pyrrole-2-carboxylate

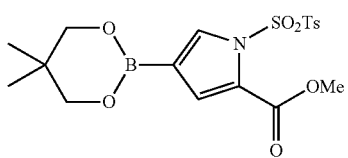

A mixture of DMSO (80 mL) and dioxane (80 mL) was degassed for 30 min. The above degassed solution was then added to Example 44B (10 g, 27.9 mmol), 5,5,5',5'-tetramethyl-2,2'-bi(1,3,2-dioxaborinane) (8.82 g, 39.0 mmol) and potassium acetate (6.85 g, 69.8 mmol) in a seal tube. The above mixture was degassed for additional 15 mins. Pd(dppf)Cl$_2$ (2.280 g, 2.79 mmol) was weighed and quickly transferred in to the above mixture and the tube was sealed. The reaction mixture was then heated to 80° C. for 4 h. The reaction mixture diluted with ether (1000 mL) and washed with water (330 mL). The organic layer was separated and dried over MgSO$_4$ to give the crude product which was purified by flash chromatography (330 g silica, 0% to 50% EtOAc-Hexanes) yielded Example 44C (6.38 g, 58%) as a white solid. $^1$H NMR (CDCl$_3$, 400 MHz): δ 1.01 (s, 6H), 2.41 (s, 3H), 3.71 (s, 3H), 3.72 (s, 4H), 7.27 (d, J=1.7 Hz, 1H), 7.29-7.32 (m, 2H), 7.86-7.90 (m, 2H), 8.02 (d, J=1.7 Hz, 1H).

Example 44D

Methyl 4-(5-chloropyrimidin-2-yl)-1-(tosylsulfonyl)-1H-pyrrole-2-carboxylate

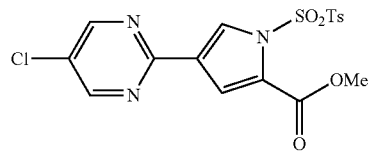

Toluene (60 mL) was degassed for 30 min. The above degassed solvent was then added to 5-chloro-2-iodopyrimidine (2.560 g, 10.65 mmol), Example 44C (4.95 g, 12.65 mmol) and sodium carbonate (2.28 g, 21.30 mmol). Then tetrabutylammonium hydroxide solution (2.3 mL, 40% wt solution in water) and H$_2$O (6 mL) were added. PdCl$_2$(dppf)-CH$_2$Cl$_2$ adduct (870 mg, 1.065 mmol) was weighed and quickly transferred in to the above mixture and the seal tube was resealed. The reaction mixture was then heated to 100° C. for 3 h. Solvent was evaporated. The residue was diluted with EtOAc (300 mL), washed with H$_2$O (80 mL). The organic layer was separated and concentrated to give crude product which was further purified by flash chromatography (220 g silica, 0% to 25% EtOAc-Hexanes) yielded Example 44D (3.4 g, 82%) as a beige solid. LC-MS, [M+H]$^+$=392.2. $^1$H NMR (CDCl$_3$, 400 MHz): δ 2.44 (s, 3H), 3.78 (s, 3H), 7.31-7.36 (m, 2H), 7.68 (d, J=1.7 Hz, 1H), 7.94-7.98 (m, 2H), 8.51 (d, J=1.7 Hz, 1H), 8.66 (s, 2H).

Example 44E

Methyl 4-(5-chloropyrimidin-2-yl)-1H-pyrrole-2-carboxylate

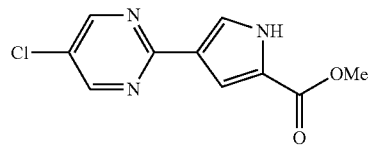 [SMILES: COC(=O)c1cc(-c2ncc(Cl)cn2)c[nH]1]

A mixture of Example 44D (309 mg, 0.789 mmol) in sodium methoxide (10.00 mL, 5.00 mmol, 0.5 M in MeOH) was stirred at RT for 2 h. The mixture was diluted with EtOAc (70 mL) and aq. 1N HCl (5 mL). The mixture was washed with H$_2$O (30 mL). The organic layer was separated, dried over MgSO$_4$ and concentrated to give the product. The product was further triturated with MeOH to yield Example 44E (150 mg, 80%) as a white solid. LC-MS, [M+H]$^+$=238.1. $^1$H NMR (CDCl₃, 400 MHz): δ 3.89 (s, 3H), 7.57-7.59 (m, 1H), 7.74-7.77 (m, 1H), 8.60 (s, 2H), 9.32 (bs, 1H).

Example 44F (E)-4-(5-Chloropyrimidin-2-yl)-1-((dimethylamino) methyleneamino)-1H-pyrrole-2-carboxylic acid

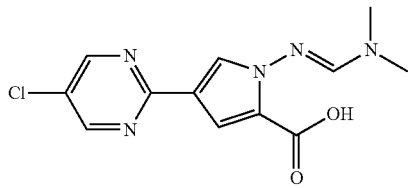 [SMILES: CN(C)/C=N/n1cc(-c2ncc(Cl)cn2)cc1C(=O)O]

Example 44F was prepared from Example 44E using a procedure analogous to Example 18A above. LC-MS, [M+H]⁺=238.1. ¹H NMR (DMSO-d₆, 400 MHz): δ 2.87 (s, 3H), 2.99 (s, 3H), 7.26 (s, 1H), 7.79-7.82 (m, 1H), 8.21-8.25 (m, 1H), 8.77 (s, 2H).

Example 44

1-(4-(6-(5-Chloropyrimidin-2-yl)-4-oxopyrrolo[1,2-f][1,2,4]triazin-3(4H)-yl)-2-methoxyphenoxy)-2-methylpropan-2-yl 2-aminoacetate, HCl

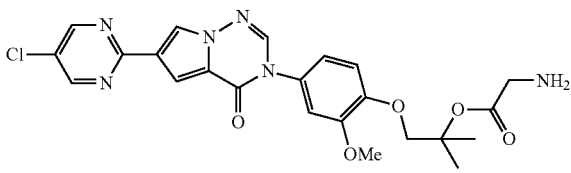 [SMILES: COc1cc(-n2cnn3cc(-c4ncc(Cl)cn4)cc3c2=O)ccc1OCC(C)(C)OC(=O)CN]

Example 44 was prepared using a procedure analogous to Example 41 above. LC-MS, [M+H]⁺=499.2. ¹H NMR (CD₃OD, 400 MHz): δ 1.64 (s, 6H), 3.70 (s, 2H), 3.87 (s, 3H), 4.30 (s, 2H), 7.00 (dd, J=8.8, 2.2 Hz, 1H), 7.10-7.15 (m, 2H), 7.69 (d, J=2.2 Hz, 1H), 7.96 (s, 1H), 8.22 (d, J=2.2 Hz, 1H), 8.77 (s, 2H).

Example 45

6-(4-Chlorophenyl)-3-(4-((3,3-difluoro-1-hydroxy-cyclobutyl)methoxy)-3-methoxyphenyl)pyrrolo[1,2-f][1,2,4]triazin-4(3H)-one

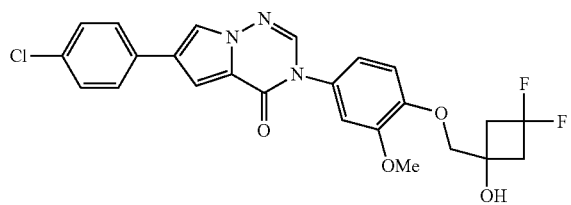 [SMILES: COc1cc(-n2cnn3cc(-c4ccc(Cl)cc4)cc3c2=O)ccc1OCC1(O)CC(F)(F)C1]

Example 45A 3,3-Difluoro-N,N-dimethylcyclobutanecarboxamide

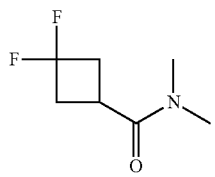

Oxalyl chloride (21.74 mL, 248 mmol) was added dropwise to a stirred solution of 3,3-difluorocyclobutanecarboxylic acid (26 g, 191 mmol; prepared as described in ref: Elend, D. et al., Syn. Comm., 35:657 (2005)) in CH₂Cl₂ (500 mL) and DMF (0.5 mL) at 0° C. The reaction mixture was allowed to come to RT and stirred at RT for 1 h prior to being concentrated at RT using a rotary evaporator at ca. 50 mm Hg vacuum. After adding THF (300 mL) to the resulting residue, the stirred solution was cooled 0° C. prior to addition of a 2M solution of Me₂NH (478 mL, 955 mmol) in THF. After stirring the reaction mixture at RT for 0.5 h, the mixture was partitioned between ether and 5% aq. Na₂CO₃. The organic layer was dried over MgSO₄ and concentrated in vacuo at RT. After portioning the residue between CH₂Cl₂ and water, the organic layer was dried over MgSO₄ and concentrated in vacuo at RT to give 3,3-difluoro-N,N-dimethylcyclobutanecarboxamide (24 g, 147 mmol, 77% yield) as a brown semi solid, used as such in the next step. ¹H NMR (400 MHz, CDCl₃) δ ppm 2.82-3.13 (9H, m), 2.62-2.79 (2H, m).

Example 45B 1-(3,3-Difluorocyclobutyl)-N,N-dimethylmethanamine

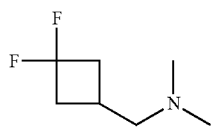

A solution of 3,3-difluoro-N,N-dimethylcyclobutanecarboxamide (24 g, 147 mmol) prepared in Part A in THF (500 mL) was added to a stirred suspension of lithium aluminum hydride (7.5 g, 198 mmol) in 500 mL THF at 0° C. The mixture was allowed to come to RT. After stirring the reaction mixture at RT for 18 h, it was quenched by slowly adding 10 mL 6 N NaOH and 5 mL water at 5° C. with stirring. The mixture was stirred at RT for 0.5 h, dried over Na₂SO₄ and filtered. The filtrate was concentrated to ca. 30 mL by a careful distillation of most of the THF using a Vigreux column. The remaining material was distilled under slightly reduced pressure (ca. 100-200 mm Hg); the fraction (20 mL, by 70-90° C.) contained the title compound contaminated with THF. The residual THF was carefully purged with a gentle stream of nitrogen to yield 1-(3,3-difluorocyclobutyl)-N,N-dimethylmethanamine (12 g, 80 mmol, 54.7% yield). ¹H NMR (400 MHz, CDCl$_3$) δ ppm 2.46-2.94 (2H, m), 2.38 (2H, d, J=6.55 Hz), 2.16-2.28 (9H, m).

Example 45C 1-(3,3-Difluorocyclobutyl)-N,N-dimethylmethanamine oxide hydrate

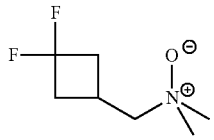

Ref Cope, A. C. et al., *Org. Syn. Coll., IV*:612-615; Doering et al., *J. Am. Chem. Soc.,* 89(17):4534 (1967).

30% Aqueous H$_2$O$_2$ (18 mL) was added dropwise to a stirred solution of 1-(3,3-difluorocyclobutyl)-N,N-dimethylmethanamine (12 g, 80 mmol) prepared in Part B in methanol (100 mL) at 5 to 22° C. over 2 h. After stirring at RT for 20 h, additional 30% H$_2$O$_2$ (18 mL) was added. After 3 h, Pd black slurry (150 mg) in water (3 mL) was added to the stirred reaction mixture in small portions such that the temperature could be maintained between 5 to 25° C. with a cooling bath. The reaction mixture was stirred at RT for 1 h until the O$_2$ evolution ceased. After filtration, the filtrate was concentrated in vacuo to give 1-(3,3-difluorocyclobutyl)-N,N-dimethylmethanamine oxide hydrate as a thick colorless oil (15 g, semisolid). $^1$H NMR (400 MHz, CD$_3$OD) δ ppm 3.47 (2H, d, J=5.29 Hz), 3.16 (6H, s), 2.75-2.92 (3H, m), 2.42-2.58 (2H, m).

Example 45D 1,1-Difluoro-3-methylenecyclobutane

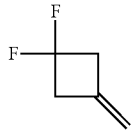

In order to remove most of the water from the sample, 1-(3,3-difluorocyclobutyl)-N,N-dimethylmethanamine oxide hydrate (15 g, 91 mmol) prepared in Part C was heated under vacuum (10 mm) at 100° C. using a distillation setup with the receiving flask cooled to −78° C. Once the water had been removed, the temperature was gradually increased to 165° C. After ca. 1 h most of the starting material had been pyrolized (a small amount of dark brown material remained in the distillation flask). Contents of the receiving flask were then washed sequentially with 5% aq. HCl (3×3 mL) and sat. NaHCO$_3$ (5 mL). The organic layer (olefin) was filtered through Na$_2$SO$_4$ giving 1,1-difluoro-3-methylenecyclobutane (5.5 g, 52.8 mmol, 58.2% yield) as a colorless oil. $^1$H NMR (400 MHz, CDCl$_3$) δ ppm 5.10 (2H, quin, J=2.52 Hz), 2.77-3.57 (4H, m).

Example 45E 5,5-Difluoro-1-oxaspiro[2.3]hexane

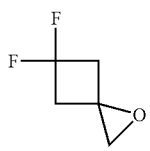

Meta chloroperbenzoic acid (74.6 g, 303 mmol) was added in small portions to a stirred solution of 1,1-difluoro-3-methylenecyclobutane (21.0 g, 202 mmol) prepared in Part D in CH$_2$Cl$_2$ (600 mL) at RT. The reaction mixture cooled with a water bath during the addition. After ca. 1 h the onset of a slight exotherm prompted further cooling using ice-water mixture. The reaction mixture was allowed to come to RT over 3 h. After stirring at RT for 16 h, additional m-CPBA (10 g) was added. The reaction mixture was stirred at RT for 24 h prior to being stored overnight in a refrigerator at 4° C. to precipitate out some of the acids. After filtration, the filtrate was washed with 10% Na$_2$CO$_3$. The organic layer was dried (Na$_2$SO$_4$), concentrated to ca. 170 mL using a Vigreux column. This material was flash distilled at ca. 10 mm to −78° C. traps (two traps in series were employed to minimize loss). The distillate was concentrated using a Vigreux column to a volume of approximately 50 mL affording a 3:1 mixture of CH$_2$Cl$_2$: 5,5-difluoro-1-oxaspiro[2.3]hexane (80 g, 200 mmol, 99% yield) by NMR. This material was used without further purification in the next step. $^1$H NMR (400 MHz, CDCl$_3$ δ ppm 2.91-3.16 (4H, m), 2.88 (2H, s).

Example 45F 3,3-Difluoro-1-((2-methoxy-4-nitrophenoxy)methyl)cyclobutanol

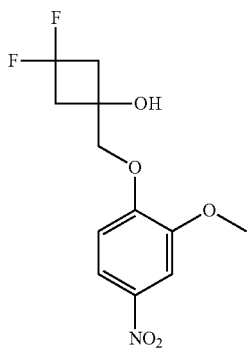 [SMILES: COc1cc(N)ccc1OCC1(O)CC(F)(F)C1]

A mixture of 5,5-difluoro-1-oxaspiro[2.3]hexane+3 eq. CH$_2$Cl$_2$ (22.52 g, 0.06 mol), potassium 2-methoxy-4-nitrophenolate (12.43 g, 0.060 mol) prepared in Part E and NaH$_2$PO$_4$·H$_2$O (7.45 g, 0.054 mol) in 50 mL MeCN-water (85:15) was heated at 130° C. in a steel bomb for 3.5 h. The reaction mixture was diluted with EtOAc, washed with 5% Na$_2$CO$_3$, dried (MgSO$_4$) and concentrated. The crude product was recrystallized from ca. 150 mL MTBE giving 3,3-difluoro-1-((2-methoxy-4-nitrophenoxy)methyl)cyclobutanol (11.2 g, 0.039 mol, 64.5% yield) as a light yellow solid. An additional 1.2 g of a slightly less pure desired product was obtained upon concentration of the mother liquor to ca. 50 mL. $^1$H NMR (400 MHz, CDCl$_3$) δ ppm 7.89 (1H, dd, J=8.94, 2.64 Hz), 7.76 (1H, d, J=2.77 Hz), 6.95 (1H, d, J=9.06 Hz), 4.16 (2H, s), 3.94 (3H, s), 3.36 (1H, s), 2.73-2.92 (4H, m).

Example 45G 1-((4-Amino-2-methoxyphenoxy)methyl)-3,3-difluorocyclobutanol

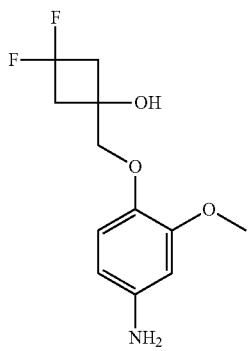

A mixture of 3,3-difluoro-1-((2-methoxy-4-nitrophenoxy)methyl)cyclobutanol (32.0 g, 111 mmol) prepared in Part F and 10% Pd/C (2.0 g, 1.879 mmol) in 700 mL MeOH was stirred under H$_2$ at 50 psi for 1.5 h. After filtration, the filtrate was concentrated to give 1-((4-amino-2-methoxyphenoxy)methyl)-3,3-difluorocyclobutanol (28.9 g, 111 mmol, quantitative yield) as a light purple solid. $^1$H NMR (400 MHz, CD$_3$OD) δ ppm 6.68 (1H, d, J=8.56 Hz), 6.35 (1H, d, J=2.52 Hz), 6.16 (1H, dd, J=8.31, 2.52 Hz), 4.77 (3H, br. s.), 3.78 (2H, s), 3.68 (3H, s), 2.68-2.82 (2H, m), 2.38-2.56 (2H, m).

Example 45

6-(4-Chlorophenyl)-3-(4-((3,3-difluoro-1-hydroxycyclobutyl)methoxy)-3-methoxyphenyl)pyrrolo[1,2-f][1,2,4]triazin-4(3H)-one

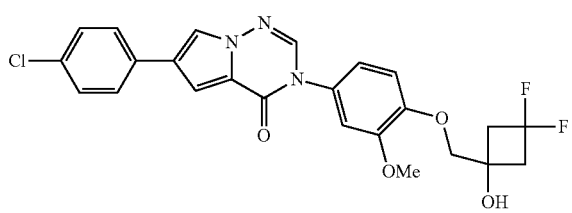

Example 45 was prepared from Example 18A and 1-((4-amino-2-methoxyphenoxy)methyl)-3,3-difluorocyclobutanol (Example 45G) using a procedure analogous to Example 18 above. LC-MS, [M+H]$^+$=488.4. $^1$H NMR (DMSO-d$_6$, 400 MHz): δ 2.53-2.68 (m, 2H), 2.80-2.92 (m, 2H), 3.78 (s, 3H), 3.99 (s, 2H), 5.83 (s, 1H), 7.03 (dd, J=8.8, 2.2 Hz, 1H), 7.14 (d, J=8.8 Hz, 1H),), 7.20 (d, J=2.2 Hz, 1H), 7.40-7.46 (m, 2H), 7.48 (d, J=2.2 Hz, 1H), 7.82-7.86 (m, 2H), 8.12 (s, 1H), 8.26 (d, J=2.2 Hz, 1H).

Example 46

6-(5-Chloropyridin-2-yl)-3-(4-((3,3-difluoro-1-hydroxycyclobutyl)methoxy)-3-methoxyphenyl)pyrrolo[1,2-f][1,2,4]triazin-4(3H)-one-4(3H)-one

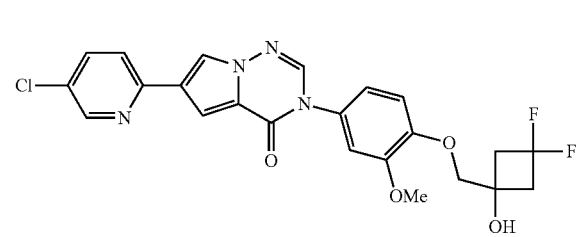 [SMILES: COc1cc(-n2cnn3cc(-c4ccc(Cl)cc4)cc3c2=O)ccc1OCC1(O)CC(F)(F)C1]

Example 46A (E)-4-(5-Chloropyridin-2-yl)-1-((dimethylamino)methyleneamino)-1H-pyrrole-2-carboxylic acid

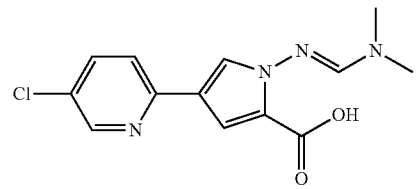 [SMILES: CN(C)/C=N/n1cc(-c2ccc(Cl)cn2)cc1C(=O)O]

Example 46A was prepared in a manner similar to Example 44F. LC-MS, [M+H]$^+$=293.0. $^1$H NMR (DMSO-d$_6$, 400 MHz): δ 8.40 (d, J=2.20 Hz, 1H), 8.09 (s, 1H), 7.66 (d, J=2.20 Hz, 1H), 7.60 (dd, J=8.52, 2.47 Hz, 1H), 7.42 (d, J=8.79 Hz, 1H), 3.13 (br s, 2H), 3.03 (br s, 2H).

Example 46

6-(5-Chloropyridin-2-yl)-3-(4-((3,3-difluoro-1-hydroxycyclobutyl)methoxy)-3-methoxyphenyl)pyrrolo[1,2-f][1,2,4]triazin-4(3H)-one-4(3H)-one

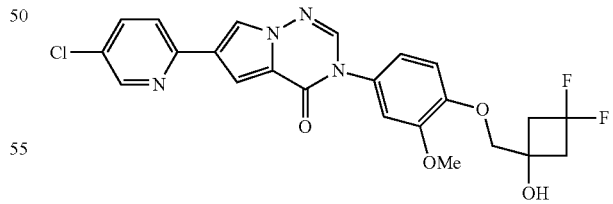

Example 46 was prepared from Example 46A and 1-((4-amino-2-methoxyphenoxy)methyl)-3,3-difluorocyclobutanol (Example 45G) using a procedure analogous to Example 18 above. LC-MS, [M+H]$^+$=489.0. $^1$H NMR (DMSO-d$_6$, 400 MHz): δ 2.53-2.68 (m, 2H), 2.80-2.92 (m, 2H), 3.78 (s, 3H), 3.99 (s, 2H), 5.83 (s, 1H), 7.02-7.07 (m, 1H), 7.12-7.15 (m, 1H), 7.18-7.22 (m, 1H), 7.56-7.59 (m, 1H), 7.93-8.00 (m, 2H), 8.14-8.16 (m, 1H), 8.27-8.30 (m, 1H), 8.58-8.61 (m, 1H).

Example 47

6-(4-Chlorophenyl)-3-(4-(2,3-dihydroxy-2-methyl-propoxy)-3-methoxyphenyl)pyrrolo[1,2-f][1,2,4]triazin-4(3H)-one

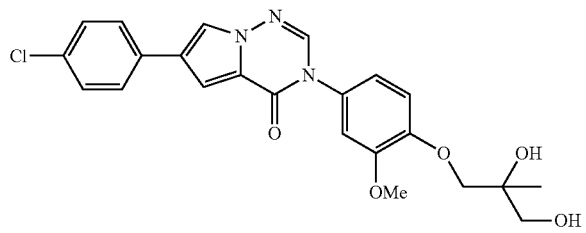 [SMILES: COc1cc(-n2cnn3cc(-c4ccc(Cl)cc4)cc3c2=O)ccc1OCC(C)(O)CO]

Example 47 was prepared from Example 18A and 3-(4-amino-2-methoxyphenoxy)-2-methylpropane-1,2-diol, (see US 2007/0093509) using a procedure analogous to Example 18 above. LC-MS, [M+H]$^+$=456.0. $^1$H NMR (DMSO-d$_6$, 400 MHz): δ 1.15 (s, 3H), 3.30-3.45 (m, 2H), 3.78 (d, J=9.2 Hz, 1H), 3.79 (s, 3H), 3.89 (d, J=9.2 Hz, 1H), 4.57 (s, 1H), 4.68 (d, J=5.7 Hz, 1H), 7.02 (dd, J=8.8, 2.2 Hz, 1H), 7.09 (d, J=8.8 Hz, 1H), 7.16 (d, J=2.2 Hz, 1H), 7.42-7.46 (m, 2H), 7.48 (d, J=2.2 Hz, 1H), 7.80-7.85 (m, 2H), 8.12 (s, 1H), 8.28 (d, J=1.8 Hz, 1H).

Example 48

(R)-6-(5-Chloropyridin-2-yl)-3-(4-(2-cyclopropyl-2-hydroxyethoxy)-3-methoxyphenyl)pyrrolo[1,2-f][1,2,4]triazin-4(3H)-one

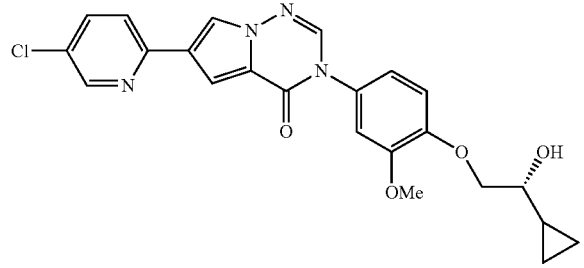 [SMILES: COc1cc(-n2cnn3cc(-c4ccc(Cl)cn4)cc3c2=O)ccc1OC[C@H](O)C1CC1]

Example 48A

2-Bromo-1-cyclopropylethanone

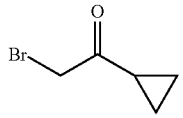

Following the procedure described by Calverley, M. J. et al., *Tetrahedron Lett.*, 43:4609 (1987), Br$_2$ (21.72 mL, 422 mmol) was added over 5 min to a solution of 1-cyclopropylethanone (35.44 g, 421 mmol) in MeOH (250 mL) at 0° C. Decolorization occurred as the resulting dark orange solution was stirred at <10° C. for 50 min. After removal of the ice bath, the mixture was stirred at 20° C. for another 0.5 h; whereupon, 30 ml of water was added. After stirring an additional 15 min, the reaction was diluted with 90 ml water prior to extraction with 200 mL of Et$_2$O (4×). The combined organic layers were sequentially washed with 1M Na$_2$CO$_3$ (150 ml) and brine (100 ml) before drying over anhy. MgSO$_4$.

After filtration and concentration using a rotary evaporator, the crude product was obtained as colorless oil. Subsequent distillation at 13 mm Hg yielded 40.9 g of 2-bromo-1-cyclopropylethanone as a colorless oil by 58-62° C. $^1$H NMR (500 MHz, CDCl$_3$) δ ppm 0.95-1.03 (m, 2H), 1.08-1.15 (m, 2H), 2.13-2.21 (m, 1H), 4.00 (s, 2H).

Example 48B

1-Cyclopropyl-2-(2-methoxy-4-nitrophenoxy)ethanone

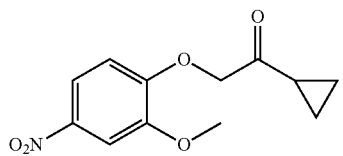 [SMILES: COc1cc([N+](=O)[O-])ccc1OCC(=O)C1CC1]

An orange suspension of 4-nitroguaiacol potassium salt hydrate (31.7 g, 153 mmol) and 2-bromo-1-cyclopropylethanone (29.4 g, 180 mmol), prepared in Example 48A, in DMF (310 mL) was heated at 80° C. for 1 h. LC-MS analysis revealed the conversion to product was complete. The resulting yellow reaction mixture was diluted with water (932 ml) and stirred for 4 hr as the mixture cooled to 20° C. Subsequent filtration yielded a yellow filter cake which after washing 3× with 150 mL of H$_2$O and air drying yielded 34.6 g of 1-cyclopropyl-2-(2-methoxy-4-nitrophenoxy)ethanone as a light yellow solid. M.P. 112-113° C. $^1$H NMR (400 MHz, CDCl$_3$): δ ppm 0.95-1.03 (m, 2H), 1.13-1.18 (m, 2H), 2.15-2.23 (m, 1H), 3.95 (s, 3H), 4.86 (s, 2H), 6.73 (d, J=8.7 Hz, 1H), 7.75 (d, J=2.7 Hz, 1H), 7.82 (dd, J=8.7, 2.7 Hz, 1H). $^{13}$C NMR (100 MHz, CDCl$_3$) δ ppm 205.2, 152.7, 149.1, 117.3, 111.6, 106.9, 73.5, 56.3, 17.1, 12.0. HPLC: 5.8 min retention time, 98.7% API; ZORBAX® column SB C18 4.6×75 mm; flow rate 2.5 ml/min; Gradient solvent system: from 100% A:0% B to 0% A:100% B for 8 min (Solvent A: 10% MeOH-90% H$_2$O=0.2% H$_3$PO$_4$; Solvent B: 90% MeOH-10% H$_2$O+0.2% H$_3$PO$_4$) Detection at 220 nm. LC/MS: m/e 252.3 (M+H); 4 min gradient; 2.35 min retention.

Example 48C (R)-1-Cyclopropyl-2-(2-methoxy-4-nitrophenoxy)ethanol

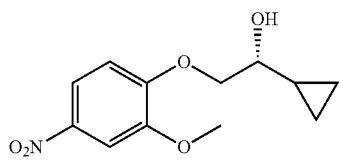

To a yellow suspension of 1-cyclopropyl-2-(2-methoxy-4-nitrophenoxy)ethanone (34.6 g, 138 mmol) in EtOH (356 mL) at 0° C. was added NaBH$_4$ (3.1 g, 82 mmol) over 15 min. After removal of the ice bath, the temperature was not allowed to exceed 20° C. while the reaction stirred for 35 additional min. During this period the color progressively became a deeper yellow hue. The stirred reaction was cooled to ~10° C. using an ice bath prior to cautious slow addition of HOAc (12 mL, 210 mmol) to minimize the rate of evolution of H$_2$ gas.

After stirring for 0.5 h following cessation of gas evolution, the yellow suspension was concentrated under vacuum using a rotary evaporator to remove ~300 mL of EtOH. Filtration yielded a light yellow solid (28.7 g) after washing with $H_2O$ and air drying. Subsequent further concentration of the filtrate to remove most of the EtOH resulted in more precipitate forming which, after filtration as described previously, corresponded to an additional 4.9 g of desired product. The two fractions were combined to yield 33.6 g of racemic 1-cyclopropyl-2-(2-methoxy-4-nitrophenoxy)ethanol.

Racemic 1-cyclopropyl-2-(2-methoxy-4-nitrophenoxy)ethanol (45.1 g, mmol) in 2/1 MeCN/1-PrOH (451 mL) was resolved by chiral chromatography resolution using a CHIRALPAK® AD-H (3×25 cm, 5 µm) column under the Chiral-SFC conditions. The chromatographic conditions employed an 85/15 mixture of $CO_2$/i-PrOH as the mobile solvent with a flow rate of 130 mL/min at 35° C. with the BPR pressure maintained at 100 bar and detector wavelength at 234 nM. Each 0.7 mL injection required a run time of 7 min. The chiral purity of the R enantiomer was determined to be greater than 99.9% at 234 nm based on SFC/UV area % using analytical SFC conditions. Concentration of the resultant eluant under vacuum using a rotary evaporator yielded (R)-1-cyclopropyl-2-(2-methoxy-4-nitrophenoxy)ethanol as yellow oil. Subsequent dissolution in 150 ml EtOH and reconcentration yielded the title compound in the form of a yellow oil, which solidified to form a light yellow solid (20.9 g) upon drying under high vacuum overnight. M.P. 77° C. $^1$H NMR (400 MHz, CDCl$_3$): δ ppm 0.30-0.37 (m, 1H), 0.42-0.50 (m, 1H), 0.55-0.69 (m, 2H), 0.97-1.08 (m, 1H), 2.40-2.70 (bs, 1H), 3.41 (ddd, J=8.3, 8.3, 2.7 Hz, 1H), 3.93 (s, 3H), 4.10 (dd, J=9.3, 8.0 Hz, 1H), 4.23 (dd, J=9.3, 2.7 Hz, 1H), 6.95 (d, J=8.8 Hz, 1H), 7.74 (d, J=2.2 Hz, 1H), 7.89 (dd, J=8.8, 2.2 Hz, 1H). $^{13}$C NMR (100 MHz, CDCl$_3$) δ ppm 153.7, 149.2, 141.7, 117.6, 111.5, 106.7, 74.4, 73.5, 56.2, 13.4, 2.7, 2.0. HPLC: 6.26 min retention time, 98.7% API; ZORBAX® column SB C18 4.6×75 mm; flow rate 2.5 ml/min; Gradient solvent system: from 100% A:0% B to 0% A:100% B for 8 min (Solvent A: 10% MeOH-90% $H_2O$=0.2% $H_3PO_4$; Solvent B: 90% MeOH-10% $H_2O$+0.2% $H_3PO_4$) Detection at 220 nm. LC/MS: m/e=254.3 (M+H).

Chiral HPLC: Optical purity was assessed by HPLC chromatography at 35° C. using a CHIRALPAK® AD-H, 25×4 6 mm ID; 5 µm column for which the mobile phase was a 80/20 mixture of $CO_2$/isopropanol at 100 bars with a flow rate of 2 mL/min. Under these conditions the desired R enantiomer eluted in 7 minutes followed by the S enantiomer at 8.5 min.

Example 48D (R)-2-(4-Amino-2-methoxyphenoxy)-1-cyclopropylethanol

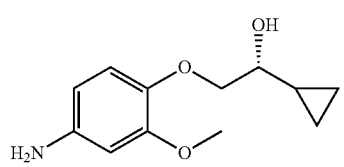 [SMILES: COc1cc([N+](=O)[O-])ccc1OC[C@H](O)C1CC1]

To a solution of (R)-1-cyclopropyl-2-(2-methoxy-4-nitrophenoxy)ethanol (20.90 g, 83 mmol) in EtOH (546 ml) was added 5% Pd/C, dry basis, Degussa type 50% water content (3.0 g, 0.705 mmol). The suspension was hydrogenated (1 atm. $H_2$, balloon) at 20° C. for 2.5 h; whereupon, LC/MS analysis revealed the reaction to be complete. After filtration of the reaction mixture through Celite pad and subsequent washing of the cake with EtOH, the filtrate was concentrated under vacuum using a rotary evaporator to yield (R)-2-(4-amino-2-methoxyphenoxy)-1-cyclopropylethanol as a brown solid. M.P. 71° C. (18.34 g, 100%). $^1$H NMR (400 MHz, CDCl$_3$): δ ppm 0.18-0.27 (m, 1H), 0.38-0.43 (m, 1H), 0.45-0.61 (m, 2H), 0.82-0.92 (m, 1H), 3.21 (ddd, J=8.8, 8.8, 2.6 Hz, 1H), 3.80 (s, 3H), 3.86 (dd, J=10.1, 8.8 Hz, 1H), 4.09 (dd, J=10.1, 2.6 Hz, 1H), 6.21 (dd, J=8.3, 2.7 Hz, 1H). 6.29 (d, J=2.7 Hz, 1H), 6.78 (d, J=8.3 Hz, 1H). $^{13}$C NMR (100 MHz, CDCl$_3$) δ ppm 151.2, 142.1, 140.8, 118.7, 106.9, 100.5, 76.5, 74.4, 55.7, 12.9, 2.5, 1.6. HPLC: 6.28 min retention time, 98.5% API; ZORBAX® column SB C18 4.6×75 mm; flow rate 2.5 ml/min; Gradient solvent system: from 100% A:0% B to 0% A:100% B for 8 min (Solvent A: 10% MeOH-90% $H_2O$=0.2% $H_3PO_4$; Solvent B: 90% MeOH-10% $H_2O$+0.2% $H_3PO_4$) Detection at 220 nm. LC/MS: m/e 224.5 (M+H); 4 min gradient.

Example 48

(R)-6-(5-Chloropyridin-2-yl)-3-(4-(2-cyclopropyl-2-hydroxyethoxy)-3-methoxyphenyl)pyrrolo[1,2-f][1,2,4]triazin-4(3H)-one

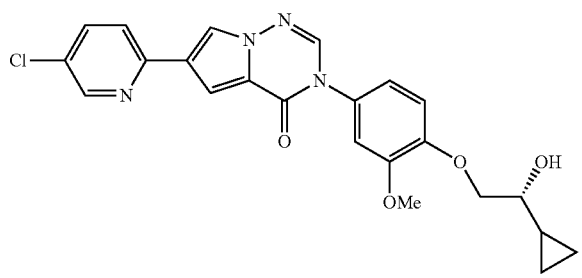 [SMILES: COc1cc(-n2cnn3cc(-c4ccc(Cl)cn4)cc3c2=O)ccc1OC[C@H](O)C1CC1]

Example 48 was prepared from Example 46A and (R)-2-(4-amino-2-methoxyphenoxy)-1-cyclopropylethanol (Example 48D) using a procedure analogous to Example 18 above. LC-MS, [M+H]$^+$=453.4. $^1$H NMR (DMSO-d$_6$, 400 MHz): δ 0.29-0.43 (m, 4H), 0.90-1.00 (m, 1H), 3.30-3.40 (m, 1H), 3.77 (s, 3H), 3.94-4.02 (m, 2H), 4.89 (d, J=5.5 Hz, 1H), 7.02 (dd, J=8.8, 2.2 Hz, 1H), 7.11 (d, J=8.8 Hz, 1H), 7.18 (d, J=2.2 Hz, 1H), 7.58 (d, J=1.8 Hz, 1H), 7.92-8.00 (m, 2H), 8.17 (s, 1H), 8.29 (d, J=1.8 Hz, 1H), 8.60-8.62 (m, 1H).

Example 49

(R)-2-(4-(6-(5-Chloropyridin-2-yl)-4-oxopyrrolo[1,2-f][1,2,4]triazin-3(4H)-yl)-2-methoxyphenoxy)-1-cyclopropylethyl 2-aminoacetate, 2 TFA

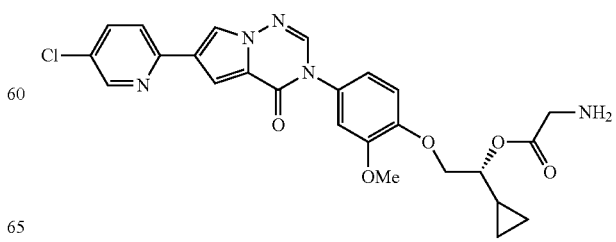

Example 49A (R)-2-(4-(6-(5-Chloropyridin-2-yl)-4-oxopyrrolo[1,2-f][1,2,4]triazin-3(4H)-yl)-2-methoxyphenoxy)-1-cyclopropylethyl 2-(tert-butoxycarbonylamino)acetate

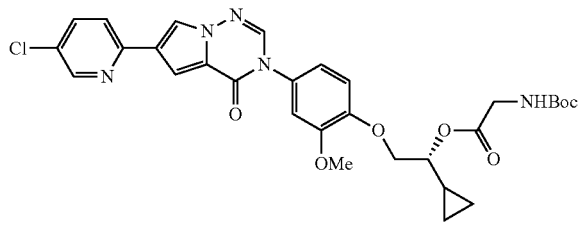 [SMILES: COc1cc(-n2cnn3cc(-c4ccc(Cl)cn4)cc3c2=O)ccc1OC[C@H](OC(=O)CNC(=O)OC(C)(C)C)C1CC1]

To a solution of Example 48 (23.3 mg, 0.051 mmol), DMAP (1.500 mg, 0.012 mmol), and 2-(tert-butoxycarbonylamino)acetic acid (11.72 mg, 0.067 mmol) in DCM (0.4 mL) was added DIC (13 µL, 0.080 mmol) at RT. The resulting mixture was heated to reflux for 1 min. then stirred at RT for 2 h. Evaporation, followed by purification by flash chromatography (12 g silica, 0% to 50% EtOAc-Hexanes) yielded Example 49A (23 mg, 73%) as a white solid. LC-MS, [M+H]$^+$=610.5.

Example 49

(R)-2-(4-(6-(5-Chloropyridin-2-yl)-4-oxopyrrolo[1,2-f][1,2,4]triazin-3(4H)-yl)-2-methoxyphenoxy)-1-cyclopropylethyl 2-aminoacetate, 2 TFA

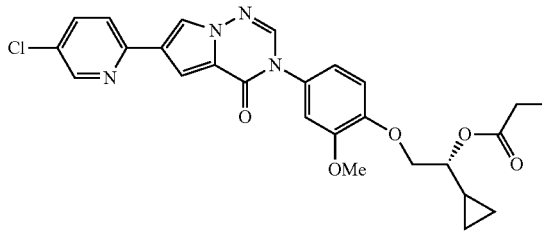

Example 49 was prepared using a procedure analogous to Example 41 above. LC-MS, [M+H]$^+$=510.0. $^1$H NMR (CD$_3$OD, 400 MHz): δ 0.35-0.62 (m, 4H), 1.10-1.20 (m, 1H), 3.71 (d, J=18.8 Hz, 1H), 3.83 (s, 3H), 3.79 (d, J=18.8 Hz, 1H), 4.20-4.29 (m, 2H), 4.61-4.68 (m, 1H), 6.90 (dd, J=8.8, 2.2 Hz, 1H), 7.02-7.05 (m, 2H), 7.46 (d, J=1.8 Hz, 1H), 7.71 (d, J=8.2 Hz, 1H), 7.71 (d, J=8.2 Hz, 1H), 7.75 (dd, J=8.2, 2.2 Hz, 1H), 7.85 (s, 1H), 8.03 (d, J=1.8 Hz, 1H).

Example 50

1-((4-(6-(5-Chloropyridin-2-yl)-4-oxopyrrolo[1,2-f][1,2,4]triazin-3(4H)-yl)-2-methoxyphenoxy)methyl)-3,3-difluorocyclobutyl 2-aminoacetate, 2 HCl

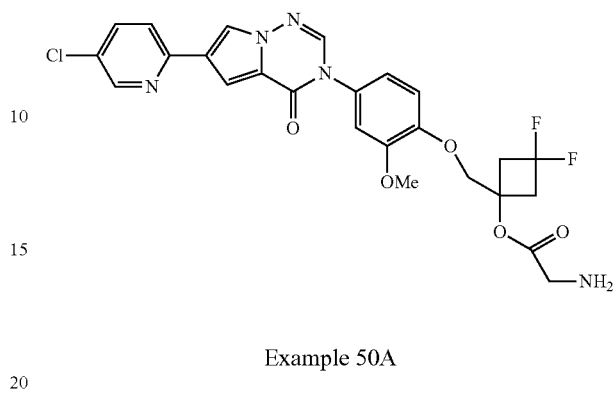

Example 50A 1-((4-(6-(5-Chloropyridin-2-yl)-4-oxopyrrolo[1,2-f][1,2,4]triazin-3(4H)-yl)-2-methoxyphenoxy)methyl)-3,3-difluorocyclobutyl 2-(tert-butoxycarbonylamino)acetate

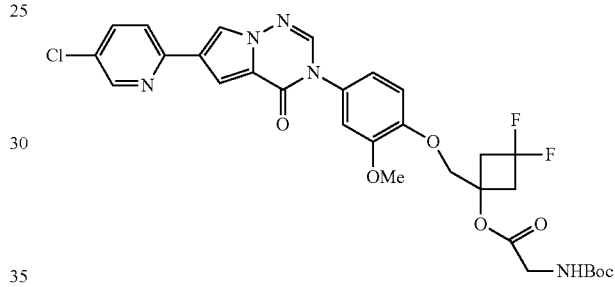

To a solution of Example 46 (0.510 g, 1.043 mmol), 2-(tert-butoxycarbonylamino)acetic acid (1.097 g, 6.26 mmol) and 4-(pyrrolidin-1-yl)pyridine (0.928 g, 6.26 mmol) in DCM (15.6 mL) at RT was added EDC (1.200 g, 6.26 mmol). The reaction mixture was heated to reflux for 15 min. Solvent was evaporated. The crude residue was diluted with EtOAc (200 mL) and washed with 0.5 N HCl (16 mL) and H$_2$O (16 mL). The organic layer was separated, dried over MgSO$_4$ and concentrated to give the crude product which was further purified by ISCO automated chromatography (120 g, Hexane/EtOAc, 100:0 to 50:50 gradient) to give Example 50A (0.620 g, 92%) as a white solid.

Example 50

1-((4-(6-(5-Chloropyridin-2-yl)-4-oxopyrrolo[1,2-f][1,2,4]triazin-3(4H)-yl)-2-methoxyphenoxy)methyl)-3,3-difluorocyclobutyl 2-aminoacetate, 2 HCl

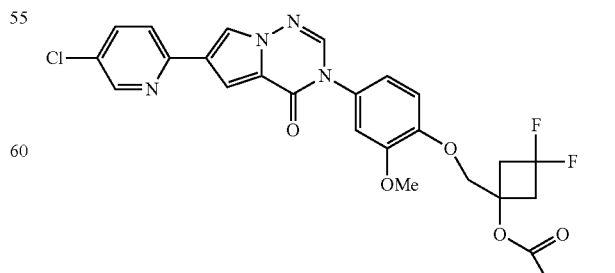

Example 50 was prepared from Example 50A using a procedure analogous to Example 41 above. LC-MS, [M+H]⁺=546.0. ¹H NMR (CD₃OD, 400 MHz): δ 3.02-3.25 (m, 4H), 3.80 (s, 2H), 3.87 (s, 3H), 4.49 (s, 2H), 7.02 (dd, J=8.8, 2.2 Hz, 1H), 7.13-7.18 (m, 2H), 7.69 (d, J=2.2 Hz, 1H), 8.04 (s, 1H), 8.20 (d, J=8.2 Hz, 1H), 8.32 (dd, J=8.2, 2.2 Hz, 1H), 8.36 (d, J=2.2 Hz, 1H), 8.76 (d, J=2.2 Hz, 1H).

Example 51

3-(4-(6-(4-Chlorophenyl)-4-oxopyrrolo[1,2-f][1,2,4]triazin-3(4H)-yl)-2-methoxyphenoxy)-2-methylpropane-1,2-diylbis(2-aminoacetate), 2 HCl

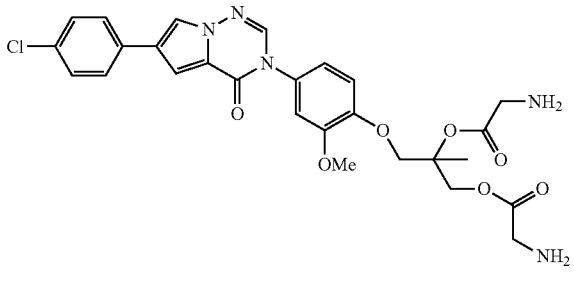 [SMILES: COc1cc(-n2cnn3cc(-c4ccc(Cl)cc4)cc3c2=O)ccc1OCC(C)(COC(=O)CN)OC(=O)CN]

Example 51A 3-(4-(6-(4-Chlorophenyl)-4-oxopyrrolo[1,2-f][1,2,4]triazin-3(4H)-yl)-2-methoxyphenoxy)-2-methylpropane-1,2-diyl bis(2-(tert-butoxycarbonylamino)acetate)

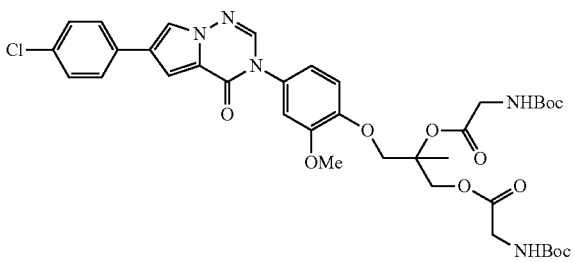 [SMILES: COc1cc(-n2cnn3cc(-c4ccc(Cl)cc4)cc3c2=O)ccc1OCC(C)(COC(=O)CNC(=O)OC(C)(C)C)OC(=O)CNC(=O)OC(C)(C)C]

Example 51A was prepared from Example 47 in a manner similar to Example 22A. LC-MS, [M+H]⁺=770.4.

Example 51

3-(4-(6-(4-Chlorophenyl)-4-oxopyrrolo[1,2-f][1,2,4]triazin-3(4H)-yl)-2-methoxyphenoxy)-2-methylpropane-1,2-diylbis(2-aminoacetate), 2 HCl

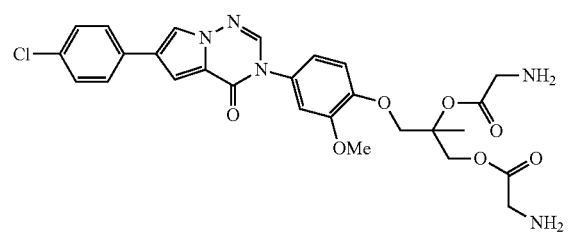 [SMILES: COc1cc(-n2cnn3cc(-c4ccc(Cl)cc4)cc3c2=O)ccc1OCC(C)(COC(=O)CN)OC(=O)CN]

Example 51 was prepared from Example 51A using a procedure analogous to Example 41 above. LC-MS, [M+H]⁺=570.3. ¹H NMR (DMSO-d₆, 400 MHz): δ 1.63 (s, 3H), 3.33 (s, 4H), 3.79 (s, 3H), 4.31 (d, J=10.4 Hz, 1H), 4.40 (d, J=10.4 Hz, 1H), 4.55 (d, J=11.6 Hz, 1H), 4.62 (d, J=11.6 Hz, 1H), 7.05 (dd, J=8.8, 2.2 Hz, 1H), 7.13 (d, J=8.8 Hz, 1H), 7.21 (d, J=2.2 Hz, 1H), 7.42-7.48 (m, 3H), 7.82-7.86 (m, 2H), 8.10 (s, 1H), 8.27 (d, J=1.8 Hz, 1H), 8.35 (bs, 2H), 8.45 (bs, 2H).

Example 52

(S)-6-(4-Chlorophenyl)-3-(4-(3-(ethylsulfonyl)-2-hydroxypropoxy)-3-methoxyphenyl)pyrrolo[1,2-f][1,2,4]triazin-4(3H)-one

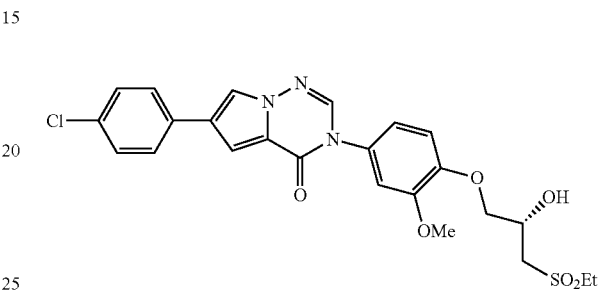

Example 52 was prepared from Example 18A and (S)-1-(4-amino-2-methoxyphenoxy)-3-(ethylsulfonyl)propan-2-ol (Example 60D) using a procedure analogous to Example 18 above. LC-MS, [M+H]⁺=518.3. ¹H NMR (DMSO-d₆, 400 MHz): δ 1.23 (t, J=7.4 Hz, 3H), 3.09-3.26 (m, 3H), 3.34-3.42 (m, 1H), 3.78 (s, 3H), 3.97-4.05 (m, 2H), 4.27-4.35 (m, 1H), 5.75 (d, J=5.7 Hz, 1H), 7.03 (dd, J=8.8, 2.2 Hz, 1H), 7.11 (d, J=8.8 Hz, 1H), 7.19 (d, J=2.2 Hz, 1H), 7.40-7.45 (m, 2H), 7.47 (d, J=2.2 Hz, 1H), 7.80-7.85 (m, 2H), 8.12 (s, 1H), 8.27 (d, J=2.2 Hz, 1H).

Example 53

(S)-1-(4-(6-(4-Chlorophenyl)-4-oxopyrrolo[1,2-f][1,2,4]triazin-3(4H)-yl)-2-methoxyphenoxy)-3-(ethylsulfonyl)propan-2-yl 2-aminoacetate, TFA

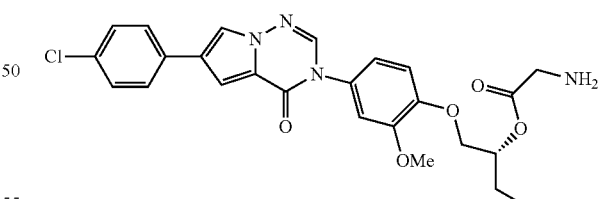

Example 53 was prepared using a procedure analogous to Example 41 above except that N-Boc valine was replaced by N-Boc glycine and the final product amine was purified by Prep HPLC to afford Example 53, TFA salt. LC-MS, [M+H]⁺=575.0. ¹H NMR (CD₃OD, 400 MHz): δ 1.38 (t, J=7.4 Hz, 3H), 3.22 (q, J=7.4 Hz, 2H), 3.71 (d, J=6.1 Hz, 2H), 3.86 (d, J=2.7 Hz, 2H), 3.88 (s, 3H), 4.32-4.40 (m, 2H), 5.84-5.91 (m, 1H), 7.01 (dd, J=8.8, 2.2 Hz, 1H), 7.13-7.16 (m, 2H), 7.37-7.41 (m, 3H), 7.65-7.70 (m, 2H), 7.91 (s, 1H), 7.96 (d, J=1.8 Hz, 1H).

Example 54

3-(4-(6-(4-Chlorophenyl)-4-oxopyrrolo[1,2-f][1,2,4]triazin-3(4H)-yl)-2-methoxyphenoxy)-2-hydroxy-2-methylpropanoic acid

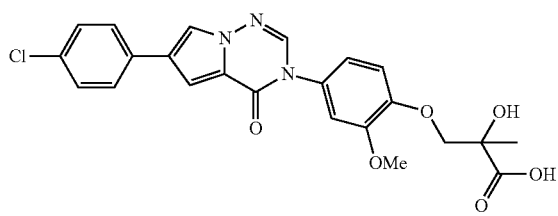 [SMILES: COc1cc(-n2cnn3cc(-c4ccc(Cl)cc4)cc3c2=O)ccc1OCC(C)(O)C(=O)O]

Example 54A

Methyl 2-hydroxy-3-(2-methoxy-4-nitrophenoxy)-2-methylpropanoate

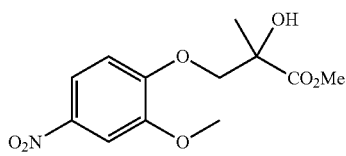 [SMILES: COC(=O)C(C)(O)COc1ccc([N+](=O)[O-])cc1OC]

A mixture of potassium 2-methoxy-4-nitrophenolate (200 mg, 0.965 mmol), sodium dihydrogen phosphate (116 mg, 0.965 mmol) and methyl 2-methyloxirane-2-carboxylate (200 mL, 1.890 mmol) in acetonitrile (0.85 mL) and H$_2$O (150 mL) was heated at 150° C. in a sealed tube for 2 h. After cooling to room temperature, the reaction mixture was diluted with H$_2$O (2 mL). The resulting mixture was extracted with CH$_2$Cl$_2$ (3×8 mL). The organic layer was separated, dried over MgSO$_4$ and concentrated to give the crude product which was further purified by ISCO automated chromatography (12 g silica, 0% to 60% EtOAc-Hexanes) to yield Example 54A (204 mg, 74% yield) as a beige solid. LC-MS, [M+H]$^+$=286.4.

Example 54B

2-Hydroxy-3-(2-methoxy-4-nitrophenoxy)-2-methylpropanoic acid

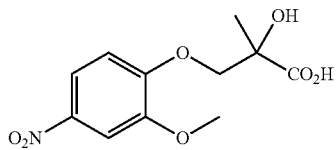 [SMILES: COc1cc([N+](=O)[O-])ccc1OCC(C)(O)C(=O)O]

A mixture of methyl 2-hydroxy-3-(2-methoxy-4-nitrophenoxy)-2-methylpropanoate (308 mg, 1.080 mmol) and sodium hydroxide (145 mg, 3.63 mmol) in H$_2$O (7.3 mL) and MeOH (4.35 ml) was heated at 75° C. for 2 h. Volatiles were evaporated and the pH of the residual mixture was brought to 2 by adding aq 1N HCl. The mixture was subjected to filtration and the solid was dried under vacuum to yield Example 54B as a pale yellow solid. (250 mg, 85%).

Example 54C

Allyl 2-hydroxy-3-(2-methoxy-4-nitrophenoxy)-2-methylpropanoate

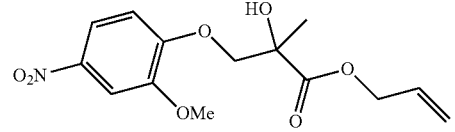

A mixture of Example 54B (207 mg, 0.763 mmol), 3-bromoprop-1-ene (138 mg, 1.14 mmol) and cesium carbonate (249 mg, 0.763 mmol) in acetonitrile (8 mL) was allowed to stirred at RT over the weekend. Solid was filtered out. The filtrate was concentrated to give a crude product which was further purified by flash chromatography (12 g silica, 0% to 70% EtOAc-Hexanes) yielding Example 54C (55.8 mg, 24%) as a yellow oil.

Example 54D

Allyl 3-(4-amino-2-methoxyphenoxy)-2-hydroxy-2-methylpropanoate

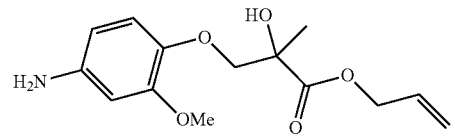 [SMILES: C=CCOC(=O)C(C)(O)COc1ccc([N+](=O)[O-])cc1OC]

A mixture of Example 54C (55.8 mg, 0.179 mmol), tin(II) chloride dihydrate (202 mg, 0.896 mmol) in ethyl acetate (3 ml) was heated at reflux for 4 h. 5 drops of EtOH were added. The resulting mixture was heated at reflux overnight. The mixture was diluted with EtOAc (15 mL) and satu. aq. NaHCO$_3$ solution (3 mL) was added. The mixture was shaken for 2 min and filtered through a CELITE® pad. The filtrate was evaporated to give the crude product which was further purified by flash chromatography (12 g silica, 0% to 50% EtOAc-Hexanes) to yield Example 54D (27 mg, 54%) as a light brown oil. LC-MS, [M+H]$^+$=282.5.

Example 54E

Allyl 3-(4-(6-(4-chlorophenyl)-4-oxopyrrolo[1,2-f][1,2,4]triazin-3(4H)-yl)-2-methoxyphenoxy)-2-hydroxy-2-methylpropanoate

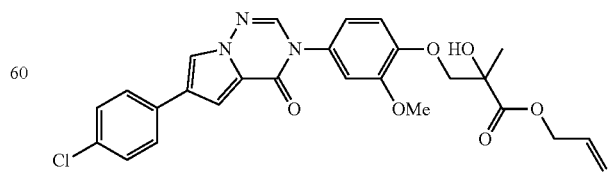

Example 54E was prepared from Example 18A and Example 54D using a procedure analogous to Example 18 above. LC-MS, [M+H]$^+$=510.5.

Example 54

3-(4-(6-(4-Chlorophenyl)-4-oxopyrrolo[1,2-f][1,2,4]triazin-3(4H)-yl)-2-methoxyphenoxy)-2-hydroxy-2-methylpropanoic acid

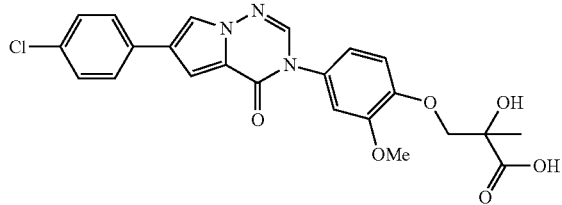 [SMILES: COc1cc(-n2cnn3cc(-c4ccc(Cl)cc4)cc3c2=O)ccc1OCC(C)(O)C(=O)O]

To a solution of Example 54E (7 mg, 0.014 mmol) in THF (0.5 mL) at RT under Argon was added Pd(Ph$_3$P)$_4$ (11 mg, 9.52 µmol) and morpholine (0.012 mL, 0.14 mmol). The resulting mixture was stirred at RT for 2 h. Solvent was evaporated. The crude was dissolved in ACN (2 mL) and purification by Preparative HPLC (PHENOMENEX® Luna Axia 5µ C18 30×100 mm; 10 min gradient from 65% A: 35% B to 0% A:100% B (A=90% H$_2$O/10% ACN+0.1% TFA); (B=90% ACN/10% H$_2$O+0.1% TFA); detection at 220 nm) yielded Example 54 (3.2 mg, 47% yield) as a white solid. LC-MS, [M+H]$^+$=470.3. $^1$H NMR (CD$_3$OD, 400 MHz): δ 1.47 (s, 3H), 3.86 (s, 3H), 4.06 (d, J=9.7 Hz, 1H), 4.29 (d, J=9.7 Hz, 1H), 6.98 (dd, J=8.8, 2.2 Hz, 1H), 7.10-7.13 (m, 2H), 7.37-7.40 (m, 3H), 7.65-7.70 (m, 2H), 7.91 (s, 1H), 7.96 (d, J=1.8 Hz, 1H).

Example 55

(S)-1-(4-(6-(4-Chlorophenyl)-4-oxopyrrolo[1,2-f][1,2,4]triazin-3(4H)-yl)-2-methoxyphenoxy)propan-2-yl 2-amino-3-methylbutanoate, TFA

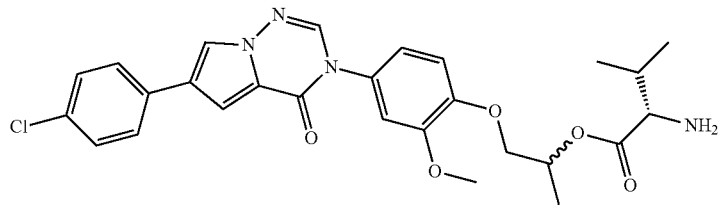 [SMILES: COc1cc(-n2cnn3cc(-c4ccc(Cl)cc4)cc3c2=O)ccc1OCC(C)OC(=O)[C@@H](N)C(C)C]

Example 55 was prepared from Example 25 following a procedure analogous to the one shown for Example 40. Purification by Preparative HPLC (PHENOMENEX® Luna Axia 5µ C18 30×100 mm; 10 min gradient from 75% A: 25% B to 0% A:100% B (A=90% H$_2$O/10% MeOH+0.1% TFA); (B=90% MeOH/10% H$_2$O+0.1% TFA); detection at 220 nm) yielded Example 55 (26.8 mg, 0.047 mmol, 98% yield) as a white solid. LC-MS, [M+H]$^+$=525.0. $^1$H NMR (CD$_3$OD, 400 MHz): δ 8.0 (t, J=1.5 Hz, 1H), 7.9 (d, J=1.3 Hz, 1H), 7.65-7.70 (br d, J=8.8 Hz, 2H), 7.36-7.42 (m, 3H), 7.0 (ddd, J=8.6, 2.6, 2.4 Hz, 1H), 5.38-5.5 (m, 1H), 4.12-4.24 (m, 2H), 3.9 (dd, J=18.9, 4.4 Hz, 1H), 3.8 and 3.9 (two singlets, total 3H), 2.23-2.38 (m, 1H), 1.41-1.47 (2 doublets, J~6 Hz)+1.1 (br d, J=7.0 Hz), total 9H.

Example 56

(2S,2'S)-((3S,4R)-1-(4-(6-(4-Chlorophenyl)-4-oxopyrrolo[1,2-f][1,2,4]triazin-3(4H)-yl)-2-methoxyphenyl)pyrrolidine-3,4-diyl)bis(2-amino-3-methylbutanoate), 2TFA

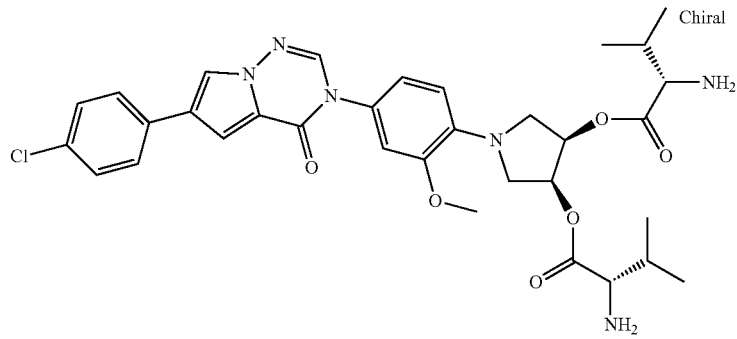

Example 56A (2S,2'S)-((3S,4R)-1-(4-(6-(4-Chlorophenyl)-4-oxopyrrolo[1,2-f][1,2,4]triazin-3(4H)-yl)-2-methoxyphenyl)pyrrolidine-3,4-diyl)bis(2-(tert-butoxycarbonylamino)-3-methylbutanoate)

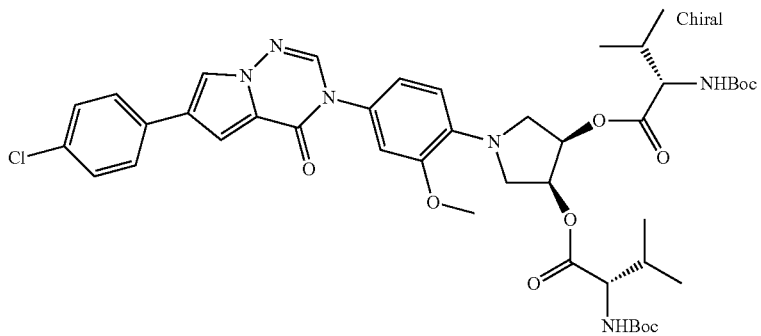 [SMILES: COc1cc(-n2cnn3cc(-c4ccc(Cl)cc4)cc3c2=O)ccc1N1C[C@H](OC(=O)[C@@H](NC(=O)OC(C)(C)C)C(C)C)[C@H](OC(=O)[C@@H](NC(=O)OC(C)(C)C)C(C)C)C1]

To Example 26 (10 mg, 0.022 mmol), (S)-2-(tert-butoxycarbonylamino)-3-methylbutanoic acid (19 mg, 0.087 mmol), and DMAP (5 mg, 0.041 mmol) in DCM (5 mL) and acetonitrile (2 mL) was added DIC (20 μL, 0.128 mmol) and the mixture stirred at RT for 3 h. Additional 10 mg Boc-Val and 20 μL DIC were added and the mixture stirred at RT for an additional 2 h, evaporated, and purified by flash chromatography (12 g, 0% to 100% EtOAc-Hexanes) to yield Example 56A as a colorless residue, which was used as such for deprotection. LC-MS, [M+H]⁺=851.0.

Example 56

(2S,2'S)-((3S,4R)-1-(4-(6-(4-Chlorophenyl)-4-oxopyrrolo[1,2-f][1,2,4]triazin-3(4H)-yl)-2-methoxyphenyl)pyrrolidine-3,4-diyl)bis(2-amino-3-methylbutanoate), 2TFA

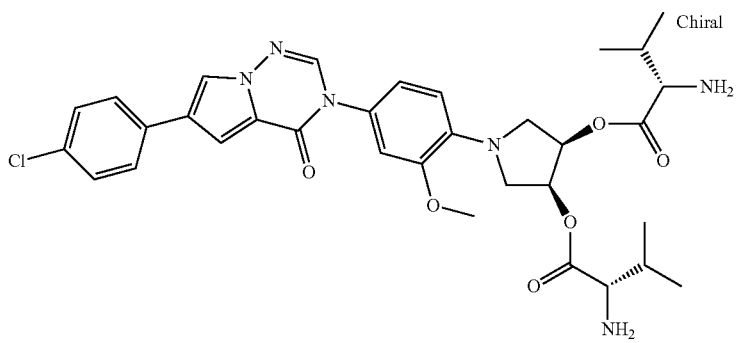 [SMILES: COc1cc(-n2cnn3cc(-c4ccc(Cl)cc4)cc3c2=O)ccc1N1C[C@H](OC(=O)[C@@H](N)C(C)C)[C@H](OC(=O)[C@@H](N)C(C)C)C1]

To Example 56A (18.73 mg, 0.022 mmol) was added 4N HCl/Dioxane (0.668 μL, 0.022 mmol) and the mixture stirred for 2 h at RT. Evaporation followed by purification by Preparative HPLC (PHENOMENEX® Luna Axia 5μ C18 30×100 mm; 10 min gradient from 100% A: 0% B to 0% A:100% B (A=90% H₂O/10% MeOH+0.1% TFA); (B=90% MeOH/10% H₂O+0.1% TFA); detection at 220 nm) yielded Example 56 (9.3 mg, 9.63 μmol, 43.8% yield) as a light pink residue. LC-MS, [M+H]⁺=651.1. ¹H NMR (CD₃OD, 400 MHz): δ 8.0, 1H), 7.7 (d, J=8.8 Hz, 2H), 7.35-7.42 (m, 3H), 7.1 (d, J=2.2 Hz, 1H), 7.0 (dd, J=8.4, 2.2 Hz, 1H), 6.8 (d, J=88.8 Hz, 1H), 4.03 (m, 2H), 4.0 (s, 2H), 3.82-3.95 (m, 2H), 3.84 (s, 3H), 3.63-3.70 (m, 2H), 2.27-2.40 (m, 2H), 1.14, 1.13 & 1.08 (three doublets, J~7 Hz each, total 12H).

HPLC-1: Rt=6.73 min, purity=91%
HPLC-2: Rt=5.70 min, purity=91%.

Example 57

6-(5-Chloropyrimidin-2-yl)-3-(4-((3,3-difluoro-1-hydroxycyclobutyl)methoxy)-3-methoxyphenyl)pyrrolo[1,2-f][1,2,4]triazin-4(3H)-one

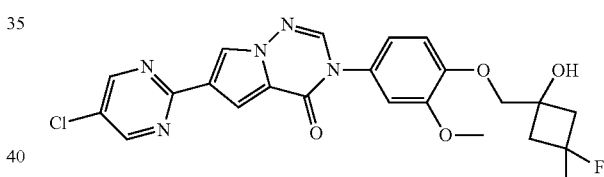

Example 57 was prepared from Example 44F and 1-((4-amino-2-methoxyphenoxy)methyl)-3,3-difluorocyclobutanol (Example 45G) in a manner analogous to Example 18. LC-MS, [M+H]⁺=489.9. ¹H NMR (DMSO-d₆, 400 MHz): δ 8.94 (s, 2H), 8.28 (d, J=1.8 Hz, 1H), 8.21 (s, 1H), 7.50 (d, J=1.8 Hz, 1H), 7.23 (d, J=2.6 Hz, 1H), 7.16 (d, J=8.8 Hz, 1H), 7.05 (dd, J=8.8, 2.6 Hz, 1H), 5.86 (s, 1H), 4.0 (s, 2H), 3.79 (s, 3H), 2.82-2.94 (m, 2H), 2.58-2.70 (m, 2H).

Example 58

1-((4-(6-(5-Chloropyrimidin-2-yl)-4-oxopyrrolo[1,2-f][1,2,4]triazin-3(4H)-yl)-2-methoxyphenoxy)methyl)-3,3-difluorocyclobutyl 2-aminoacetate, HCl salt

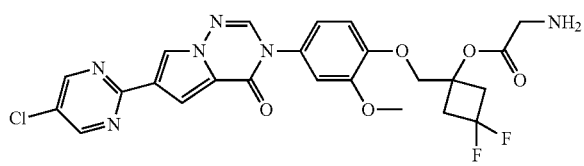 [SMILES: COc1cc(-n2cnn3cc(-c4ncc(Cl)cn4)cc3c2=O)ccc1OCC1(OC(=O)CN)CC(F)(F)C1]

Example 58A 1-((4-(6-(5-Chloropyrimidin-2-yl)-4-oxopyrrolo[1,2-f][1,2,4]triazin-3 (4H)-yl)-2-methoxyphenoxy)methyl)-3,3-difluorocyclobutyl 2-(tert-butoxycarbonylamino)acetate

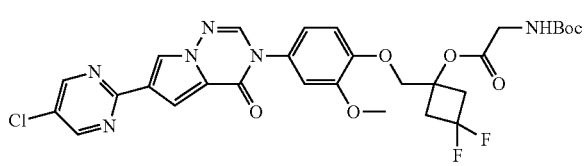 [SMILES: COc1cc(-n2cnn3cc(-c4ncc(Cl)cn4)cc3c2=O)ccc1OCC1(OC(=O)CNC(=O)OC(C)(C)C)CC(F)(F)C1]

To a mixture of Example 57 (24 mg, 0.049 mmol), 2-(tert-butoxycarbonylamino)acetic acid (49 mg, 0.280 mmol), and 4-(pyrrolidin-1-yl)pyridine (41 mg, 0.277 mmol) in DCM (10 mL) was added EDC (47 mg, 0.245 mmol) and the mixture was refluxed for 2 h. The mixture was diluted with DCM (25 mL) and washed with 1N HCl, brine, dried (Na$_2$SO$_4$), and evaporated under reduced pressure to obtain a residue which was purified by flash chromatography (12 g, 0% to 100% EtOAc-Hexanes) to yield Example 58A (30 mg, 0.046 mmol, 95% yield) as a white solid. LC-MS, [M+H]$^+$=546.9 (M-Boc).

Example 58

1-((4-(6-(5-Chloropyrimidin-2-yl)-4-oxopyrrolo[1,2-f][1,2,4]triazin-3(4H)-yl)-2-methoxyphenoxy)methyl)-3,3-difluorocyclobutyl 2-aminoacetate, HCl salt

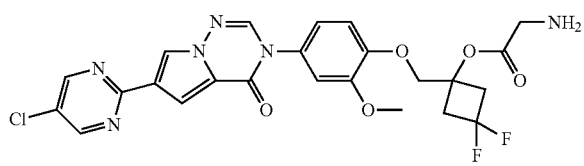 [SMILES: COc1cc(-n2cnn3cc(-c4ncc(Cl)cn4)cc3c2=O)ccc1OCC1(OC(=O)CN)CC(F)(F)C1]

To Example 58A (30 mg, 0.046 mmol) was added 4N HCl/dioxane (3 mL, 99 mmol) at RT and the mixture stirred for 3 h. The mixture was diluted with ether, filtered, washed with ether, and dried to yield Example 58 (22 mg, 80%) as a white solid. LC-MS, [M+H]$^+$=547.0. $^1$H NMR (DMSO-d$_6$, 500 MHz): δ 8.94 (s, 2H), 8.28 (d, J=1.7 Hz, 1H), 8.20 (s, 1H), 7.50 (d, J=1.7 Hz, 1H), 7.26 (d, J=2.2 Hz, 1H), 7.16 (d, J=8.3 Hz, 1H), 7.07 (d, J=8.3, 2.2 Hz, 1H), 4.41 (s, 2H), 3.83 (s, 2H), 3.80 (s, 3H), 3.16-3.25 (m, 2H), 3.05-3.15 (m, 2H). HPLC-1: Rt=6.37 min, purity=98%; HPLC-2: Rt=7.24 min, purity=98%.

Example 59

1-((4-(6-(4-Chlorophenyl)-4-oxopyrrolo[1,2-f][1,2,4]triazin-3(4H)-yl)-2-methoxyphenoxy)methyl)-3,3-difluorocyclobutyl 2-aminoacetate, HCl salt

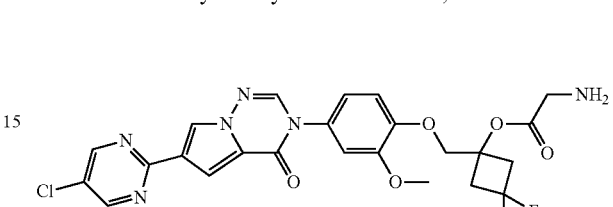

Example 59 was prepared in a manner analogous to Example 58. LC-MS, [M+H]$^+$=545.0. $^1$H NMR (DMSO-d$_6$, 400 MHz): δ 8.28 (d, J=1.8 Hz, 1H), 8.12 (s, 1H), 7.83 (d, J=8.8 Hz, 2H), 7.46 (d, J=1.8 Hz, 1H), 7.44 (d, J=8.4 Hz, 2H), 7.23 (d, J=1.8 Hz, 1H), 7.13 (d, J=8.4 Hz, 1H), 7.04 (dd, J=8.6, 2.0 Hz, 1H), 4.40 (s, 2H), 3.82 (s, 2H), 3.79 (s, 3H), 3.05-3.25 (m, 4H). HPLC-1: Rt=7.69 min, purity=93%; HPLC-2: Rt=8.60 min, purity=93%.

Example 60

(S)-6-(5-Chloropyrimidin-2-yl)-3-(4-(3-(ethylsulfonyl)-2-hydroxypropoxy)-3-methoxyphenyl)pyrrolo[1,2-f][1,2,4]triazin-4(3H)-one

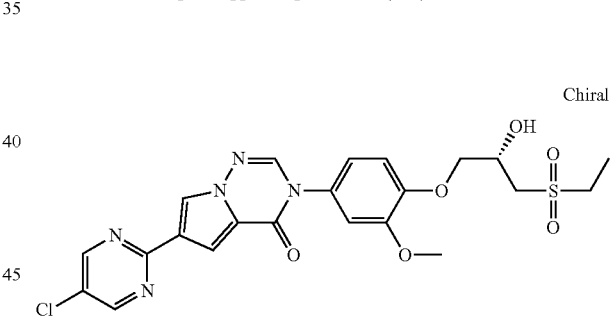

Example 60A (R)-2-((2-Methoxy-4-nitrophenoxy)methyl)oxirane

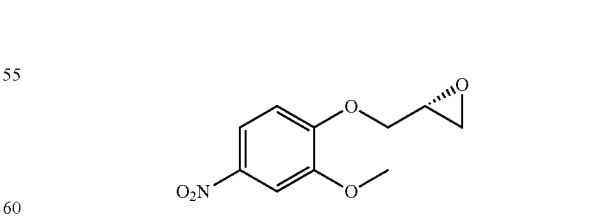

To a solution of potassium 2-methoxy-4-nitrophenolate (6.0 g, 29.0 mmol) in DMF (30 mL) was added cesium fluoride (13.19 g, 87 mmol). After stirring 1 h, (R)-oxiran-2-ylmethyl 3-nitrobenzenesulfonate (8.26 g, 31.8 mmol) was added and the mixture was stirred for 2 days. The mixture was partially concentrated under reduced pressure, diluted with water and extracted with EtOAc. The combined organic extracts were washed with water, brine, dried (MgSO₄), and concentrated. The residue was purified by chromatography (SiO₂ solvent gradient 33-60% EtOAc/Hexanes) to give the Example 60A (6.41 g, 98% yield) as a white solid. LC-MS, [M+H]⁺=226. ¹H NMR (CDCl₃, 400 MHz) δ 7.89 (dd, J=8.8 and 2.6 Hz, 1H), 7.76 (d, J=2.6 Hz, 1H), 6.98 (d, J=8.8 Hz, 1H), 4.43 (dd, J=11.4 and 2.6 Hz, 1H), 4.08 (dd, J=11.4 and 6.2 Hz, 1H), 3.96 (s, 3H), 3.43 (m, 1H), 2.95 (m, 1H), 2.81 (m, 1H).

Example 60B (S)-1-(Ethylthio)-3-(2-methoxy-4-nitrophenoxy)propan-2-ol

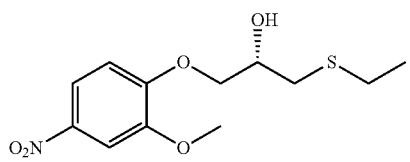 [SMILES: CCSC[C@@H](O)COc1ccc([N+](=O)[O-])cc1OC]

To a solution of ethanethiol (0.98 mL, 13.32 mmol) in 25% KOH (29.9 g, 133 mmol) was added Example 60A (3.0 g, 13.3 mmol) in THF (20 mL) and tetrabutylammonium bromide (0.429 g, 1.33 mmol). After stirring 2 h, the mixture was diluted with water and extracted with EtOAc. The combined organic extracts were washed with water, dried (MgSO₄), and concentrated. The residue was purified by chromatography (SiO₂ solvent gradient 25-50% EtOAc/Hexanes) to give Example 60B (2.92 g, 76% yield) as a white solid. LC-MS, [M+Na]⁺=310. ¹H NMR (CDCl₃, 400 MHz) δ 7.89 (dd, J=8.8 and 2.6 Hz, 1H), 7.75 (d, J=2.6 Hz, 1H), 6.95 (d, J=8.8 Hz, 1H), 4.19 (m, 3H), 3.94 (s, 3H), 2.89 (m, 2H), 2.61 (q, J=7.5 Hz, 2H), 1.28 (t, J=7.5 Hz, 3H).

Example 60C (S)-1-(Ethylsulfonyl)-3-(2-methoxy-4-nitrophenoxy)propan-2-ol

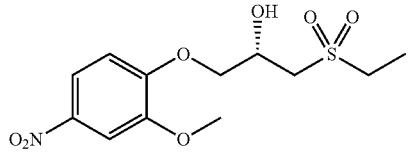 [SMILES: CCS(=O)(=O)C[C@@H](O)COc1ccc([N+](=O)[O-])cc1OC]

To a solution of Example 60B (2.92 g, 10.16 mmol) in methylene chloride (100 mL) at 0° C. was added m-CPBA (5.69 g, 25.4 mmol) in portions. The mixture was warmed to rt. and was stirred 3 h. The resulting solid was filtered and the filtrate was diluted with methylene chloride, washed sat. NaHCO₃, dried MgSO₄ and concentrated. The residue was purified by chromatography (SiO₂ solvent gradient 40-100% EtOAc/Hexanes) to give the Example 60C (3.21 g, 99% yield) as a white solid. LC-MS, [M+H]⁺=320. ¹H NMR (CDCl₃, 400 MHz) δ 7.89 (dd, J=8.8 and 2.6 Hz, 1H), 7.76 (d, J=2.6 Hz, 1H), 6.95 (d, J=8.8 Hz, 1H), 4.71 (m, 1H), 4.18 (d, J=5.3 Hz, 2H), 3.94 (s, 3H), 3.32 (m, 5H), 1.45 (t, J=7.5 Hz, 3H).

Example 60D (S)-1-(4-Amino-2-methoxyphenoxy)-3-(ethylsulfonyl)propan-2-ol

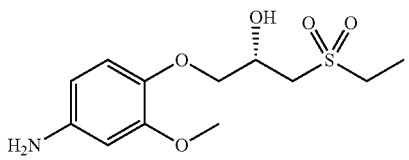

To a solution of Example 60C (2.0 g, 6.26 mmol) in ethanol (200 mL) was added Pd/C (0.333 g, 0.313 mmol, 10%). The mixture was purged with hydrogen (50 PSI) and was stirred 3 h. The mixture was filtered through CELITE® and the filtrate was concentrated. The residue was purified by chromatography (SiO₂ solvent gradient 3-10% MeOH/CH₂Cl₂) to give the Example 60D (1.6 g, 88% yield) as a white solid. LC-MS, [M+H]⁺=290. ¹H NMR (CDCl₃, 400 MHz) δ 6.80 (d, J=8.8 Hz, 1H), 6.28 (d, J=2.6 Hz, 1H), 6.21 (dd, J=8.8 and 2.6 Hz, 1H), 4.46 (m, 1H), 3.97 (m, 2H), 3.81 (s, 3H), 3.25 (m, 4H), 1.42 (t, J=7.5 Hz, 3H).

Example 60

(S)-6-(5-Chloropyrimidin-2-yl)-3-(4-(3-(ethylsulfonyl)-2-hydroxypropoxy)-3-methoxyphenyl)pyrrolo[1,2-f][1,2,4]triazin-4(3H)-one

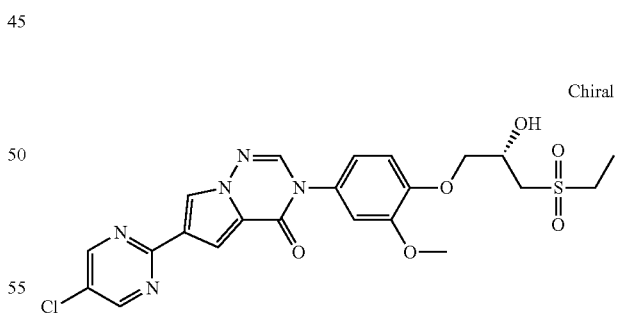

Example 60 was prepared from Example 60D and Example 44F in a manner analogous to Example 18. LC-MS, [M+H]⁺=520.0. ¹H NMR (DMSO-d₆, 400 MHz): δ 8.94 (s, 2H), 8.28 (d, J=1.8 Hz, 1H), 8.22 (s, 1H), 7.50 (d, J=1.8 Hz, 1H), 7.23 (d, J=2.2 Hz, 1H), 7.13 (d, J=8.4 Hz, 1H), 7.06 (dd, J=8.4, 2.2 Hz, 1H), 5.77 (d, J=5.7 Hz, 1H), 4.26-4.38 (m, 1H), 3.96-4.10 (m, 2H), 3.79 (s, 3H), 3.10-3.28 (m, 4H), 1.25 (t, J=7.5 Hz, 3H).

Example 61

(S)-1-(4-(6-(5-Chloropyrimidin-2-yl)-4-oxopyrrolo[1,2-f][1,2,4]triazin-3(4H)-yl)-2-methoxyphenoxy)-3-(ethylsulfonyl)propan-2-yl 2-aminoacetate, TFA

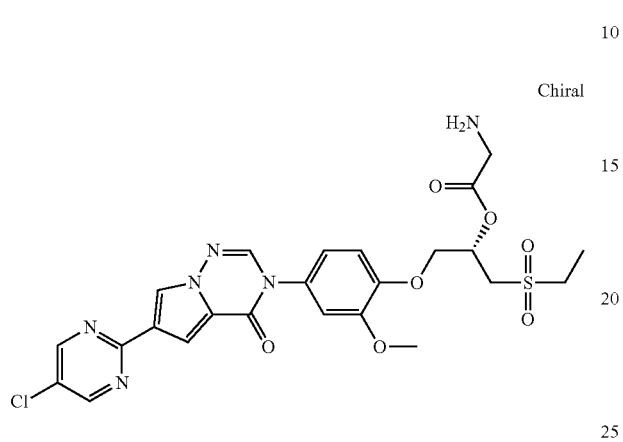

Example 61 was prepared from Example 60 in a manner analogous to Example 58. LC-MS, [M+H]⁺=577.0. ¹H NMR (DMSO-d₆, 400 MHz): δ 8.79 (s, 2H), 8.23 (br s, 1H), 7.98 (br s, 1H), 7.70 (br s, 1H), 7.13-7.19 (m, 2H), 7.0-7.05 (m, 1H), 5.84-5.95 (m, 1H), 4.32-4.45 (m, 2H), 3.89 (s, 3H), 3.86 (d, J=4.8 Hz, 2H), 3.70-3.74 (m, 2H), 3.21 (br q, J=7.5 Hz, 2H), 1.39 (br t, J=7.5 Hz, 3H).

Example 62

(S)-6-(5-Chloropyridin-2-yl)-3-(4-(3-(ethylsulfonyl)-2-hydroxypropoxy)-3-methoxyphenyl)pyrrolo[1,2-f][1,2,4]triazin-4(3H)-one

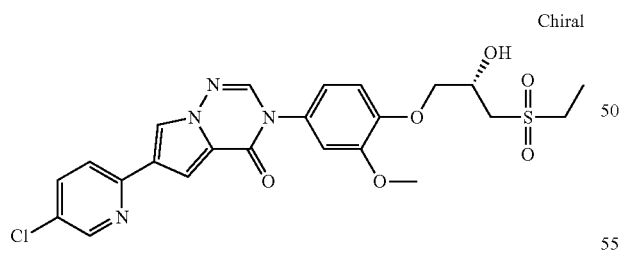

Example 62 was prepared from Example 60D and Example 46A in a manner analogous to Example 18. LC-MS, [M+H]⁺=519.0. ¹H NMR (DMSO-d₆, 400 MHz): δ 8.60 (d, J=2.6 Hz, 1H), 8.29 (d, J=1.8 Hz, 1H), 8.16 (s, 1H), 7.92-8.0 (m, 2H), 7.57 (d, J=2.2 Hz, 1H), 7.21 (d, J=2.2 Hz, 1H), 7.11 (d, J=8.8 Hz, 1H), 7.04 (dd, J=8.4, 2.2 Hz, 1H), 5.76 (d, J=5.7 Hz, 1H), 4.25-4.35 (m, 1H), 3.95-4.04 (m, 2H), 3.78 (s, 3H), 3.10-3.42 (m, 4H), 1.24 (t, J=7.5 Hz, 3H).

Example 63

1-(4-(6-(5-Chloropyridin-2-yl)-4-oxopyrrolo[1,2-f][1,2,4]triazin-3(4H)-yl)-2-methoxyphenoxy)-2-methylpropan-2-yl 2-aminoacetate, 2TFA

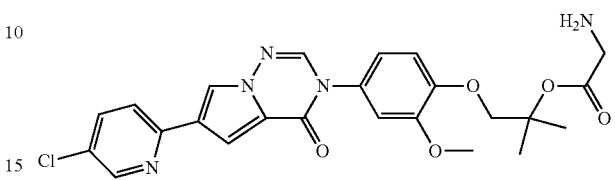

Example 63A 1-(4-(6-(5-Chloropyridin-2-yl)-4-oxopyrrolo[1,2-f][1,2,4]triazin-3(4H)-yl)-2-methoxyphenoxy)-2-methylpropan-2-yl 2-(tert-butoxycarbonylamino)acetate

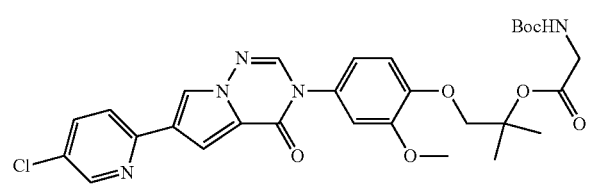 [SMILES: COc1cc(-n2cnn3cc(-c4ccc(Cl)cn4)cc3c2=O)ccc1OCC(C)(C)OC(=O)CNC(=O)OC(C)(C)C]

Example 63A was prepared from Example 46A and Example 22B in a manner analogous to Example 22. LC-MS, [M-Boc]⁺=498.0.

Example 63

1-(4-(6-(5-Chloropyridin-2-yl)-4-oxopyrrolo[1,2-f][1,2,4]triazin-3(4H)-yl)-2-methoxyphenoxy)-2-methylpropan-2-yl 2-aminoacetate, 2TFA

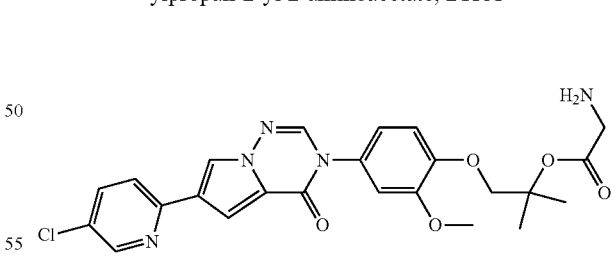

To Example 63A (78 mg, 0.131 mmol) was added 4N HCl/dioxane (4 mL, 16.00 mmol) and the mixture was allowed to stir for 2 h at RT. Evaporation followed by purification by Preparative HPLC (PHENOMENEX® Luna Axia 5μ C18 30×100 mm; 10 min gradient from 80% A: 20% B to 0% A:100% B (A=90% H₂O/10% MeOH+0.1% TFA); (B=90% MeOH/10% H₂O+0.1% TFA); detection at 220 nm) yielded Example 63 (45 mg, 0.062 mmol, 47.3% yield) as an off-white solid. LC-MS, [M+H]⁺=498.0. ¹H NMR (CD₃OD, 400 MHz): δ 8.55 (br s, 1H), 8.15-8.18 (m, 1H), 7.96-8.00 (m, 1H), 7.82-7.88 (m, 2H), 7.56-7.62 (m, 1H), 7.12-7.18 (m, 2H), 7.00-7.05 (m, 1H), 4.31 (br s, 2H), 3.89 (s, 3H), 3.75 (br s, 2H), 1.66 (s, 6H).

Example 64

(S)-1-(4-(6-(5-Chloropyridin-2-yl)-4-oxopyrrolo[1,2-f][1,2,4]triazin-3(4H)-yl)-2-methoxyphenoxy)-3-(ethylsulfonyl)propan-2-yl 2-aminoacetate, 2TFA

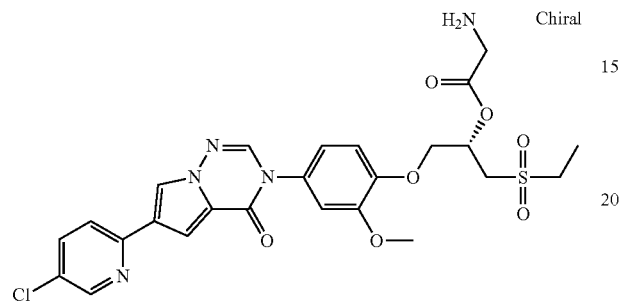

Example 64 was prepared in a manner analogous to Example 58. LC-MS, [M+H]⁺=576.0. ¹H NMR (CD₃OD, 400 MHz): δ 8.52 (d, J=1.8 Hz, 1H), 8.12 (d, J=2.2 Hz, 1H), 7.94 (s, 1H), 7.84 (dd, J=8.4, 2.2 Hz, 1H), 7.79 (d, J=8.8 Hz, 1H), 7.55 (d, J=1.8 Hz, 1H), 7.13-7.18 (m, 2H), 7.00 (dd, J=8.4, 2.6 Hz, 1H), 5.84-5.93 (m, 1H), 4.31-4.42 (m, 2H), 3.88 (s, 3H), 3.87 (s, 2H), 3.68-3.74 (m, 2H), 3.21 (q, J=7.5 Hz, 2H), 1.39 (t, J=7.5 Hz, 3H).

Example 65

6-(4-Chlorophenyl)-3-(4-(6-(2-hydroxypropan-2-yl)-3-azabicyclo[3.1.0]hexan-3-yl)-3-methoxyphenyl)pyrrolo[1,2-f][1,2,4]triazin-4(3H)-one

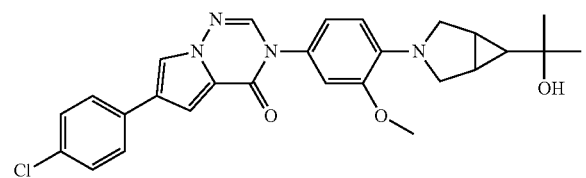 [SMILES: COc1cc(-n2cnn3cc(-c4ccc(Cl)cc4)cc3c2=O)ccc1N1CC2C(C1)C2C(C)(C)O]

Example 65A

Ethyl 3-(2-methoxy-4-nitrophenyl)-3-azabicyclo[3.1.0]hexane-6-carboxylate

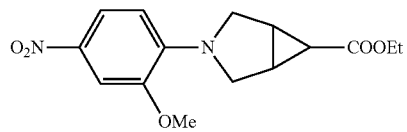 [SMILES: CCOC(=O)C1C2CN(c3ccc([N+](=O)[O-])cc3OC)CC21]

1-Fluoro-2-methoxy-4-nitrobenzene (258 mg, 1.5 mmol) and ethyl 3-azabicyclo[3.1.0]hexane-6-carboxylate (232 mg, 1.5 mmol) were placed in a microwave vial using minimal amount of DCM and heated to 110° C., allowing the DCM to evaporate off. The mixture was allowed to stir at this temperature O.N. Flash chromatography (120 g, 0% to 100% EtOAc-Hexanes) yielded Example 65A (235 mg, 0.767 mmol, 51.3% yield) as a yellow oil which solidified on standing. LC-MS, [M+H]⁺=307.1.

Example 65B

Ethyl 3-(4-amino-2-methoxyphenyl)-3-azabicyclo[3.1.0]hexane-6-carboxylate

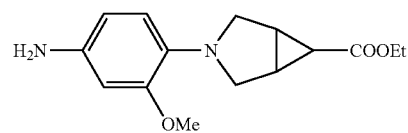

A mixture of Example 65A (235 mg, 0.767 mmol), 10% Pd—C (35 mg, 0.329 mmol) and MeOH-EtOAc (10:2 mL) was hydrogenated at RT, 1 atm, using a H₂ balloon O.N. Filtration and evaporation yielded Example 65B as a dark pink oil (205 mg). LC-MS, [M+H]⁺=277.0. ¹H NMR (CDCl₃, 400 MHz): δ 6.59 (d, J=8.2 Hz, 1H), 6.27 (d, J=2.2 Hz, 1H), 6.23 (dd, J=8.2, 2.2 Hz, 1H), 4.13 (q, J=7.2 Hz, 2H), 3.77 (s, 3H), 3.66 (d, J=9.3 Hz, 2H), 3.03 (d, J=9.3 Hz, 2H), 2.04-2.12 (m, 3H), 1.56 (br s, 2H), 1.27 (t, J=7.2 Hz, 3H).

Example 65C

Ethyl 3-(2-methoxy-4-(tritylamino)phenyl)-3-azabicyclo[3.1.0]hexane-6-carboxylate

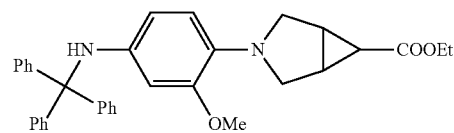

To Example 65B (204 mg, 0.738 mmol) and (chloromethanetriyl)tribenzene (226 mg, 0.812 mmol) in DCM (5 mL) was added triethylamine (0.206 mL, 1.476 mmol) and the mixture allowed to stir for 72 h. Evaporation and purification by flash chromatography (40 g, 0% to 100% EtOAc-Hexanes) yielded Example 65C (320 mg, 0.617 mmol, 84% yield).

Example 65D 2-(3-(4-Amino-2-methoxyphenyl)-3-azabicyclo[3.1.0]hexan-6-yl)propan-2-ol

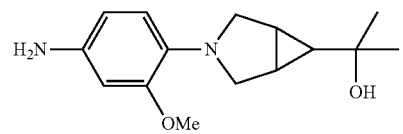 [SMILES: COc1cc(N)ccc1N1CC2C(C1)C2C(C)(C)O]

To a solution of Example 65C (115 mg, 0.222 mmol) in toluene (6 mL) at RT was added MeMgBr, 1.4M in toluene:THF (75:25) (1 mL, 1.400 mmol) and the mixture stirred O.N.

at RT. The reaction mixture was quenched with sat. aq. NH₄Cl, basified with 1N NaOH to pH ~9, and extracted into EtOAc (×2). The organic layer was washed with brine, dried (Na₂SO₄), and evaporated under reduced pressure to obtain a dark brown oil. LC-MS, [M-Tr]⁺=263.1. The residue was dissolved in 1-2 mL MeOH and 3-4 drops of TFA added to obtain a dark pink solution which was filtered and purified by Preparative HPLC (PHENOMENEX® Luna Axia 5μ C18 30×100 mm; 10 min gradient from 75% A: 25% B to 0% A:100% B (A=90% H₂O/10% MeOH+0.1% TFA); (B=90% MeOH/10% H₂O+0.1% TFA); detection at 220 nm) to afford Example 65D (28 mg, 47%).

Example 65E (E)-4-(4-Chlorophenyl)-1-((dimethylamino)methyleneamino)-N-(4-(6-(2-hydroxypropan-2-yl)-3-azabicyclo[3.1.0]hexan-3-yl)-3-methoxyphenyl)-1H-pyrrole-2-carboxamide

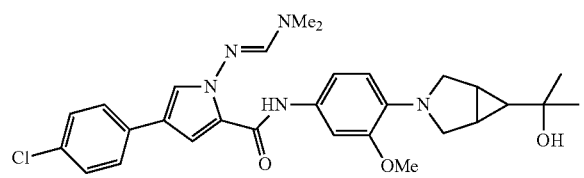 [SMILES: COc1cc(NC(=O)c2cc(-c3ccc(Cl)cc3)cn2/N=C/N(C)C)ccc1N1CC2C(C1)C2C(C)(C)O]

To Example 18A (21.5 mg, 0.074 mmol) in a 25 mL RBF was added 1-(3-dimethylaminopropyl)-3-ethylcarbodiimide hydrochloride (37 mg, 0.193 mmol), HOBt (8 mg, 0.052 mmol), DMF (2.5 mL) and DIPEA (25 μL, 0.143 mmol). The mixture was stirred at RT for 15 min and then a solution of Example 65D (17 mg, 0.065 mmol) in DMF (1 mL) was added over 2 min. The resulting brown solution was allowed to stir at RT O.N. The reaction mixture was taken up in 30 mL DCM, washed with H₂O, 0.3N HCl, brine, dried (Na₂SO₄), filtered, and evaporated to yield a residue which was purified by flash chromatography (12 g, 0% to 100% EtOAc-Hexanes) to yield Example 65E (3.1 mg, 8.9% yield). TLC (7:3 EA-Hex)-R_f 0.16. LC-MS, [M+H]⁺=536.2.

Example 65

6-(4-Chlorophenyl)-3-(4-(6-(2-hydroxypropan-2-yl)-3-azabicyclo[3.1.0]hexan-3-yl)-3-methoxyphenyl)pyrrolo[1,2-f][1,2,4]triazin-4(3H)-one

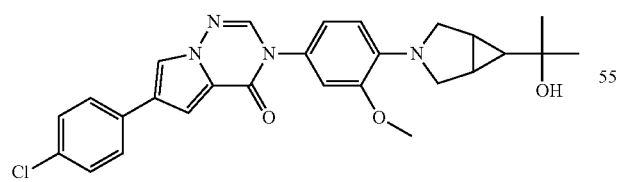

A mixture of Example 65E (3 mg, 5.60 μmol), acetonitrile (0.5 mL), and 1 drop glacial HOAc was heated in a microwave reactor at 160° C. for 30 min. Evaporation followed by purification by flash chromatography (4 g, 0% to 100% EtOAc-Hexanes) yielded Example 65 (1 mg, 1.731 μmol, 30.9% yield) as a white solid. LC-MS, [M+H]⁺=491.2. ¹H NMR (CDCl₃, 400 MHz): δ 7.67 (s, 1H), 7.60 (s, 1H), 6.72 (d, J=8.2 Hz, 2H), 7.38 (s, 1H), 7.35 (d, J=7.7 Hz, 2H), 6.80-6.86 (m, 2H), 6.72 (d, J=8.2 Hz, 1H), 3.81-3.86 (m, 4H), 3.22 (d, J=9.3 Hz, 2H), 1.60-1.65 (m, 2H), 1.27 (s, 6H), 0.80-0.92 (m, 2H).

Example 66

6-(4-Chlorophenyl)-3-(4-(2,3-dihydroxypropoxy)-3-methoxyphenyl)pyrrolo[1,2-f][1,2,4]triazin-4(3H)-one

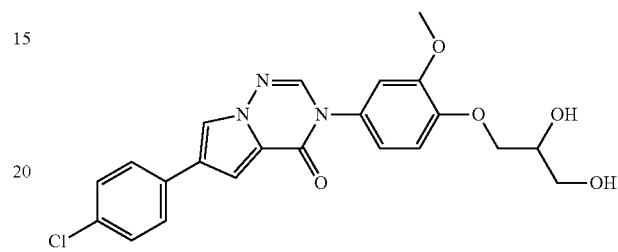

Example 66A (E)-4-(4-Chlorophenyl)-1-((dimethylamino)methyleneamino)-N-(3-methoxy-4-((2-(trimethylsilyl)ethoxy)methoxy)phenyl)-1H-pyrrole-2-carboxamide

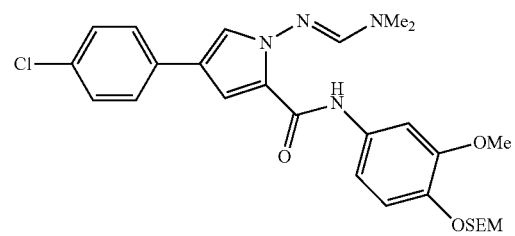

Example 66A was prepared from Example 18A in a manner analogous to Example 18D. LC-MS, [M+H]⁺=543.1.

Example 66B 6-(4-Chlorophenyl)-3-(3-methoxy-4-((2-(trimethylsilyl)ethoxy)methoxy)phenyl)pyrrolo[1,2-f][1,2,4]triazin-4(3H)-one

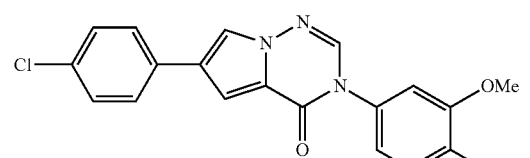

Example 66B was prepared in a manner analogous to Example 18. LC-MS, [M+H]⁺=498.2

Example 66C 6-(4-Chlorophenyl)-3-(4-hydroxy-3-methoxyphenyl)pyrrolo[1,2-f][1,2,4]triazin-4(3H)-one

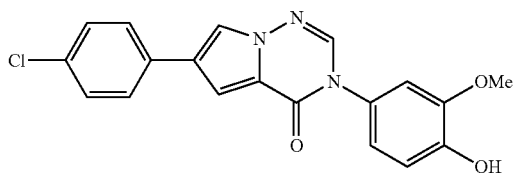 [SMILES: COc1cc(-n2cnn3cc(-c4ccc(Cl)cc4)cc3c2=O)ccc1O]

To a solution of Example 66B (200 mg, 0.402 mmol) in DCM (3 mL) was added 4N HCl/dioxane (3 mL, 0.402 mmol) and the mixture stirred for 1.5 h. A white solid precipitated from the reaction mixture within the first 5 minutes. Evaporation followed by trituration in ether and filtration yielded Example 66C (102 mg, 0.277 mmol, 69.1% yield) as a white solid.

Example 66D 3-(4-(Allyloxy)-3-methoxyphenyl)-6-(4-chlorophenyl)pyrrolo[1,2-f][1,2,4]triazin-4(3H)-one

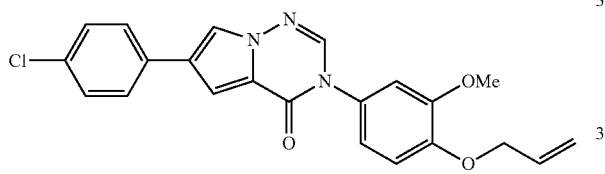

A mixture of Example 66C, $K_2CO_3$, and allyl bromide (15 µL) in DMF was stirred at RT O.N. The mixture was diluted with DCM, washed with 1N HCl, brine, dried ($Na_2SO_4$), and evaporated under reduced pressure to obtain a residue which was purified by flash chromatography (4 g, 0% to 100% EtOAc-Hexanes) to yield Example 66D (13.6 mg, 0.033 mmol, 61.3% yield) as a white solid. LC-MS, $[M+H]^+$=408.0.

Example 66

6-(4-Chlorophenyl)-3-(4-(2,3-dihydroxypropoxy)-3-methoxyphenyl)pyrrolo[1,2-f][1,2,4]triazin-4(3H)-one

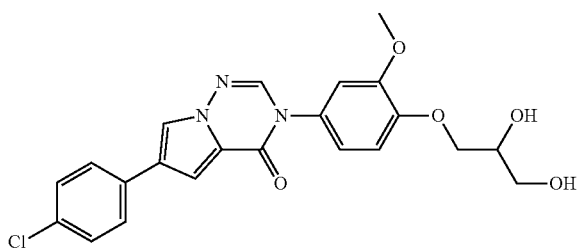 [SMILES: COc1cc(-n2cnn3cc(-c4ccc(Cl)cc4)cc3c2=O)ccc1OCC(O)CO]

To a solution of Example 66D (13 mg, 0.032 mmol) in acetone (1 mL) and water (0.5 mL) was added $OsO_4$ (10 µL, 1.274 µmol) and NMO (12 mg, 0.102 mmol) and the mixture stirred at RT O.N. Aq $Na_2SO_3$ was added to the reaction mixture and the mixture stirred for 10 min. The mixture was then diluted with EtOAc (20 mL) and $H_2O$ (20 mL) and transferred to a separatory funnel The organic layer was washed with brine, dried ($Na_2SO_4$), filtered, and evaporated to yield a white solid which was sparingly soluble in MeOH. The solid was dissolved in minimum MeOH-DMF and purified by Preparative HPLC (PHENOMENEX® Luna Axia 5µ C18 30×100 mm; 10 min gradient from 60% A: 40% B to 0% A:100% B (A=90% $H_2O$/10% MeOH+0.1% TFA); (B=90% MeOH/10% $H_2O$+0.1% TFA); detection at 220 nm) to yield Example 66 (2.7 mg, 5.80 µmol, 18.21% yield) as a white solid. LC-MS, $[M+H]^+$=442.0. $^1$H NMR (CDCl$_3$, 400 MHz): δ 7.69 (d, J=2.2 Hz, 1H), 7.62 (s, 1H), 7.54 (d, J=8.3 Hz, 2H), 7.38 (d, J=8.2 Hz, 2H), 7.35-7.38 (m, 1H), 7.03 (d, J=8.3 Hz, 1H), 6.88-6.95 (m, 2H), 4.20-4.27 (m, 2H), 4.10-4.17 (m, 2H), 3.89 (s, 3H), 3.78-3.90 (m, 2H). HPLC-1: Rt=8.8 min, purity=96%; HPLC-1: Rt=8.2 min, purity=96%.

Example 67

(R)-6-(4-Chlorophenyl)-3-(4-(2-hydroxypropoxy)-3-methoxyphenyl)pyrrolo[1,2-f][1,2,4]triazin-4(3H)-one

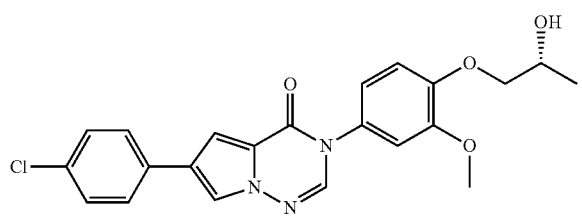 [SMILES: COc1cc(-n2cnn3cc(-c4ccc(Cl)cc4)cc3c2=O)ccc1OC[C@@H](C)O]

Example 67A (R)-1-(4-Amino-2-methoxyphenoxy)propan-2-ol

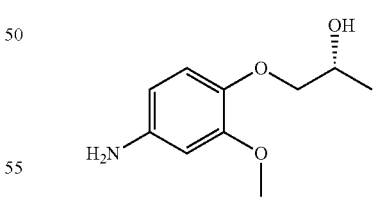

A slurry of (R)-1-(2-methoxy-4-nitrophenoxy)propan-2-ol U.S. Publication No. 2007/0093509, 2.57 g, 11.3 mmol) and 10% Palladium on Carbon (0.602 g, 0.570 mmol) in EtOH (30 mL) was allowed to stir at RT under an $H_2$ (1 atm, balloon) atmosphere for 5.0 h. The reaction mixture was filtered through a pad of CELITE®, washed with MeOH, concentrated and air-dried under vacuum to give Example 67A (1.93 g, 87% yield) as a light brown solid which was used in the next step without purification: LC-MS, $[M+H]^+$=198.2.

Example 67B (R,E)-4-(4-Chlorophenyl)-1-((dimethylamino)methyleneamino)-N-(4-(2-hydroxypropoxy)-3-methoxyphenyl)-1H-pyrrole-2-carboxamide

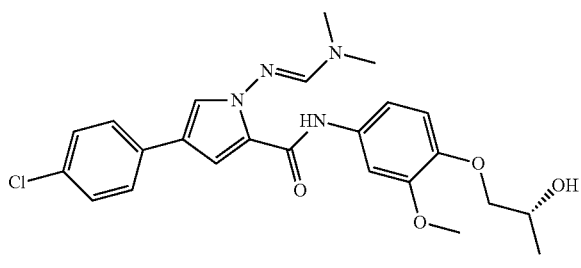 [SMILES: COc1cc(NC(=O)c2cc(-c3ccc(Cl)cc3)cn2/N=C/N(C)C)ccc1OC[C@@H](C)O]

To a suspension of Example 18A (1.47 g, 5.04 mmol) in DMF (10 mL) was added EDC.HCl (2.90 g, 15.12 mmol), HOBt (0.386 g, 2.52 mmol), and DIPEA (80 µL, 0.458 mmol). The mixture was stirred at RT for 1 h and then a solution of Example 67A (1.093 g, 5.54 mmol) in DMF (3.5 mL) was added over a period of 5 min. The resulting solution was stirred at RT for 20 h. Upon completion, the reaction mixture was diluted with H$_2$O (100 ml) and the solid that formed was filtered, washed well with water and air-dried under vacuum to afford Example 67B (1.90 g, 80% yield) as a light tan solid which was used in the next step without further purification. LC-MS, [M+H]$^+$=471.3. $^1$H NMR (500 MHz, DMSO-d$_6$) δ 10.80 (s, 1H), 8.40 (s, 1H), 7.82 (d, J=2.20 Hz, 1H), 7.61 (d, J=8.25 Hz, 2H), 7.28-7.43 (m, 3H), 7.14 (d, J=2.20 Hz, 1H), 7.03-7.12 (m, 1H), 6.92 (d, J=8.25 Hz, 1H), 4.80 (d, J=4.40 Hz, 1H), 3.92 (ddd, J=11.27, 6.05, 5.77 Hz, 1H), 3.59-3.83 (m, 5H), 3.08 (d, J=10.45 Hz, 6H), 1.06-1.17 (3H, m).

Example 67

(R)-6-(4-Chlorophenyl)-3-(4-(2-hydroxypropoxy)-3-methoxyphenyl)pyrrolo[1,2-f][1,2,4]triazin-4(3H)-one

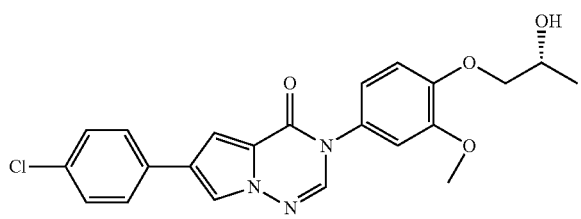 [SMILES: COc1cc(-n2cnn3cc(-c4ccc(Cl)cc4)cc3c2=O)ccc1OC[C@@H](C)O]

A solution of Example 67B (830 mg, 1.76 mmol) and catalytic acetic acid (0.101 mL, 1.76 mmol) (3 drops) in CH$_3$CN (10.00 mL) was heated at 160° C. for 0.5 h under microwave irradiation. Upon cooling, the precipitate was filtered, washed well with MeOH and air-dried under vacuum to give Example 67 (570 mg, 74% yield) as an off-white solid which was used in the next step without further purification. LC-MS, [M+H]$^+$=426.2. $^1$H NMR (400 MHz, DMSO-d$_6$) δ 8.25 (s, 1H), 8.11 (s, 1H), 7.82 (d, J=8.79 Hz, 2H), 7.36-7.50 (m, 3H), 7.16 (d, J=2.20 Hz, 1H), 7.05-7.11 (m, 1H), 6.97-7.04 (m, 1H), 4.87 (d, J=4.95 Hz, 1H), 3.97 dt, J=10.99, 5.50 Hz, 1H), 3.78-3.93 (m, 2H), 3.77 (s, 3H), 1.16 (d, J=6.60 Hz, 3H).

Example 68

(S)—((R)-1-(4-(6-(4-Chlorophenyl)-4-oxopyrrolo[1,2-f][1,2,4]triazin-3(4H)-yl)-2-methoxyphenoxy)propan-2-yl) 2-amino-3-methylbutanoate, HCl salt

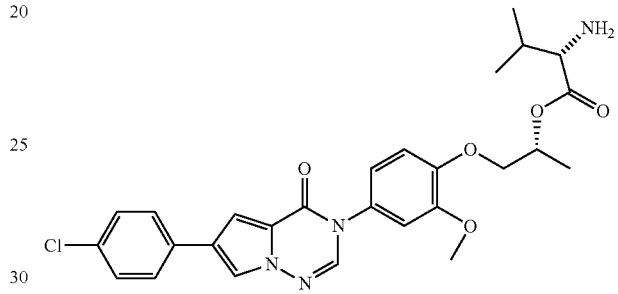

Example 68A (S)—((R)-1-(4-(6-(4-Chlorophenyl)-4-oxopyrrolo[1,2-f][1,2,4]triazin-3(4H)-yl)-2-methoxyphenoxy)propan-2-yl) 2-(tert-butoxycarbonylamino)-3-methylbutanoate

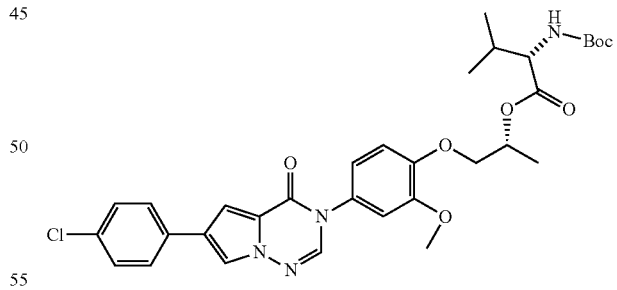

To a suspension of Example 67 (1.60 g, 3.76 mmol), DMAP (0.092 g, 0.751 mmol) and BOC-Val-OH (0.979 g, 4.51 mmol) in DCM (18.8 mL) at reflux was added DIC (0.937 mL, 6.01 mmol) dropwise over a period of 1 h. Stirring was continued at reflux for 2 h; whereupon the mixture was cooled to 0° C. and filtered. The filtrate was washed with cold 1N HCl (3×75 mL) and cold 10% NaHCO$_3$ (3×75 mL) prior to drying over anhydrous Na$_2$SO$_4$ and concentrating under vacuum. The residue was purified by flash chromatography (silica gel, hexanes:EtOAc, 100:0 to 0:100) to afford (2.15 g, 92% yield) of Example 68A as a white solid. LC-MS, [M+H]$^+$=625.4.

Example 68

(S)—((R)-1-(4-(6-(4-Chlorophenyl)-4-oxopyrrolo[1,2-f][1,2,4]triazin-3(4H)-yl)-2-methoxyphenoxy)propan-2-yl) 2-amino-3-methylbutanoate, HCl salt

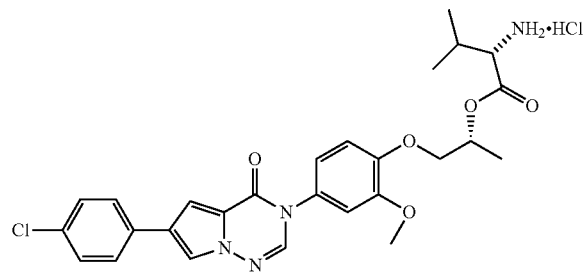

To a mixture of Example 68A (2.10 g, 3.36 mmol) in dioxane (33.6 mL) was added 4N HCl in dioxane (42.0 mL, 168 mmol) and the reaction was stirred at RT for 2 h. Most of the solvent was evaporated. The resulting slurry was diluted with Et$_2$O (300 mL). The mixture was stirred for 5 min and subjected to filtration. The solid was washed with Et$_2$O (3×50 ml) and lyophilized to give Example 68 as a white solid (1.74 g, 88% yield). LC-MS, [M+H]$^+$=525.3. $^1$H NMR (500 MHz, DMSO-d$_6$) δ 8.38 (br. s., 3H), 8.26 (s, 1H), 8.11 (s, 1H), 7.82 (d, J=8.25 Hz, 2H), 7.38-7.49 (m, 3H), 7.20 (d, J=2.20 Hz, 1H), 7.13 (d, J=8.80 Hz, 1H), 6.99-7.08 (m, 1H), 5.24-5.35 (m, 1H), 4.11-4.22 (m, 2H), 3.92 (d, J=3.85 Hz, 1H), 3.77 (s, 3H), 2.11-2.23 (m, 1H), 1.36 (d, J=6.60 Hz, 3H), 0.99 (dd, J=16.22, 6.87 Hz, 6H).

Biological Evaluation

Radioligand Binding Assay for Assessment of MCHR1 Activity

Membranes from stably transfected HEK-293 cells expressing a mutated (E4Q, A5T) hMCHR1 receptor were prepared by dounce homogenization and differential centrifugation. Binding experiments were carried out with 0.5-1.0 ug of membrane protein incubated in a total of 0.2 ml in 25 mM HEPES (pH 7.4) with 10 mM MgCl$_2$, 2 mM EGTA, and 0.1% BSA (Binding Buffer) for 90 min. For competition binding assays, reactions were carried out in the presence of with 0.06-0.1 nM [Phe$^{13}$, [$^{125}$I]Tyr$^{19}$]-MCH and increasing concentrations of unlabeled test molecules. Reactions were terminated by rapid vacuum filtration over 96 well-GFC UNIFILTER® plates pre-coated with 0.075 ml binding buffer containing 1% BSA, and washed 3 times with 0.4 ml of Phospho-buffered Saline (pH 7.4) containing 0.01% TX-100. Filters were dried, 0.05 ml microscint 20 was added to each well and radioactivity was subsequently quantified by scintillation counting on a TOPCOUNT® microplate scintillation counter (Packard). Inhibitory constants were determined by nonlinear least squares analysis using a four parameter logistic equation.

| Example No. | MCHR1 Human Binding (Ki, nM) | MCHR1 Rat Binding (Ki, nM) |
|---|---|---|
| 1 | 4.42 | 2.76 |
| 2 | 21.38 | 8.29 |
| 3 | 4.49 | 2.79 |
| 4 | 0.52 | 0.7 |
| 6 | 2.2 | 0.8 |

| Example No. | MCHR1 Human Binding (Ki, nM) |
|---|---|
| 13 | 0.17 |
| 57 | 9 |
| 56 | 9.4 |
| 18 | 11.5 |
| 38 | 76.1 |
| 31 | 124.1 |
| 61 | 126 |

Assessment of In Vivo MCHR Activity

Male SPRAGUE DAWLEY® (CD, Charles River Breeding Laboratory) rats weighing approximately 240 grams were place in individual plastic cages with ALPHADR1® bedding. The room was maintained at 72° F. and 50% humidity, and a 12/12 light dark cycle with lights out at 1600 hours. The rats were conditioned for 5 days prior to the start of the study to having a choice of foods. A normal chow (HARLAN TEKLAD®, 2018) that contains 18% protein, 5% fat and 73% carbohydrate and a high fat high sugar diet (Research Diets (D2327)) that contains 20% protein, 40% fat and 40% carbohydrate where the carbohydrate is entirely sucrose and the fat is soybean and coconut oil. Studies have revealed that rats exhibit a high preference for the high coconut oil. Studies have revealed that rats exhibit a high preference for the high fat/high sucrose dies (80% preference). Body weight and consumption of both kinds of food as well as water intake were measured daily. Water was available ad lib throughout the study. Food consumption is presented as daily caloric consumption which is the sum of grams of chow multiplied by the Kcal per gram (3.5) plus grams of high fat high sugar multiplied by Kcal per gram (4.59).

Baseline body weight was measured prior to drug treatment on day 0 of the study. Baseline food consumption was the average of the 3 days prior to the first drug treatment. Drug was administered daily p.o. at 2.0 ml/kg at 1500 hours beginning on day 0 and continuing daily through day 4 as a suspension in 0.5% methyl cellulose, 0.1% Tween 80 in water at 3.0, 10 and 30 mg/kg p.o. All data were evaluated using ANOVA and Fishers PLSD statistics.

Biological Data Dose: 30 mg/kg

| Example | % Weight Reduction versus Vehicle |
|---|---|
| 1 (dosed as 22) | 6.9 |
| 33 (dosed as 63) | 11.2 |
| 46 (dosed as 50) | 2.6 |

It should be understood that while this application has been described herein in terms of specific embodiments set forth in detail, such embodiments are presented by way of illustration of the general principles of the application, and the application is not necessarily limited thereto. Certain modifications and variations in any given material, process step or chemical formula will be readily apparent to those skilled in the art without departing from the true spirit and scope of the present application, and all such modifications and variations should be considered within the scope of the claims that follow.

What is claimed is:

1. A compound of formula I

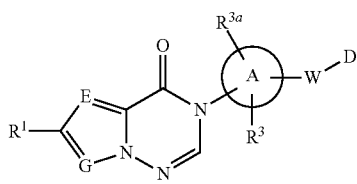

I or a pharmaceutically acceptable salt or stereoisomer thereof:
wherein

is selected from the group consisting of monocyclic aryl or monocyclic heteroaryl;

W is selected from the group consisting of a direct bond, —O—, and —N($R^6$)—; provided that if W is a direct bond, D is a cyclic amine that is attached to A via the nitrogen atom of the cyclic amine;

D is selected from the group consisting of a direct bond, unsubstituted $C_1$ to $C_4$ alkyl, unsubstituted $C_3$ to $C_7$ cycloalkyl, cycloalkyl, a 4- to 6-membered cyclic amine, substituted $C_1$ to $C_4$ alkyl with $R^{2a}$, $R^{2b}$, and $R^{2c}$, and substituted $C_3$ to $C_7$ cycloalkyl with $R^{2a}$, $R^{2b}$, and $R^{2c}$;

E and G are independently N or CH provided that both are not N and both are not CH;

$R^1$ is substituted or unsubstituted phenyl or substituted or unsubstituted monocyclic heteroaryl;

$R^{2a}$, $R^{2b}$, and $R^{2c}$ are independently selected from the group consisting of hydrogen, halo, cyano, hydroxyl, —$NR^5R^{5a}$, —$SO_2R^{34}$, —$CO_2R^{35}$—$NR^5CO_2R^{21}$, —$NR^5COR^{21}$, substituted or unsubstituted $C_1$ to $C_4$ alkyl, substituted or unsubstituted $C_3$ to $C_7$ cycloalkyl, substituted or unsubstituted 4- to 6-membered cyclic amines wherein said cyclic amine is optionally substituted with —OH, carbonylamino, alkoxycarbonylamino, or any two of $R^{2a}$, $R^b$, or $R^{2c}$, may be taken together to form a ring;

$R^3$ and $R^{3a}$ are each independently selected from the group consisting of hydrogen, hydroxyl, lower alkoxy, halo, CN, substituted or unsubstituted $C_1$ to $C_4$ alkyl, perfluoroalkyl, substituted or unsubstituted $C_3$ to $C_7$ cycloalkyl, and cycloalkoxy, or $R^3$ or $R^{3a}$ and D may optionally be taken together with the atoms to which they are attached to form a 5- to 7-membered ring;

$R^5$ and $R^{5a}$ are independently selected from the group consisting of hydrogen, substituted or unsubstituted lower alkyl, hydroxyalkyl, hydroxyalkylcycloalkyl, substituted or unsubstituted heterocycloalkyl, acyl, alkoxycarbonyl, carboxyalkyl, substituted or unsubstituted cycloalkyl, and substituted or unsubstituted cycloalkylalkyl, or $R^5$ and $R^{5a}$ and the nitrogen atom to which they are attached may form a ring;

$R^{21}$ and $R^{31}$ are each H or $C_1$ to $C_4$ alkyl;

$R^{34}$ is alkyl;

$R^{35}$ is H or alkyl; and $R^6$ is selected from the group consisting of H, $C_1$ to $C_4$ alkyl and $C_3$ to $C_7$ cycloalkyl.

2. The compound according to claim 1 wherein D is a cyclic amine selected from the group consisting of pyrrolidinyl, morpholinyl, azetidinyl, piperidinyl, morphilinyl.

3. The compound according to claim 1 wherein D is a direct bond, unsubstituted $C_1$ to $C_4$ alkyl, or $C_1$ to $C_4$ alkyl with $R^{2a}$, $R^{2b}$, and $R^{2c}$; and each of $R^{2a}$, $R^{2b}$, and $R^{2c}$ are independently, hydrogen, hydroxyl, hydroxyalkyl, cyclopropyl, pyrrolidinyl, —$SO_2R^{34}$, —$CO_2H$, or $R^{2a}$ and $R^{2b}$ are joined together to form a cycloalkyl substituted with halo or hydroxyl.

4. The compound according to claim 1 wherein $R^1$ is phenyl, pyridinyl, or pyrimidinyl, any of which may be substituted with halo and

is selected from the group consisting of phenyl, pyridinyl, and pyrimidinyl.

5. The compound according to claim 2 wherein $R^1$ is phenyl, pyridinyl, or pyrimidinyl, any of which may be substituted with halo and

is selected from the group consisting of phenyl, pyridinyl, and pyrimidinyl.

6. The compound according to claim 3 wherein $R^1$ is phenyl, pyridinyl, or pyrimidinyl, any of which may be substituted with halo and

is selected from the group consisting of phenyl, pyridinyl, and pyrimidinyl.

7. A compound having the following structure or a pharmaceutically acceptable salt, or a stereoisomer thereof:

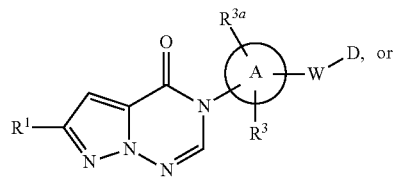

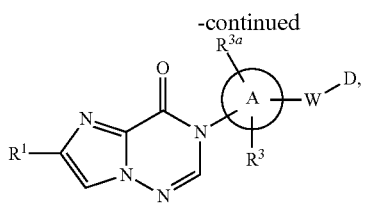

wherein

is phenyl, pyrimidinyl, or pyridinyl;
$R^1$ is phenyl, pyrimidinyl, or pyridinyl optionally substituted with halo;
$R^{3a}$ and $R^3$ are independently H or methoxy;
W is a direct bond or O, provided that if W is a direct bond, D is a cyclic amine that is attached to A via the nitrogen atom of the cyclic amine;
D is a direct bond, unsubstituted $C_1$ to $C_4$ alkyl, $C_1$ to $C_4$ alkyl with $R^{2a}$, $R^{2b}$, and $R^{2c}$, or a cyclic amine selected from pyrrolidinyl, morpholinyl, azetidinyl, piperidinyl, morphilinyl; and
$R^{2a}$, $R^{2b}$, and $R^{2c}$ are independently selected from the group consisting of hydrogen, halo, cyano, hydroxyl, —$NR^5R^{5a}$, —$SO_2R^{34}$, —$NR^5CO_2R^{21}$, $NR^5COR^{21}$, substituted or unsubstituted $C_1$ to $C_4$ alkyl, substituted or unsubstituted $C_3$ to $C_7$ cycloalkyl, substituted or unsubstituted 4- to 6-membered cyclic amines wherein said cyclic amine is optionally substituted with —OH, carbonylamino, alkoxycarbonylamino, or any two of $R^{2a}$, $R^b$, or $R^{2c}$, may be taken together to form a ring.

8. A compound according to claim 1 selected from one of the following compounds or a stereoisomer or a salt thereof:

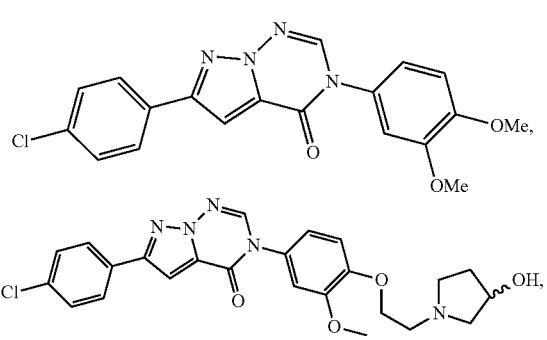

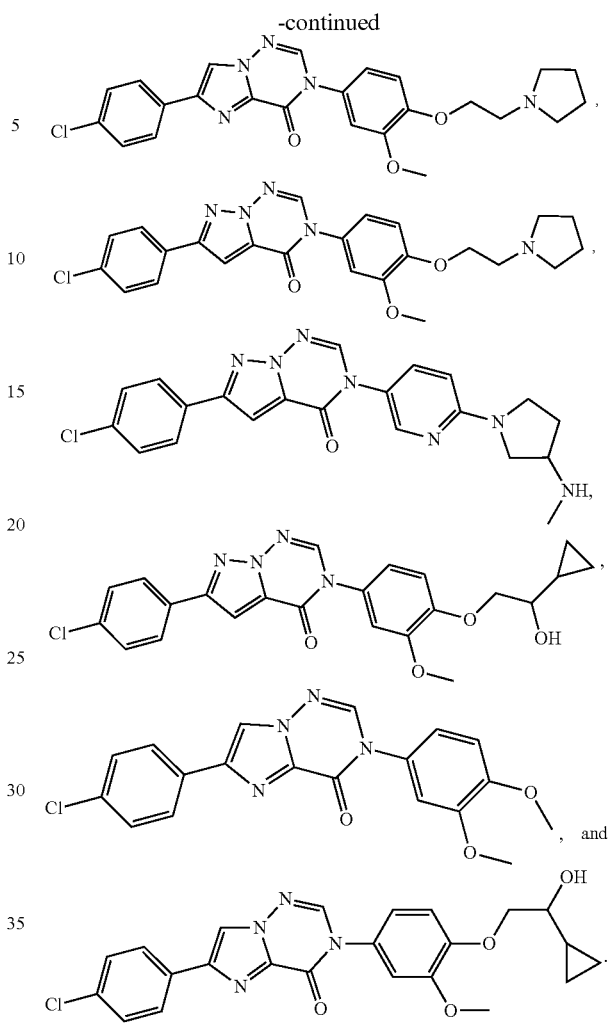

9. A pharmaceutical composition comprising one or more compounds according to claim 1 and a pharmaceutically acceptable carrier.

10. The pharmaceutical composition according to claim 9 comprising at least one additional antiobesity agent.

11. The pharmaceutical composition according to claim 9 and at least one additional antidiabetic agent.

12. A method for treating obesity comprising administering to a patient in need of such treatment a therapeutically effective amount of a compound according to claim 1.

13. A method for treating type II diabetes comprising administering to a patient in need of such treatment a therapeutically effective amount of a compound according to claim 1.

* * * * *

UNITED STATES PATENT AND TRADEMARK OFFICE
CERTIFICATE OF CORRECTION

PATENT NO. : 8,754,211 B2  Page 1 of 1
APPLICATION NO. : 14/041665
DATED : June 17, 2014
INVENTOR(S) : Pratik Devasthale et al.

It is certified that error appears in the above-identified patent and that said Letters Patent is hereby corrected as shown below:

On the Title Page
Item (56) Column 2
Line 14, "at" should read -- et --;
Line 16, "(2004." should read -- (2004). --;
Line 27, "at" should read -- et --;
Line 27, "Pharmaceutices," should read -- Pharmaceutics, --; and
Line 29, "at" should read -- et --.

In the Claims
Column 123
Line 40, "cycloalkyl," should read -- cycloalkylalkyl, --;
Line 49, "—$CO_2R^{35}$" should read -- —$CO_2R^{35}$, --; and
Line 55, "$R^b$," should read -- $R^{2b}$, --.

Column 125
Line 31, "$NR^5COR^{21}$," should read -- —$NR^5COR^{21}$, --; and
Line 37, "$R^b$," should read -- $R^{2b}$, --.

Signed and Sealed this
Seventh Day of October, 2014

Michelle K. Lee
*Deputy Director of the United States Patent and Trademark Office*